United States Patent
Langedijk et al.

(10) Patent No.: US 10,973,907 B2
(45) Date of Patent: Apr. 13, 2021

(54) RECOMBINANT ADENOVIRUSES ENCODING MOSAIC HUMAN IMMUNODEFICIENCY VIRUS (HIV) ENV, GAG, AND POL ANTIGENS

(71) Applicant: Janssen Vaccines & Prevention B.V., Leiden (NL)

(72) Inventors: Johannes Petrus Maria Langedijk, Amsterdam (NL); Danielle Van Manen, Alphen aan den Rijn (NL); Jort Vellinga, Leiden (NL); Frank Wegmann, Leiden (NL); Benoit Christophe Stephan Callendret, The Hague (NL); Anders Krarup, Glostrup (DK); Jörn Stitz, Cologne (DE)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 16/440,463

(22) Filed: Jun. 13, 2019

(65) Prior Publication Data
US 2019/0321462 A1    Oct. 24, 2019

Related U.S. Application Data

(62) Division of application No. 15/380,123, filed on Dec. 15, 2016, now Pat. No. 10,369,214.

(30) Foreign Application Priority Data

Dec. 15, 2015 (EP) .................................. 15200138
Oct. 17, 2016 (EP) .................................. 16194124

(51) Int. Cl.
| | | |
|---|---|---|
| *A61K 39/21* | (2006.01) | |
| *C07K 14/16* | (2006.01) | |
| *C07K 14/005* | (2006.01) | |
| *C12N 7/00* | (2006.01) | |
| *C12N 15/86* | (2006.01) | |
| C12N 15/861 | (2006.01) | |
| A61K 39/00 | (2006.01) | |

(52) U.S. Cl.
CPC ............ *A61K 39/21* (2013.01); *C07K 14/005* (2013.01); *C07K 14/162* (2013.01); *C12N 7/00* (2013.01); *C12N 15/86* (2013.01); *A61K 2039/5256* (2013.01); *C12N 15/861* (2013.01); *C12N 2710/10343* (2013.01); *C12N 2740/16111* (2013.01); *C12N 2740/16122* (2013.01); *C12N 2740/16134* (2013.01); *C12N 2740/16171* (2013.01); *C12N 2740/16234* (2013.01)

(58) Field of Classification Search
CPC .................. A61K 39/21; C07K 14/162; C12N 2740/16234; C12N 15/861; C12N 2740/16122; C12N 2740/16134

See application file for complete search history.

(56) References Cited

U.S. PATENT DOCUMENTS

| 4,603,112 A | 7/1986 | Paoletti et al. |
|---|---|---|
| 5,185,146 A | 2/1993 | Altenburger |
| 5,639,649 A | 6/1997 | Almond et al. |
| 5,643,576 A | 7/1997 | Johnston et al. |
| 6,761,893 B2 | 7/2004 | Chaplin et al. |
| 6,911,205 B2 | 6/2005 | Sodroski et al. |
| 7,429,653 B2 | 9/2008 | Sodroski et al. |
| 7,592,014 B2 | 9/2009 | Binley et al. |
| 7,901,690 B2 | 3/2011 | Lu et al. |
| 7,939,083 B2 | 5/2011 | Dey et al. |
| 8,197,825 B2 | 6/2012 | Sutter et al. |
| 9,017,691 B2 | 4/2015 | Barouch et al. |
| 2003/0206926 A1 | 11/2003 | Chaplin et al. |
| 2003/0207287 A1 | 11/2003 | Short |
| 2006/0159699 A1 | 7/2006 | Howley et al. |
| 2007/0166784 A1 | 7/2007 | Barnett et al. |
| 2007/0298051 A1 | 12/2007 | Barouch et al. |
| 2008/0199939 A1 | 8/2008 | Havenga et al. |
| 2008/0279879 A1 | 11/2008 | Zolla-Pazner |
| 2011/0159036 A1 | 6/2011 | Moss et al. |
| 2011/0250220 A1 | 10/2011 | Dey et al. |
| 2012/0045472 A1 | 2/2012 | Harrison et al. |
| 2012/0076812 A1 | 3/2012 | Barouch et al. |
| 2013/0189754 A1 | 7/2013 | Parks et al. |
| 2014/0302080 A1 | 10/2014 | Barouch et al. |
| 2014/0348791 A1 | 11/2014 | Barouch et al. |
| 2015/0246112 A1 | 9/2015 | Barouch et al. |

(Continued)

FOREIGN PATENT DOCUMENTS

| CN | 102282175 A | 12/2011 |
|---|---|---|
| EP | 2292772 A1 | 3/2011 |

(Continued)

OTHER PUBLICATIONS

Walker, B. D. and D. R. Burton, May 2008, Toward an AIDS Vaccine, Science 320:760-764.*
Subbaraman, H., et al., 2018, Broadly neutralizing antibodies: What is needed to move from a rare event in HIV-1 infection to vaccine efficacy, Retrovirol. 15:52, pp. 1-14.*
Rios, A., 2018, Fundamental challenges to the development of a preventive HIV vaccine, Curr. Opin. Virol. 29:26-32.*
Barouch, D. H., 2008, Challenges in the development of an HIV-1 vaccine, Nature 455:613-619.*

(Continued)

*Primary Examiner* — Jeffrey S Parkin
(74) *Attorney, Agent, or Firm* — Ice Miller LLP

(57) ABSTRACT

Compositions and vaccine combinations containing synthetic HIV envelope proteins, and methods for inducing an immune response against human immunodeficiency virus (HIV) infection are described. Viral expression vectors encoding the synthetic HIV envelope proteins can be used in the vaccine combinations to induce immune responses against HIV and provide improved protective immunity against HIV.

15 Claims, 7 Drawing Sheets

Specification includes a Sequence Listing.

(56) References Cited

U.S. PATENT DOCUMENTS

| | | | |
|---|---|---|---|
| 2015/0291935 | A1 | 10/2015 | Barouch et al. |
| 2016/0024156 | A1 | 1/2016 | Barouch et al. |
| 2016/0122392 | A1 | 5/2016 | Baker et al. |
| 2017/0165355 | A1 | 6/2017 | Langedijk |
| 2017/0362280 | A1 | 12/2017 | Nguyen et al. |
| 2018/0064803 | A1 | 3/2018 | Tomaka et al. |
| 2018/0072777 | A1 | 3/2018 | Rutten et al. |

FOREIGN PATENT DOCUMENTS

| | | | |
|---|---|---|---|
| EP | 2319860 A2 | 5/2011 | |
| WO | 20070071 A1 | 11/2000 | |
| WO | 0119958 | 3/2001 | |
| WO | 200242480 A2 | 5/2002 | |
| WO | 2003048184 A2 | 6/2003 | |
| WO | 2003/104467 A1 | 12/2003 | |
| WO | 2004/0044155 | 5/2004 | |
| WO | 2006002079 | 1/2006 | |
| WO | 2006020071 | 2/2006 | |
| WO | 2006/040330 | 4/2006 | |
| WO | 2007005934 | 1/2007 | |
| WO | 2007/024941 A2 | 3/2007 | |
| WO | 2007104792 A2 | 9/2007 | |
| WO | 2007/149491 | 12/2007 | |
| WO | 2008063331 | 5/2008 | |
| WO | 2008107370 A1 | 9/2008 | |
| WO | 2010/042942 A2 | 4/2010 | |
| WO | 2010/059732 A1 | 5/2010 | |
| WO | 2010096561 A1 | 8/2010 | |
| WO | 2011/082087 A2 | 7/2011 | |
| WO | 2011/092029 A1 | 8/2011 | |
| WO | 2012/030904 | 3/2012 | |
| WO | 2013055908 | 4/2013 | |
| WO | 2014/047261 | 3/2014 | |
| WO | 2014107744 A1 | 7/2014 | |
| WO | 2014/124301 A1 | 8/2014 | |
| WO | 2015/048770 | 4/2015 | |
| WO | 2016037154 A1 | 3/2016 | |
| WO | 2016049287 A1 | 3/2016 | |
| WO | 2016146844 A1 | 9/2016 | |
| WO | 2017102929 A1 | 6/2017 | |

OTHER PUBLICATIONS

Lodi et al., "Immunovirologic Control 24 Months After Interruption of Antiretroviral Therapy Initiated Close to HIV Seroconversion", Archives of Internal Medicine, vol. 172, No. 16, pp. 1252-1255 (2012).

Lopez-Sagaseta et al, "Self-Assembling Protein Nanoparticles in the Design of Vaccines," Computational and Structural Biotechnology Journal, vol. 14, pp. 58-68 (2016).

Lore et al., "Myeloid and Plasmacytoid Dendritic Cells are Susceptible to Recombinant Adenovirus Vectors and Stimulate Polyfunctional Memory T Cell Responses", J. Immunol, vol. 179, No. 3, pp. 1721-1729 (2007).

Lynch et al, "The Development of CD4 Binding Site Antibodies During HIV-1 Infection," Journal of Virology, vol. 86, No. 14, pp. 7588-7595 (Jul. 2012).

Malherbe et al, "Sequential Immunization with a Subtype B HIV-1 Envelope Quasispecies Partially Mimics the in Vivo Development of Neutralizing Antibodies," Journal of Virology, vol. 85, No. 11, pp. 5262-5274 (Jun. 2011).

Mangeat et al, "Lentiviral Vectors and Antiretroviral Intrinsic Immunity," Human Gene Therapy, vol. 16, No. 8, pp. 913-920 (Aug. 2005).

Mascola et al, "Protection of Macaques Against Pathogenic Simian/Human Immunodeficiency Virus 89.6PD by Passive Transfer of Neutralizing Antibodies," Journal of Virology, vol. 73, No. 5, pp. 4009-4018 (May 1999).

Mascola et al, "Protection of Macaques Against Vaginal Transmission of a Pathogenic HIV-1/SIV Chimeric Virus by Passive Infusion of Neutralizing Antibodies," Nature Medicine, vol. 6, No. 2, pp. 207-210 (Feb. 2000).

Masopust et al., "Hidden Memories: Frontline Memory T Cells and Early Pathogen Interception", J. Immunol., vol. 188, No. 12, pp. 5811-5817 (2012).

Mast et al., "International Epidemiology of Human Pre-Existing Adenovirus (Ad) Type-5, Type-6, Type-26 and Type-36 Neutralizing Antibodies: Correlates of High Ad5 Titers and Implications for Potential HIV Vaccine Trials", Vaccine, vol. 28: pp. 950-957 (2010).

Mayr et al., "The Small Pox Vaccination Strain MVA: Marker, Genetic Structure, Experience Gained with the Parenteral Vaccination and Behavior in Organisms with a Debilitated Defence Mechanism," Zentralbl Bacteriol. vol. 167, pp. 375-390 (1978) (Abstract Only).

McBurney et al, "Evaluation of Heterologous Vaginal SHIV SF162p4 Infection Following Vaccination with a Polyvalent Clade B Virus-Like Particle Vaccine," AIDS Research and Humam Retroviruses, vol. 28, No. 9, pp. 863-872 (2012).

McBurney et al, "Human Immunodeficiency Virus-Like Particles with Consensus Envelopes Elicited Broader Cell-Mediated Peripheral and Mucosal Immune Responses than Polyvalent and Monovalent Env Vaccines," Vaccine, vol. 27, No. 32, pp. 4337-4349 (2009).

McCoy et al, "Potent and Broad Neutralization of HIV-1 by a Llama Antibody Elicited by Immunization," The Journal of Experimental Medicine, vol. 209, No. 6, pp. 1091-1103 (2012).

McElrath et al, "Induction of Immunity to Human Immunodeficiency Virus Type-1 by Vaccination," Immunity, vol. 33, pp. 542-554 (Oct. 29, 2010).

McElrath et al., "HIV-1 Vaccine-Induced Immunity in the Test-of-Concept Step Study: A Case-Cohort Analysis", Lancet, vol. 372, No. 9653, pp. 1894-1905 (2008).

McGuire et al, "Engineering HIV Envelope Protein to Activate Germline B Cell Receptors of Broadly Neutralizing Anti-CD4 Binding Site Antibodies," The Journal of Experimental Medicine, vol. 210, No. 4, pp. 655-663 (2013).

McLellan et al, "Structure of HIV-1 gp120 V1/V2 Domain with Broadly Neutralizing Antibody PG9," Nature, vol. 480, No. 7377, pp. 336-343 (2011).

Montefiori et al, "Antibody-Based HIV-1 Vaccines: Recent Developments and Future Directions," PLOS Medicine, vol. 4, No. 12, pp. e348 (2007).

Montefiori, "Evaluating Neutralizing Antibodies Against HIV, SIV, and SHIV in Luciferase Reporter Gene Assays," Current Protocols in Immunology, vol. 12, No. 11, pp. 1-17 (2004).

Montefiori, "Measuring HIV Neutralization in a Luciferase Reporter Gene Assay," HIV Protocols Second 25 Edition, vol. 485, pp. 395-405 (2009).

Morner et al, "Human Immunodeficiency Virus Type 1 ENV Trimer Immunization of Macaques and Impact of D Priming with Viral Vector or Stabilized Core Protein," Journal of Virology, vol. 83, No. 2, pp. 540-551 (Jan. 2009).

Mouquet et al, "Complex-Type N-Glycan Recognition by Potent Broadly Neutralizing HIV Antibodies," Proceedings of the National Academy of Sciences of the United States of America, vol. 109, No. 47, pp. E3268-E3277 (2012).

Nara et al, "Purified Envelope Glycoproteins from Human Immunodeficiency Virus Type 1 Variants Induce Individual, Type-Specific Neutralizing Antibodies," Journal of Virology, vol. 62, No. 8, pp. 2622-2628 (Aug. 1988).

NCBI Blast for GenBank AAY23526.1, Jul. 2016, "Envelope glycoprotein Human immunodeficiency virus 1", downloaded from web page: http://www.ncbi.nlm.nih.gov/protein/62956393, Download date: Feb. 8, 2018 (2 pages).

Nkolola et al, "Stability and Neutralization Capacity of a Novel Mosaic HIV-1 gp140 trimer in a Guinea Pig Model" AIDS Vaccine Poster, Ragon Institute, 1 pg. (2012).

Nkolola et al, "Stability and Neutralization Capacity of a Novel Mosaic HIV-1 gp140 Trimer in a Guinea Pig Model," Retrovirology, vol. 9, Supp. 2, pp. 299 (2012).

Nkolola et al., "Breadth of Neutralizing Antibodies Elicited by Stable, Homogeneous Clade A and Clade C HIV-1 gp140 Envelope Trimers in Guinea Pigs", Journ. of Viro., vol. 84. No. 7, pp. 3270-3279 (Apr. 2010).

(56) References Cited

OTHER PUBLICATIONS

Nkolola et al., "Characterization and Immunogenicity of a Novel Mosaic M HIV-1 gp140 Trimer", Journ. of Virology, vol. 88, No. 17, pp. 9538-9552 (Sep. 2014).
Ofek et al, "Structure and Mechanistic Analysis of the Anti-Human Immunodeficiency Virus Type 1 Antibody 2F5 in Complex with Its gp41 Epitope," Journal of Virology, vol. 78, No. 19, pp. 10724-10737 (Oct. 2004).
Page et al, "Studies on the Immunogenicity of Chinese Hamster Ovary Cell-Derived Recombinant gp120 (HIV-1111B)," Vaccine, vol. 9, pp. 47-52 (Jan. 1991).
Pancera et al, "Crystal Structure of PG16 and Chimeric Dissection with Somatically Related PG9: Structure-Function Analysis of Two Quaternary-Specific Antibodies That Effectively Neutralize HIV-1," Journal of Virology, vol. 84, No. 16, pp. 8098-8110 (Aug. 2010).
Pancera et al, "Structure of HIV-1 gp120 with gp41-Interactive Region Reveals Layered Envelope Architecture and Basis of Conformational Mobility," Procedures of the National Academy of Sciences of the United States of America, vol. 107, No. 3, pp. 1166-1171 (2010).
Pantophlet et al, "GP120: Target for Neutralizing HIV-1 Antibodies," Annu. Rev. Immunol., vol. 24, pp. 739-769 (2006).
Patterson et al. "Protection Against Mucosal Simian Immunodeficiency Virus SIVmac251 Challenge by Using Replicating Adenovirus-SIV Multigene Vaccine Priming and Subunit Boosting," Journal of Virology, vol. 78, No. 5, pp. 2212-2221 (Mar. 2004).
Pejchal et al, "A Potent and Broad Neutralizing Antibody Recognizes and Penetrates the HIV Glycan Shield," Science, vol. 334, No. 6059, pp. 1097-1103 (2011).
Pejchal et al, "Structure and Function of Broadly Reactive Antibody PG16 Reveal an H3 Subdomain that Mediates Potent Neutralization of HIV-1," Proceedings of the National Academy of Sciences of the United States of America, vol. 107, No. 25, pp. 11483-11488 (2010).
Peng et al. "Replicating Rather than Nonreplicating Adenovirus-Human Immunodeficiency Virus Recombinant Vaccines Are Better at Eliciting Potent Cellular Immunity and Priming High-Titer Antibodies," Journal of Virology, vol. 79, No. 16, pp. 10200-10209 (Aug. 2005).
Pinter, "Roles of HIV-1 Env Variable Regions in Viral Neutralization and Vaccine Development", Current HIV Research, vol. 5, No. 6, pp. 542-553 (2007).
Pitisuttihum et al., "Randomized, Double-Blind, Placebo-Controlled Efficacy Trial of a Bivalent Recombinant Glycoprotein 120 HIV-1 Vaccine Among Injection Drug Users in Bangkok, Thailand", J. Infect. Dis., vol. 194, No. 12, pp. 1661-1671 (2006).
Plotkin et al, "Postscript Relating to New Allegations Made by Edward Hooper at The Royal Society Discussion Meeting on Sep. 11, 2000," Philosophical Transactions of the Royal Society of London B: Biological Sciences, vol. 356, No. 1410, pp. 825-829 (2001).
Plotkin, "Correlates of Protection Induced by Vaccination," Clinical and Vaccine Immunology, vol. 17, No. 7, pp. 1055-1065 (Jul. 2010).
Plotkin, "Immunologic Correlates of Protection Induced by Vaccination," Pediatric Infectious Disease Journal, vol. 20, No. 1, pp. 63-75 (2001).
Plotkin, "The RV144 Thai HIV Vaccine Trial," Human Vaccines, vol. 6, No. 2, p. 159 (Feb. 2010).
Polonis et al, "Recent Advances in the Characterization of HIV-1 Neutralization Assays for Standardized Evaluation of the Antibody Response to Infection and Vaccination," Virology, vol. 375, pp. 315-320 (2008).
Pugach et al, "A Native-Like SOSIP.664 Trimer Based on an HIV-1 Subtype B Env Gene," Journal of Virology, vol. 89, No. 6, pp. 3380-3395 (2015).
Rerks-Ngarm et al., Vaccination with ALVAC and AIDSVAX to Prevent HIV-1 Infection in Thailand, N. Engl J Med., vol. 361, No. 23, pp. 2209-2220 (2009).

Rodenburg et al, "Near Full-Length Clones and Reference Sequences for Subtype C Isolates of HIV Type 1 from Three Different Continents," AIDS Research and Human Retroviruses, vol. 17, No. 2, pp. 161-168 (2001).
Saez-Cirion et al., "Post-Treatment HIV-1 Controllers with a Long-Term Virological Remission after the Interruption of Early Initiated Antiretroviral Therapy ANRS VISCONTI Study", PLOS Pathogens, vol. 9, No. 3, 12 pgs (Mar. 2013).
Salminen et al, "Full-length Sequence of an Ethiopian Human Immunodeficiency Virus Type 1 (HIV-1) Isolate of Genetic Subtype C," AIDS Res. Human Retroviruses, vol. 12, No. 14, pp. 1329-1339 (1996).
Sanders et al, "HIV-1 Neutralizing Antibodies Induced by Native-Like Envelope Trimers," Science, vol. 349, Issue 6244, pp. 1-17 (2015).
Sanders et al, "Stabilization of the Solubale, Cleaved, Trimeric Form of the Envelope Glycoprotein Complex of Human Immunodeficiency Virus Type 1," Journal of Virology, vol. 76, No. 17, pp. 8875-8889 (2002).
Sanders et al., "Brunenders: A Partially Attenuated Historic Poliovirus Type 1 Vaccine Strain", Journ. of General Viro., vol. 96, pp. 2614-2622 (2015).
Santra et al., "Mosaic Vaccines Elicit CD8+ T Lymphocyte Responses That Confer Enhanced Immune Coverage of Diverse HIV Strains in Monkeys", Nat Med., vol. 16, No. 3, pp. 324-328 (2010).
Saphire et al, "Crystal Structure of a Neutralizing Human IgG Against HIV-1: A Template for Vaccine Design," Science, vol. 293, No. 5532, pp. 1155-1159 (2001).
Sarzotti-Kelsoe et al, "Optimization and Validation of the TZM-bl Assay for Standardized Assessments of Neutralizing Antibodies Against HIV-1," Journal of Immunological Methods, vol. 409, pp. 131-146 (2014).
Sattentau, "Envelope Glycoprotein Trimers as HIV-1 Vaccine Immunogens", Vaccines, vol. 1, pp. 497-512 (2013).
Scheid et al, "Broad Diversity of Neutralizing Antibodies Isolated From Memory B Cells in HIV-Infected Individuals," D Nature, vol. 458, pp. 636-640 (Apr. 2, 2009).
Scheid et al, "Sequence and Structural Convergence of Broad and Potent HIV Antibodies That Mimic CD4 Binding," Science, vol. 333, pp. 1633-1637 (2011).
Schnierle et al, "Pseudotyping of Murine Leukemia Virus with the Envelope Glycoproteins of HIV Generates a Retroviral Vector with Specificity of infection for CD4-Expressing Cells," Proceedings of the National Academy of Sciences of the United States of America, vol. 94, pp. 8640-8645 (Aug. 1997).
Seaman et al, "Multiclade Human Immunodeficiency Virus Type 1 Envelope Immunogens Elicit Broad Cellular and Humoral Immunity in Rhesus Monkeys," Journal of Virology, vol. 79, No. 5, pp. 2956-2963 (2005).
Seaman et al, "Standardized Assessment of NAb Responses Elicited in Rhesus Monkeys Immunized with Single- or Multi-Clade HIV-1 Envelope Immunogens," Virology, vol. 367, pp. 175-186 (2007).
Sharma et al, "Cleavage-Independent HIV-1 Env Trimers Engineered As Soluble Native Spike Mimetics for Vaccines Design," Cell Reports, vol. 11, pp. 1-12 (2015).
Simek et al, "Human Immunodeficiency Virus Type 1 Elite Neutralizers: Individuals With Broad and Potent Neutralizing Activity Identified by Using a High-Throughput Neutralization Assay Together With an Analytical Selection Algorithm," Journal of Virology, vol. 83, No. 14, pp. 7337-7748 (2009).
Sok et al, "Promiscuous Glycan Site Recognition by Antibodies to the High-Mannose Patch of gp120 Broadens Neutralization of HIV," Science Translational Medicine, vol. 6, No. 236, pp. 236ra63 (May 14, 2014).
Spranger et al., "Quantifying Adenovirus-Neutralizing Antibodies by Luciferase Transgene Detection: Addressing Preexisting Immunity to Vaccine and Gene Therapy Vectors", J. Clin. Microbiol, vol. 41, No. 11, pp. 5046-5052 (2003).
Stamatatos et al, "Neutralizing Antibodies Generated During Natural HIV-1 Infection: Good News for an HIV-1 Vaccine?," Nature Medicine, vol. 15, No. 8, pp. 866-870 (2009).

(56) References Cited

OTHER PUBLICATIONS

Stickl, Smallpox Vaccination and it's Consequences: First Experiences with the Highly Attenuated Smallpox Vaccine "MVA", Preventive Medicine, vol. 3, pp. 97-101 (1974).
Tatsis et al., "A CD46-binding Chimpanzee Adenovirus Vector as a Vaccine Carrier", Molecular Therapy, vol. 15, No. 3, pp. 608-617 (2007).
Thompson et al., "DNA/MVA Vaccination of HIV-1 Infected Participants with Viral Suppression on Antiretroviral Therapy, Followed by Treatment Interruption: Elicitation of Immune Responses without Control of Re-Emergent Virus", PLOS One, vol. 11, No. 10, pp. 25 (Oct. 2016).
Thorner et al., "Age Dependence of Adenovirus-Specific Neutralizing Antibody Titer in Individuals From Sub-Saharan Africa", J. Clin. Microbiol, vol. 44, No. 10, pp. 3781-3783 (2006).
Thurmond et al., "Web-Based Design and Evaluation of T-cell Vaccine Candidates," Bioinformatics, vol. 24, No. 14, pp. 1639-1640 (2008).
Uchiyama, "Liquid Formulation for Antibody Drugs", Biochimica Biophysica, vol. 1844, pp. 2041-2052 (2014).
Unaids, "Report on the Global AIDS Epidemic", 198 pgs (2013).
Vaine et al, "Antibody Responses Elicited through Homologous or Heterologous Prime-Boost DNA and Protein Vaccinations Differ in Functional Activity and Avidity," Vaccine, vol. 28, No. 17, pp. 2999-3007 (2010).
Vaine et al, "Improved Induction of Antibodies Against Key Neutralizing Epitopes by Human Immunodeficiency Virus Type 1 gp120 DNA Prime-Protein Boost Vaccination Compared to gp120 Protein-Only Vaccination," Journal of Virology, vol. 82, No. 15, pp. 7369-7378 (Aug. 2008).
Vaine et al, "Profiles of Human Serum Antibody Responses Elicited by Three Leading HIV Vaccines Focusing on the Induction of Env-Specific Antibodies," PLoS One, vol. 5, No. 11, pp. e13916 (Nov. 2010).
Vogel et al, "The Majority of Neutralizing Abs in HIV-1-Infected Patients Recognize Linear V3 Loop Sequences," The Journal of Immunology, vol. 153, pp. 1895-1904 (1994).
Vogels et al., "Replication-Deficient Human Adenovirus Type 35 Vecotrs for Gene Transfer and Vaccination: Efficient Human Cell Infection and Bypass of Preexisting Adenovirus Immunity", J. Virol, vol. 77, No. 15, pp. 8263-8271 (2003).
Walker et al, "Broad and Potent Neutralizing Antibodies from an African Donor Reveal a New HIV-1 Vaccine Target," Science, vol. 326, No. 5950, pp. 285-289 (Oct. 9, 2009).
Walker et al, "Broad Neutralization Coverage of HIV by Multiple Highly Potent Antibodies," Nature, vol. 477, No. 7365, pp. 466-470 (Sep. 22, 2011).
Walker et al, "Toward an AIDS Vaccine," Science, vol. 320, pp. 760-764 (May 9, 2008).
Wang et al, "Cross-Subtype Antibody and Cellular Immune Responses Induced by a Polyvalent DNA Prime-Protein Boost HIV-1 Vaccine in Healthy Human Volunteers," Vaccine, vol. 26, No. 31, pp. 3947-3957 (Jul. 23, 2008).
Wang et al, "Enhanced Immunogenicity of gp120 Protein when Combined with Recombinant DNA Priming to Generate Antibodies that Neutralize the JR-FL Primary Isolate of Human Immunodeficiency Virus Type 1," Journal of Virology, vol. 79, No. 12, pp. 7933-7937 (Jun. 2005).
Wang et al, "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates from Subtypes A, B, C, D and E," Virology, vol. 350, No. 1, pp. 34-47 (2006).
Watkins et al, "Immune Escape by Human Immunodeficiency Virus Type 1 from Neutralizing Antibodies: Evidence for Multiple Pathways," Journal of Virology, vol. 67, No. 12, pp. 7493-7500 (Dec. 1993).
Wattanapitayakul et al, "Recent Developments in Gene Therapy for Cardiac Disease," Biomed & Pharmacother, vol. 54, No. 1, pp. 487-504 (2000).

Wiggan et al. "Novel Formulations Enhance the Thermal Stability of Live-Attenuated Flavivirus Vaccines," Vaccine, vol. 29, pp. 7456-7462 (2011).
Williams et al., "HIV-1 DNA Predicts Disease Progression and Post-Treatment Virological Control", eLlfe, vol. 3, 16 pgs (2014).
Wiznerowicz et al, "Harnessing HIV for Therapy, Basic Research and Biotechnology," Trends in Biotechnology, vol. 23, No. 1, pp. 42-47 (Jan. 2005).
Wu et al, "Rational Design of Envelope Identifies Broadly Neutralizing Human Monoclonal Antibodies to HIV-1," Science, vol. 329, No. 5993, pp. 856-861 (Aug. 13, 2010).
Wyatt et al, "The Antigenic Structure of the HIV gp120 Envelope Glycoprotein," Nature, vol. 393, pp. 705-711 (Jun. 18, 1998).
Yang et al, "Improved Elicitation of Neutralizing Antibodies Against Primary Human Immunodeficiency Viruses by Soluble Stabilized Envelope Glycoprotein Trimers," Journal of Virology, vol. 75, No. 3, pp. 1165-1171 (Feb. 2001).
Yang et al, "Modifications That Stabilize Human Immunodeficiency Virus Envelope Glycoprotein Trimers in Solution," Journal of Virology, vol. 74, No. 10, pp. 4746-4754 (2000).
Yang et al., "Highly Stable Trimers Formed by Human Immunodeficiency Virus Type 1 Envelope Glycoproteins Fused with the Trimeric Motif of T4 Bacteriophage Fibritin", J. Virol., vol. 76, No. 9, pp. 4634-4642 (2002).
Yasmeen et al, "Differential Binding of Neutralizing and Non-Neutralizing Antibodies to Native-Like Soluble HIV-1 Env Trimers, Uncleaved Env Proteins, and Monomeric Subunits," Retrovirology, vol. 11, No. 41 (2014).
Zhang et al, "Expression, Purification, and Characterization of Recombinant HIV gp140," Journal of Biological Chemistry, vol. 276, No. 43, pp. 39577-39585 (2001).
Zhang et al, "Extensively Cross-Reactive Anti-HIV-1 Neutralizing Antibodies Induced by gp140 Immunization," PNAS, vol. 104, No. 24, pp. 10193-10198 (2007).
Zhao et al, "Nanoparticle Vaccines," Vaccines, vol. 32, pp. 327-337 (2014).
Zhou et al, "Structural Basis for Broad and Potent Neutralization of HIV-1 by Antibody VRC01," Science, vol. 329, No. 5993, pp. 811-817 (Aug. 13, 2010).
"Endogenous Retrovirus Group K Member 25 Env Polyprotein", Database UNIPROT, Accession No. Q5GI17, 2 pages (Mar. 1, 2005).
"GCN4 Fusion Linker Peptide, Seq ID No. 3," Database Geneseq, Accession No. AEN61500, 1 page (Mar. 8, 2007).
"Recombinant Protein gp41 Heterologous Transmembrane Region, Seq ID1," Database Geneseq, Accession No. AUR74751, 1 page, (Mar. 19, 2009).
"Transmembrane Domain Peptide, Seq ID 14," Database Geneseq, Accession No. AEF06609, 1 page (Mar. 23, 2006).
Abbink et al, "Comparative Seroprevalence and Immunogenicity of Six Rare Serotype Recombinant Adenovirus Vaccine Vectors From Subgroups B and D," Journal of Virology, vol. 81, No. 9, pp. 4654-4663 (2007).
Abrahams et al, "Quantitating the Multiplicity of Infection with Human Immunodeficiency Virus Type 1 Subtype C Reveals a Non-Poisson Distribution of Transmitted Variants," Journal of Virology, vol. 83, No. 8, pp. 3556-3567 (Apr. 2009).
Abrahamyan et al, "The Cytoplasmic Tail Slows the Folding of Human Immunodeficiency Virus Type 1 Env from a late Prebundle Configuration into the Six-Helix Bundle", Journal of Virology, vol. 79, No. 1, pp. 106-115 (2005).
Achenbach et al., "Effect of Therapeutic Intensification Followed by HIV DNA Prime and rAd5 Boost Vaccination on HIV-specific Immunity and HIV Reservoir (EraMune 02): a Multicentre Randomised Clinical Trial", The Lancet, vol. 2, No. 3, pp. e82-e91 (Mar. 2015).
Altschul et al, "Gapped BLAST and PSI-BLAST: a new generation of protein database search programs," Nucleic Acids Research, vol. 25, No. 17, pp. 3389-3402 (1997).
Amanna et al, "Contributions of Humoral and Cellular Immunity to Vaccine-Induced Protection in Humans," Virology, vol. 411, No. 2, pp. 206-215 (2011).

(56) References Cited

OTHER PUBLICATIONS

Ambrosini et al., "Gene Transfer in Astrocytes: Comparison Between Different Delivering Methods and Expression of the HIV-1 Protein Nef.", J. Neurosci. Res., vol. 55, p. 569 (1999) (Abstract Only).
Baba et al, "Human Neutralizing Monoclonal Antibodies of the IgG1 Subtype Protect Against Mucosal Simian-Human Immunodeficiency Virus Infection," Nature Medicine, vol. 6, No. 2, pp. 200-206 (2000).
Baden et al., "First-in-human Evaluation of the Safety and Immunogenicity of a Recombinant Adenovirus Serotype 26 HIV-1 Env Vaccine (IPCAVD 001)", J. Infect. Dis., vol. 207, No. 2, pp. 240-247 (2013).
Baicu et al., "Acid-base Buffering in Organ Preservation Solutions as a Function of Temperature: New Parameters for Comparing Buffer Capacity and Effciency", Cryobiology, vol. 45, pp. 33-48 (2002).
Bale et al, "Covalent Linkage of HIV-1 Trimers to Synthetic Liposomes Elicits Improved B Cell and Antibody Responses," Journal of Virology, vol. 91, No. 16, pp. e00443-17 (2017).
Bangari et al., "Development of Nonhuman Adenoviruses as Vaccine Vectors", Vaccine, vol. 24, No. 7, pp. 849-26 (2006).
Barnett et al, "Development of V2-deleted trimeric envelope vaccine candidates from human immunodeficiency virus type 1 (HIV-1) subtypes B and C," Microbes Infect., vol. 7, vol. 14, pp. 1386-1391 (2005).
Barouch et al, "Mosaic HIV-1 Vaccines Expand the Breadth and Depth of Cellular Immune Responses in Rhesus Monkeys," Nat. Med., vol. 16, No. 3, pp. 319-323 (2010).
Barouch et al., "Characterization of Humoral and Cellular Immune Responses Elicited by a Recombinant Adenovirus Serotype 26 HIV-1 Env Vaccine in Healthy Adults (IPCAVD 001)", J. Infect. Dis, vol. 207, No. 2, pp. 248-256 (2013).
Barouch et al., "International Seroepidemiology of Adenovirus Serotypes 5, 36, 35 and 48 in Pediatric and Adult Populations", Vaccine, vol. 29: pp. 5203-5209 (2011).
Barouch et al., "Protective Efficacy of a Global HIV-1 Mosaic Vaccine against Heterologous SHIV Challenges in Rhesus Monkeys", Cell, vol. 155, pp. 531-539 (Oct. 2013).
Barouch et al., "Protective Efficacy of Adenovirus/Protein Vaccines Against SIV Challenges in Rhesus Monkeys", Science, vol. 349, No. 6245, pp. 320-324 (Jul. 2015).
Barouch, "Challenges in the Development of an HIV-1 Vaccine", Nature, vol. 455, No. 2, pp. 613-619 (2008).
Beddows et al, "A Comparative Immunogenicity Study in Rabbits of Disulfide-Stablized, Proteolytically Cleaved, Soluble Trimeric Human Immunodeficiency Virus Type 1 gp140, Trimeric Cleavage-Defective gp140 and Monomeric gp120," Virology, vol. 360, pp. 329-340 (2007).
Berger et al, "Chemokine Receptors as HIV-1 Coreceptors: Roles in Viral Entry, Tropism and Disease," Annu. Rev. Immunol., vol. 17, pp. 657-700 (1999).
Berman et al, "Comparison of the Immune Response to Recombinant gp120 in Humans and Chimpanzees," AIDS, vol. 8, pp. 591-601 (1994).
Binley et al "A Recombinant Human Immunodeficiency Virus Type 1 Envelope Glycoprotein Complex Stabilized by 6 an Intermolecular Disulfide Bond Between the gp120 and gp41 Subunits is an Antigenic Mimic of the Trimeric Virion-Associated Structure," Journal of Virology, vol. 74, No. 2, pp. 627-643 (Jan. 2000).
Blanchard et al., "Modified Vaccinia Virus Ankara Undergoes Limited Replication in Human Cells and Lacks Several Immunomodulatory Proteins: Implications for Use as a Human Vaccine", Journ. of Gen. Viro., vol. 79, pp. 1159-1167 (1998).
Blondelle et al., "Immunogenically Optimized Peptides Derived from Natural Mutants of HIV CTL Epitopes and Peptide Combinational Libraries", Biopolymers, vol. 90(5), pp. 683-694 (2008).
Bower et al, "Elicitation of Neutralizing Antibodies with DNA Vaccines Expressing Soluble Stabilized Human Immunodefiency Virus Type 1 Envelope Glycoprotein Trimers Conjugated to C3d", Journ. of Viro., vol. 78, No. 9, pp. 4710-4719 (May 2004).

Bower et al, "HIV-1 ENV gp 140 Trimers Elicit Neutralizing Antibodies Without Efficient Induction of Conformational Antibodies," Vaccine, vol. 24, pp. 5442-5451 (2006).
Buchbinder et al., Efficacy Assessment of a Cell-Mediated Immunity HIV-1 Vaccine (The Step Study): A Double-Blind, Randomised, Placebo-Controlled, Test-of-Concept Trial, Lancet, vol. 372 No. 9653, pp. 1881-1893 (2008).
Burke et al. "Neutralizing Antibody Responses to Subtype B and C Adjuvanted HIV Envelope Protein Vaccination in Rabbits," Virology, vol. 387, No. 1, pp. 147-156 (Apr. 2009).
Burton et al, "HIV Vaccine Design and the Neutralizing Antibody Problem," Nature Immunology, vol. 5, No. 3, pp. 233-236 (Mar. 2004).
Calarese et al, "Antibody Domain Exchange is an Immunological Solution to Carbohydrate Cluster Recognition," Science, vol. 300, No. 5628, pp. 2065-2071 (2003).
Carcelain et al., "Immune Interventions in HIV Infection", Immunol Rev., vol. 254, No. 1, pp. 355-371 (2013).
Cardoso et al, "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).
Cardoso et al, "Structural Basis of Enhanced Binding of Extended and Helically Constrained Peptide Epitopes of the Broadly Neutralizing HIV-1 Antibody 4E1 0," Journal of Molecular Biology, vol. 365, No. 5, pp. 1533-1544 (2007).
Carroll et al., "Host Range and Cytopathogenicity of the Highly Attenuated MVA Strain of Vaccinia Virus: Propagation and Generation of Recombinant Viruses in a Nonhuman Mammalian Cell Line", Virology, vol. 238, pp. 198-211 (1997).
Carrow et al, "High Prevalence of Antibodies to the gp120 V3 Regional Principal Neutralizing Determinant of HIV-1 MN in Sera from Africa and the Americas," Aids Research and Human Retroviruses, vol. 7, No. 10, pp. 831-838 (1991).
Catanzaro et al, "Phase I Clinical Evaluation of a Six-Plasmid Multiclade HIV-1 DNA Candidate Vaccine," Vaccine, vol. 25, No. 20, pp. 4085-4092 (2007).
Centlivre et al., "In HIV-1 Pathogenesis the Die is Cast During Primary Infections", AIDS, vol. 21, No. 1, pp. 1-11 (2007).
Checkley et al, "HIV-1 Envelope Glycoprotein Biosynthesis, Trafficking, and Incorporation," Journal of Molecular Biology, vol. 410, No. 4, pp. 582-608 (2011).
Chen et al, "Expression, Purification, and Characterization of gp160e, the Soluble, Trimeric Ectodomain of the Simian Immunodeficiency Virus Envelope Glycoprotein, gp160," The Journal of Biological Chemistry, vol. 275, No. 45, pp. 34946-34953 (Nov. 10, 2000).
Chen et al., A Chimeric Protein of Simian Immunodeficiency Virus Envelope Glycoprotein gp140 and *Escherichia coli* Asparatate Transcarbamoylase, J. Virol, vol. 78, No. 9, pp. 4508-4516 (2004).
Chen et al., "Adenovirus-Based Vaccines: Comparison of Vectors from Three Species of Adenoviridae", J. Virol, vol. 84, No. 20, pp. 10522-10532 (2010).
Chen et al., "Protection of Rhesus Macaques Against Disease Progression from Pathogenic SHIV-89.6PD by Vaccination with Phage-Displayed HIV-1 Epitopes", Nat. Med., vol. 7, No. 11, pp. 1225-1231 (2001).
Cho et al, "Polyvalent Envelope Glycoprotein Vaccine Elicits a Broader Neutralizing Antibody Response But is Unable to Provide Sterilizing Protection Against Heterologous Simian/Human Immunodeficiency Virus Infection in Pigtailed Macaques," Journal of Virology, vol. 75, No. 5, pp. 2224-2234 (Mar. 2001).
Clapp et al. "Vaccines with Aluminum-Containing Adjuvants: Optimizing Vaccine Efficacy and Thermal Stability", J. Pharm. Sci. vol. 100, No. 2: pp. 388-401 (2011).
Cohen et al, "Chimpanzee Adenovirus CV-68 Adapted as a Gene Delivery Vector Interacts with the Coxsackievirus and Adenovirus Receptor", J. Gen. Virol., vol. 83, pp. 151-155 (2002).
Havenga et al., "Novel Replication-Incompetent Adenoviral B-Group Vectors: High Vector Stability and Yield in PER. C6 Cells", Journ. of Gen Viro., vol. 87, pp. 2135-2143 (2006).
Haynes et al, "Immune-Correlates Analysis of an HIV-1 Vaccine Efficacy Trial," The New England Journal of Medicine, vol. 366, No. 14, pp. 1275-1286 (2012).

(56) References Cited

OTHER PUBLICATIONS

He et al, "Presenting Native-Like Trimeric HIV-1 Antigens With Self-Assembling Nanoparticles," Nature Communications, vol. 7, No. 1, pp. 1-15 (2016).

Hierholzer et al., "Adenoviruses from Patients with AIDS: A Plethora of Serotypes and a Description of Five New Serotypes of Subgenus D (types 43-47).", J. Infect. Dis., vol. 158, No. 4 pp. 804-813 (1988) (Abstract Only).

Hoganson et al., "Development of a Stable Adenoviral Vector Formulation", BioProcessing Journ., pp. 43-48 (Mar. 2002).

Huang et al, "Broad and Potent Neutralization of HIV-1 by a gp41-Specific Human Antibody," Nature, vol. 491, No. 7424, pp. 406-412 (2012).

Janes et al., "MRKAd5 HIV-1 Gag/Pol/Nef Vaccine-Induced T-cell Responses Inadequately Predict Distance of Breakthrough HIV-1 Sequences to the Vaccine or Viral Load", PLoS One, vol. 7, No. 8, pp. e43396 (2012).

Jeffs et al, "Expression and Characterization of Recombinant Oligomeric Envelope Glycoproteins Derived From Primary Isolates of HIV-1," Vaccine, vol. 22, No. 8, pp. 1032-1046 (2004).

Jin et al., "Stabilizing Formulations for Inhalable Powders of an Adenovirus 35-Vectored Tuberculosis (TB) Vaccine (AERAS-402)", Vaccine, vol. 28, No. 27, pp. 4369-4375 (2010).

Julien et al, "Asymmetric Recognition of the HIV-1 Trimer by Broadly Neutralizing Antibody PG9," Proceedings of the National Academy of Sciences of the United States of America, vol. 110, No. 11, pp. 4351-4356 (Mar. 12, 2013).

Julien et al, "Broadly Neutralizing Antibody PGT121 Allosterically Modulates CD4 Binding via Recognition of the HIV-1 gp120 V3 Base and Multiple Surrounding Glycans," PLOS Pathogens, vol. 9, No. 5, pp. e1003342 (May 2013).

Julien et al, "Design and Structure of Two HIV-1 Clade C SOSIP. 664 Trimers That Increase the Arsenal of Native-Like Env Immunogens," PNAS, vol. 112, No. 38, pp. 11947-11952 (2015).

Kamerzell et al., "Protein-Excipient Interactions: Mechanisms and Biophysical Characterization Applied to Protein Formulation Development", Advanced Drug Delivery Review, vol. 63, pp. 1118-1159 (2011).

Kang et al, "Structural and Immunogenicity Studies of a Cleaved, Stabilized Envelope Trimer Derived from Subtype A HIV-1," Vaccine, vol. 27, pp. 5120-5132 (2009).

Katlama et al., "Barriers to a Cure for HIV: New Ways to Target and Eradicate HIV-1 Reservoirs", The Lancet, vol. 381, No. 988., pp. 2109-2117 (Jun. 2013).

Kesavardhana et al, "Stabilizing the Native Trimer of HIV-1 Env by Destabilizing the Heterodimeric Interface of the gp41 Postfusion Six-Helix Bundle," Journal of Virology, vol. 88, No. 17, pp. 9590-9604 (2014).

Khoo et al., "Adenovirus Infections in Human Immunodeficiency Virus-Positive Patients: Clinical Features and Molecular Epidemiology", J. Infect. Dis, vol. 172, No. 3, pp. 629-637 (1995) (Abstract Only).

Kim et al., "Comparison of HIV Type 1 ADA gp120 Monomers Versus gp140 Trimers as Immunogens for the Induction of Neutralizing Antibodies," AIDS Research and Human Retroviruses, vol. 21, No. 1, pp. 58-67 (2005).

Kobinger et al, "Chimpanzee Adenovirus Vaccine Protects Against Zaire Ebola Virus", Virology, vol. 346, pp. 394-401 (2006).

Kochanek et al, "A New Adenoviral Vector: Replacement of All Viral Coding Sequences with 28 kb of DNA Independently Expressing Both Full-Length Dystrophin and Beta-Galactosidase," Proceedings of the National Academy of Sciences of the United States of America, vol. 93, No. 12, pp. 5731-5736 (Jun. 1996).

Kong et al, "Uncleaved Prefusion-Optimized gp140 Trimers Derived From Analysis of HIV-1 Envelope Metastability," Nature Communications, vol. 7, No. 1, pp. 1-15 (2016).

Kong et al., "Expanded Breadth of the T-Cell Response to Mosaic Human Immunodeficiency Virus Type 1 Envelope DNA Vaccination," J. Viral., vol. 83, No. 5, pp. 2201-2215 (2009).

Korber et al., "T-Cell Vaccine Strategies for Human Immunodeficiency Virus, The Virus with a Thousand Faces," J. Viral., vol. 83, No. 17, pp. 8300-8314 (2009).

Kothe et al, "Ancestral and Consensus Envelope Immunogens for HIV-1 Subtype C," Virology, vol. 352, No. 2, pp. 438-449 (2006).

Kothe et al, "Antigenicity and Immunogenicity of HIV-1 Consensus Subtype B Envelope Glycoproteins," Virology, vol. 360, No. 1, pp. 218-234 (Mar. 30, 2007).

Kovacs et al., "HIV-1 Envelope Trimer Elicits more Potent Neutralizing Antibody Responses than Monomeric gp120", Proc. Natl. Acac. Sci., vol. 109, No. 30, pp. 12111-12116 (2012).

Kuschner et al., "A Phase 3, Randomized, Double-Blind, Placebo-Controlled Study of the Safety and Efficacy of the Live, Oral Adenovirus Type 4 and Type 7 Vaccine, in U.S. Military Recruits", Vaccine, vol. 31(28), pp. 2963-2971 (2013).

Kushnir et al, "Virus-Like Particles As a Highly Efficient Vaccine Platform: Diversity of Targets and Production Systems and Advances in Clinical Development," Vaccine, vol. 31, pp. 58-83 (2012).

Kwon et al, "Crystal Structure, Conformational Fixation and Entry-Related Interactions of Mature Ligand-Free HIV-1 ENV," Nature Structural & Molecular Biology, vol. 22, No. 7, pp. 522-531 (2015).

Kwong et al, "Structure of an HIV gp120 Envelope Glycoprotein in Complex with the CD4 Receptor and a Neutralizing Human Antibody," Nature, vol. 393, No. 6686, pp. 648-659 (Jun. 18, 1998).

Lasaro et al., "New Insights on Adenovirus as Vaccine Vectors", Mol. Ther., vol. 17, No. 8, pp. 1333-1339 (2009).

Lee et al, "A Single Point Mutation in HIV-1 V3 Loop Alters the Immunogenic Properties of rgp120," Archives of Virology, vol. 145, pp. 2087-2103 (2000).

Lepe-Zuniga et al., "Toxicity of Light-Exposed Hepes Media", Journ. of Immun. Methods, vol. 103, pp. 145 (1987).

Letvin et al., "Potent, Protective Anti-HIV Immune Responses Generated by Bimodal HIV Envelope DNA Plus Protein Vaccination", Proc. Natl. Acad. Sci., vol. 94, pp. 9378-9383 (1997).

Levine, "Why Do We Not Yet Have a Human Immunodeficiency Virus Vaccine," J. Virol., vol. 82, No. 24, pp. 11998-12000 (Dec. 2008).

Li et al, "Broad HIV-1 Neutralization Mediated by CD4-Binding Site Antibodies," Nature Medicine, vol. 13, No. 9, pp. 1032-1039 (Sep. 2007).

Li et al, "Characterization of Antibody Responses Elicited by Human Immunodeficiency Virus Type 1 Primary Isolate Trimeric and Monomeric Envelope Glycoproteins in Selected Adjuvants," Journal of Virology, vol. 80, No. 3, pp. 1414-1426 (Feb. 2006).

Li et al, "Evidence for Potent Autologous Neutralizing Antibody Titers and Compact Envelopes in Early Infection with Subtype C Human Immunodeficiency Virus Type 1," Journal of Virology, vol. 80, No. 11, pp. 5211-5218 (Jun. 2006).

Li et al, "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).

Li et al, "Removal of a Single N-Linked Glycan in Human Immunodeficiency Virus Type 1 gp120 Results in an Enhanced Ability to Induce Neutralizing Antibody Responses," Journal of Virology, vol. 82, No. 2, pp. 638-651 (Jan. 2008).

Li et al., "Visualizing Antigen-Specific and Infected Cells in Situ Predicts Outcomes in Early Viral Infection", Science, vol. 323, No. 5922, pp. 1726-1729 (2009).

Lian et al., "Evaluation of Envelope Vaccines Derived from the South African Subtype C Human Immunodeficiency Virus Type 1 TV1 Strain," Journal of Virology, vol. 79, No. 21, pp. 13338-13349 (Nov. 2005).

Liao et al, "A Group M Consensus Envelope Glycoprotein Induces Antibodies That Neutralize Subsets of Subtype B and C HIV-1 Primary Viruses," Virology, vol. 353, No. 2, pp. 268-282 (Sep. 30, 2006).

Liao et al, "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 (Apr. 2013).

(56) References Cited

OTHER PUBLICATIONS

Liao et al, "Co-Evolution of a Broadly Neutralizing HIV-1 Antibody and Founder Virus," Nature, vol. 496, No. 7446, pp. 469-476 (Apr. 25, 2013).
Lin et al, "Designing Immunogens to Elicit Broadly Neutralizing Antibodies to the HIV-1 Envelope Glycoprotein," Current HIV Research, vol. 5, No. 6, pp. 514-541 (2007).
Liu et al., "Magnitude and Phenotype of Cellular Immune Responses Elicited by Recombinant Adenovirus Vectors and Heterologous Prime-Boost Regimens in Rhesus Monkeys", J. Viol., vol. 82, No. 10, pp. 4844-4852 (2008).
Liu et al., Immune Control of an SIV Challenge by a T-Cell-Based Vaccine in Rhesus Monkeys, Nature, vol. 457, No. 7225, pp. 87-91(2009).
Li et al, "Genetic and Neutralization Properties of Subtype C Human Immunodeficiency Virus Type 1 Molecular env Clones From Acute Early Heterosexually Acquired Infections in Southern Africa," Journal of Virology, vol. 80, No. 23, 11776-11790 (Dec. 2006).
Zigler et al., "Analysis of the Cytotoxic Effects of Light-Exposed Hepes-Containing Culture Medium", In Vitro Cell Dev. Biol., vol. 21, No. 5, pp. 282-287 (1985).
Zolla-Pazner et al, "Focusing the Immune Response on the V3 Loop, a Neutralizing Epitope of the HIV-1 gp210 Envelope," Virology, vol. 372, pp. 233-246 (2008).
Shu et al., "Efficient Boosting After Plasmid DNA or Recombinant Adenovirus Immunization with HIV-1 Vaccine Constructs", Vaccine, vol. 25, No. 8, pp. 1398-1408 (2007).
Muthumani et al., "HIV-1 Env DNA Vaccine plus PRotein Boost Delivered by EP Expands B- and T-Cell Responses and Neutralizing Phenotype in Vivo", PLOS One, vol. 8, No. 12, 12 pgs (Dec. 2013).
Barouch et al., "Accelerating HIV-1 Vaccine Efficacy Trials", Cell, vol. 159, No. 5, pp. 969-792 (Nov. 2014).
Schuitemaker, "Evaluation of lead HIV-1 Vaccine Regimen in APPROACH: Phase 1/2a study testing heterologous prime boost regimens using mosaic Ad26 and MVA vectors combined with Env protein", Jul. 24, 2017, Retrived from the Internet: https://www.avac.org/sites/default/files/u3/hiv-1_APPROACH.pdf, Retrived Nov. 29, 2018.
Cohen, "Did Merck's Failed HIV Vaccine Cause Harm?" Science, vol. 318, pp. 1048-1049 (2007).
Cohen, "Naked DNA Points Way to Vaccines," Science, vol. 259, pp. 1691-1692 (Mar. 1993).
Crooks et al, "A Comparative Immunogenicity Study of HIV-1 Virus-Like Particles Bearing Various Forms of Envelope Proteins, Particles Bearing No Envelope and Soluble Monomeric gp120," ScienceDirect, Virology vol. 366, pp. 245-262 (2007).
Davenport et al, "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107 (Jul. 2011).
De Gruijl et al., Intradermal Delivery of Adenoviral Type-35 Vectors Leads to High Efficiency Transduction of Mature, CD8+ T Cell-Stimulating Skin-Emigrated Dendritic Cells, J. Immunol, vol. 177, No. 4, pp. 2208-2215 (2006).
De Taeye et al, "Immunogenicity of Stabilized HIV-1 Envelope Trimers With Reduced Exposure of Non-Neutralizing Epitopes," Cell, vol. 163, pp. 1702-1715 (2015).
Derby et al, "Isolation and Characterization of Monoclonal Antibodies Elicited by Trimeric HIV-1 ENV gp140 Protein 14 Immunogens," Virology, vol. 366, pp. 433-445 (2007).
Desrosiers, "Prospects for an AIDS Vaccine", Nature Medicine, vol. 10, No. 3, pp. 221-223 (2004).
Dey et al, "Characterization of Human Immunodeficiency Virus Type 1 Monomeric and Trimeric gp120 Glycoproteins Stabilized in the CD4-Bound State: Antigenicity, Biophysics, and Immunogenicity," Journal of Virology, vol. 81, No. 11, pp. 5579-5593 (Jun. 2007).
Doores et al, "Antibody 2G12 Recognizes Di-Mannose Equivalently in Domain- and Nondomain-Exchanged Forms but Only Binds the HIV-1 Glycan Shield if Domain Exchanged," Journal of Virology, vol. 84, No. 20, pp. 10690-10699 (2010).
Doria-Rose et al, "Frequency and Phenotype of Human Immunodeficiency Virus Envelope-Specific B Cells from Patients with Broadly Cross-Neutralizing Antibodies," Journal of Virology, vol. 83, No. 1, pp. 188-199 (Jan. 2009).
Eglen et al, "The Use of AlphaScreen Technology in HTS: Current Status," Current Chemical Genomics, vol. 1, pp. 2-10 (2008).
Engelhardt et al, "Ablation of E2A in Recombinant Adenoviruses Improves Transgene Persistence and Decreases Inflammatory Response in Mouse Liver," Proceedings of the National Academy of Sciences of the United States of America, vol. 91, No. 13, pp. 6196-6200 (Jun. 1994).
Falkowska et al, "PGV04, an HIV-1 gp120 CD4 Binding Site Antibody, is Broad and Potent in Neutralization but Does Not Induce Conformational Changes Characteristic of CD4," Journal of Virology, vol. 86, No. 8, pp. 4394-4403 (2012).
Farina et al., "Replication-defective Vector Based on a Chimpanzee Adenovirus", J. Virol, vol. 75, No. 23, pp. 11603-11613 (2001).
Fiebig et al, "Neutralizing Antibodies Against Conserved Domains of p15E of Porcine Endogenous Retroviruses: Basis for a Vaccine for Xenotransplantation?" Virology, vol. 307, No. 2, pp. 406-413 (2003).
Fischer et al, "Identification of a Peptide Mimicking the Binding Pattern of an Antiphospholipid Antibody," Immunobiology, vol. 211, No. 9, pp. 695-699 (2006).
Fischer et al., "Coping with Viral Diversity in HIV vaccine Design: A Response to Nickle et al.," PLoS Comput Bioi., vol. 4, No. 1, pp. 175-179 (2008).
Fischer et al., "Polyvalent Vaccines for Optimal Coverage of Potential T-Cell Epitopes in Global HIV-1 Variants", Nat. Med., vol. 13, No. 1, pp. 100-106 (Jan. 2007).
Flynn et al., "Placebo-controlled phase 3 trial of a recombinant glycoprotein 120 vaccine to prevent HIV-1 infection",. J. Infect Dis, vol. 191, No. 5, pp. 654-665 (2005).
Freeman et al, "Crystal Structure of HIV-1 Primary Receptor CD4 in Complex with a Potent Antiviral Antibody," Structure, vol. 18, No. 12, pp. 1632-1641 (Dec. 8, 2010).
Frey et al, "A Fusion-Intermediate State of HIV-1 gp41 Targeted by Broadly Neutralizing Antibodies," Proceedings of the National Academy of Sciences of the United States of America, vol. 105, No. 10, pp. 3739-3744 (Mar. 11, 2008).
Fynan et al, "DNA Vaccines: Protective Immunizations by Parenteral, Mucosal, and Gene-Gun Inoculations," Proceedings of the National Academy of Sciences of the United States of America, vol. 90, No. 24, pp. 11478-11482 (Dec. 1993).
Gach et al., "HIV-1-Specific Antibody Response and Function after DNA Prime and Recombinant Adenovirus 5 Boost HIV Vaccine in HIV-Infected Subjects", PLOS One, vol. 11, No. 8, pp. 17 (Aug. 2016).
Gallo et al, "The HIV Env-mediated Fusion Reaction," Biochemics et Biophysica Acta, pp. 36-50 (2003).
Gallo, "The End or the Beginning of the Drive to an HIV-Preventive Vaccine: A View from over 20 Years", The Lancet, vol. 366, No. 9500, pp. 1894-1898 (Nov. 2005).
Gao et al, "A Comprehensive Panel of Near-Full-Length Clones and Reference Sequences for Non-Subtype B Isolates of Human Immunodeficiency Virus Type 1,"Journal of Virology, vol. 72, No. 7, pp. 5680-5698 (1998).
Gao et al, "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).
Gao et al, "Centralized HIV-1 Envelope Immunogens and Neutralizing Antibodies," Current HIV Research, vol. 5, No. 6, pp. 572-577 (2007).
Gao et al, "Molecular Cloning and Analysis of Functional Envelope Genes from Human Immunodeficiency Virus Type 1 Sequence Subtypes A through G" Journal of Virology, vol. 70, No. 3, pp. 1651-1667 (Mar. 1996).
Gaschen et al, "Diversity Consideration in HIV-1 Vaccine Selection," Science, vol. 296, No. 5577, pp. 2354-2360 (Jun. 28, 2002).

(56) References Cited

OTHER PUBLICATIONS

Genbank Accession No. AF286227.1, "HIV-1 strain 97Za012 from South Africa, complete genome." Accessed Jan. 6, 2016.
GenBank Accession No. KC769514. Retrieved on Dec. 30, 2014 (2 pages).
Georgiev et al, "Delineating Antibody Recognition in Polyclonal Sera from Patterns of HIV-1 Isolate Neutralization," Science, vol. 340, No. 6133, pp. 751-756 (2013).
Georgiev et al, "Single-Chain Soluble BG505.SOSIP gp140 Trimers As Structural and Antigenic Mimics of Mature Closed HIV-1 Env," Journal of Virology, vol. 89, pp. 5318-5329 (2015).
Gianella et al., "Effect of Early Antiretroviral Therapy During Primary HIV-1 Infection on Cell-Associated HIV-1 DNA and Plasma HIV-1 RNA", Antiviral Therapy, vol. 16, No. 4, pp. 535-545 (2011).
Girard et al., A Review of Vaccine Research and Development: The Human Immunodeficiency Virus (HIV), Vaccine, vol. 24, pp. 4062-4081 (2006).
Gomez-Roman et al., "An Adenovirus-Based HIV Subtype B Prime/Boost Vaccine Regimen Elicits Antibodies Mediating Broad Antibody-Dependent Cellular Cytotoxicity Against Non-Subtype B HIV Strains", J. Acquir. Immune Defic. Syndr., vol. 43, No. 3, pp. 270-277 (Nov. 2006).
Gotch et al., "Candidate Vaccines for Immunotherapy in HIV", HIV Medicine, vol. 2, pp. 260-265 (2001).
Goujard et al., "HIV-1 Control After Transient Antiretroviral Treatment Initiated in Primary Infection: Role of Patient Characteristics and Effect of Therapy", Antiviral Therapy, vol. 17, No. 6, pp. 1001-1009 (2012).
Graham et al, "Phase 1 Safety and Immunogenicity Evaluation of a Multiclade HIV-1 DNA Candidate Vaccine," The Journal of Infectious Diseases, vol. 194, No. 12, pp. 1650-1660 (Dec. 15, 2006).
Gray et al, "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).
Gray et al., "Safety and Efficacy of the HVTN 503/Phambili Study of a Clade-B-based HIV-1 Vaccine in South Africa: A Double-Blind, Randomised, Placebo-Controlled Test-of-Concept Phase 2b Study", Lancet Infect Dis, vol. 11, No. 7, pp. 507-515 (2011).
Grundner et al, "Analysis of the Neutralizing Antibody Response Elicited in Rabbits by Repeated Inoculation with Trimeric HIV-1 Envelope Glycoproteins," Virology, vol. 331, No. 1, pp. 33-46 (2005).
Guenaga et al, "Glycine Substitution At Helix-To-Coil Transitions Facilitates the Structural Determination of a Stabilized Subtype C HIV Envelope Glycoprotein," Immunity, vol. 46, pp. 792-803 (2017).
Gurwith et al, "Safety and Immunogenicity of an Oral, Replicating Adenovirus Serotype 4 Vector Vaccine for H5N1 Influenza: A Randomised, Double-Blind, Placebo-Controlled, Phase 1 Study", Lancet Infect Dis, vol. 13, No. 3, pp. 238-250 (2013).
Hamlyn et al., "Plasma HIV Viral Rebound Following Protocol-Indicated Cessation of ART Commenced in Primary and Chronic HIV Infection", PLOS One, vol. 7, No. 8, 8 pgs (Aug. 2012).
Hammer et al, "Efficacy Trial of a DNA/rAd5 HIV-1 Preventive Vaccine," The New England Journal of Medicine, vol. 369, No. 22, pp. 2083-2092 (Nov. 28, 2013).
Harris et al, "Trimeric HIV-1 Glycoprotein gp140 Immunogens and Native HIV-1 Envelope Glycoproteins Display the Same Closed and Open Quaternary Molecular Architectures," PNAS, vol. 108, No. 28, pp. 11440-11445 (2011).
Haslett et al., "Strong Human Immunodeficiency Virus (HIV)-Specific CD4+ T Cell Responses in a Cohort of Chronically Infected Patients are Associated with Interruptions in Anti-HIV Chemotherapy,"J. Infect. Dis, vol. 81, No. 4, pp. 1264-1272 (2000).
Johannes et al., "HIV-1-Specific antibody response and function after DNA Prima nd Recombinant Adenovirus 5 boost HIV Vaccine in HIV-infected subjects", PloS One, 2016, 11(8):pdf pp. 1-17.
Liu, J, et al. Magnitude and phenotype of cellular immune responses elicited by recombinant adenovirus vectors and heterologous prime-boost regimens in rhesus monkeys. J Virol, 2008. 82(10): p. 4844-4852.
Lore, K et al. Myeloid and plasmacytoid dendritic cells susceptible to recombinant adenovirus vectors and stimulate polyfunctional memory T cell responses. J. Immunol, 2007. 179(3): p. 1721-1729.
Li, Q. et al. Visualizing antigen-specific and infected cells in situ predicts outcomes in early viral infection. Science, 2009. 323(5922): p. 1726-1729.
Guyader, M., et al., 1987, Genome organization and transactivation of the human immunodeficiency virus type 2, Nature 326:662-669.
Franchini, G., and M. L. Bosch, 1989, Genetic relatedness of the human immunodeficiency viruses type 1 and 2 (HIV-1, HIV-2) and the simian immunodeficiency virus (SIV), Annal New York Acad. Sci. 554(1):81-87.

* cited by examiner

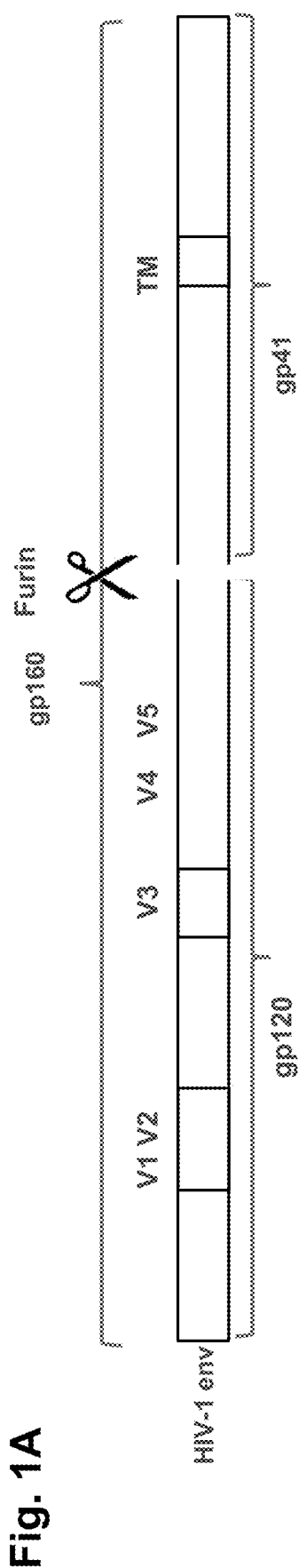
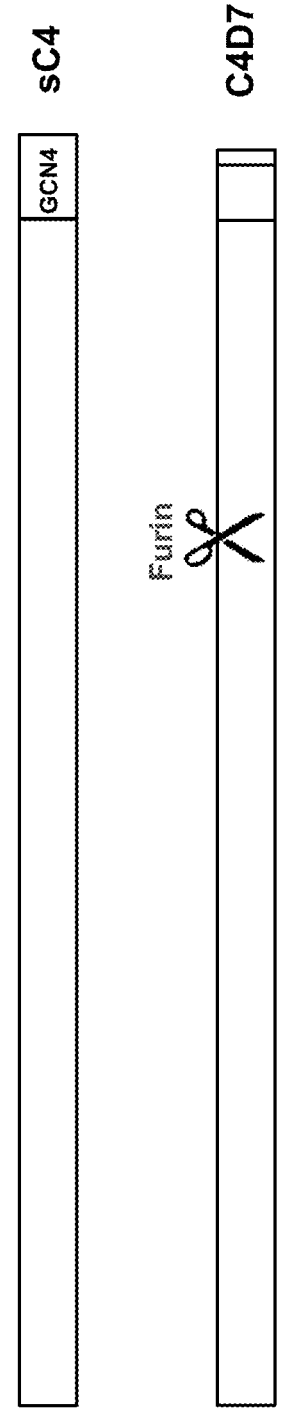
Fig. 1A
Fig. 1B
Fig. 1C

○ 3-valent
▣ 4-valent (C4D7)
△ 4-valent (sC4)
▼ control (Ad26.empty)

SEQUENCE LISTING

<160> NUMBER OF SEQ ID NOS: 37

<210> SEQ ID NO 1
<211> LENGTH: 500
<212> TYPE: PRT
<213> ORGANISM: Artificial Sequence
<220> FEATURE:
<223> OTHER INFORMATION: mos1Gag mosaic antigen sequence

<400> SEQUENCE: 1

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu Ala Glu Ala Met Ser

```
                355                 360                 365
Gln Val Thr Asn Ser Ala Thr Ile Met Met Gln Arg Gly Asn Phe Arg
            370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
                435                 440                 445

Leu Gln Asn Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln
            500

<210> SEQ ID NO 2
<211> LENGTH: 491
<212> TYPE: PRT
<213> ORGANISM: Artificial Sequence
<220> FEATURE:
<223> OTHER INFORMATION: mos2Gag mosaic antigen sequence

<400> SEQUENCE: 2

Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
                20                  25                  30

His Leu Val Trp Ala Ser Arg Glu Leu Glu Arg Phe Ala Leu Asn Pro
            35                  40                  45

Gly Leu Leu Glu Thr Ser Glu Gly Cys Lys Gln Ile Ile Lys Gln Leu
        50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Glu Gln Asn Lys Ser Gln
                100                 105                 110

Gln Lys Thr Gln Gln Ala Lys Glu Ala Asp Gly Lys Val Ser Gln Asn
            115                 120                 125

Tyr Pro Ile Val Gln Asn Leu Gln Gly Gln Met Val His Gln Pro Ile
        130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
```

```
                210               215               220
Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                    245                 250                 255

Asp Ile Tyr Lys Arg Trp Ile Ile Leu Gly Leu Asn Lys Ile Val Arg
                260                 265                 270

Met Tyr Ser Pro Thr Ser Ile Leu Asp Ile Lys Gln Gly Pro Lys Glu
                275                 280                 285

Pro Phe Arg Asp Tyr Val Asp Arg Phe Phe Lys Thr Leu Arg Ala Glu
                290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                    325                 330                 335

Gly Ala Thr Leu Glu Glu Met Met Thr Ala Cys Gln Gly Val Gly Gly
                340                 345                 350

Pro Ser His Lys Ala Arg Val Leu Ala Glu Ala Met Ser Gln Thr Asn
                355                 360                 365

Ser Thr Ile Leu Met Gln Arg Ser Asn Phe Lys Gly Ser Lys Arg Ile
370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                    405                 410                 415

Gln Met Lys Asp Cys Thr Glu Arg Gln Ala Asn Phe Leu Gly Lys Ile
                420                 425                 430

Trp Pro Ser His Lys Gly Arg Pro Gly Asn Phe Leu Gln Ser Arg Pro
                435                 440                 445

Glu Pro Thr Ala Pro Pro Ala Glu Ser Phe Arg Phe Glu Glu Thr Thr
                450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln
                485                 490

<210> SEQ ID NO 3
<211> LENGTH: 850
<212> TYPE: PRT
<213> ORGANISM: Artificial Sequence
<220> FEATURE:
<223> OTHER INFORMATION: mos1Pol mosaic antigen sequence

<400> SEQUENCE: 3

Met Ala Pro Ile Ser Pro Ile Glu Thr Val Pro Val Lys Leu Lys Pro
1               5                   10                  15

Gly Met Asp Gly Pro Arg Val Lys Gln Trp Pro Leu Thr Glu Glu Lys
                20                  25                  30

Ile Lys Ala Leu Thr Ala Ile Cys Glu Glu Met Glu Lys Glu Gly Lys
            35                  40                  45

Ile Thr Lys Ile Gly Pro Glu Asn Pro Tyr Asn Thr Pro Val Phe Ala
        50                  55                  60

Ile Lys Lys Lys Asp Ser Thr Lys Trp Arg Lys Leu Val Asp Phe Arg
65                  70                  75                  80

Glu Leu Asn Lys Arg Thr Gln Asp Phe Trp Glu Val Gln Leu Gly Ile
```

```
                    85                  90                  95
Pro His Pro Ala Gly Leu Lys Lys Lys Ser Val Thr Val Leu Ala
                100                 105                 110

Val Gly Asp Ala Tyr Phe Ser Val Pro Leu Asp Glu Gly Phe Arg Lys
                115                 120                 125

Tyr Thr Ala Phe Thr Ile Pro Ser Thr Asn Asn Glu Thr Pro Gly Ile
                130                 135                 140

Arg Tyr Gln Tyr Asn Val Leu Pro Gln Gly Trp Lys Gly Ser Pro Ala
145                 150                 155                 160

Ile Phe Gln Cys Ser Met Thr Arg Ile Leu Glu Pro Phe Arg Ala Lys
                165                 170                 175

Asn Pro Glu Ile Val Ile Tyr Gln Tyr Met Ala Ala Leu Tyr Val Gly
                180                 185                 190

Ser Asp Leu Glu Ile Gly Gln His Arg Ala Lys Ile Glu Glu Leu Arg
                195                 200                 205

Glu His Leu Leu Lys Trp Gly Phe Thr Thr Pro Asp Lys Lys His Gln
                210                 215                 220

Lys Glu Pro Pro Phe Leu Trp Met Gly Tyr Glu Leu His Pro Asp Lys
225                 230                 235                 240

Trp Thr Val Gln Pro Ile Gln Leu Pro Glu Lys Asp Ser Trp Thr Val
                245                 250                 255

Asn Asp Ile Gln Lys Leu Val Gly Lys Leu Asn Trp Ala Ser Gln Ile
                260                 265                 270

Tyr Pro Gly Ile Lys Val Arg Gln Leu Cys Lys Leu Leu Arg Gly Ala
                275                 280                 285

Lys Ala Leu Thr Asp Ile Val Pro Leu Thr Glu Glu Ala Glu Leu Glu
290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly His
                325                 330                 335

Asp Gln Trp Thr Tyr Gln Ile Tyr Gln Glu Pro Phe Lys Asn Leu Lys
                340                 345                 350

Thr Gly Lys Tyr Ala Lys Met Arg Thr Ala His Thr Asn Asp Val Lys
                355                 360                 365

Gln Leu Thr Glu Ala Val Gln Lys Ile Ala Met Glu Ser Ile Val Ile
                370                 375                 380

Trp Gly Lys Thr Pro Lys Phe Arg Leu Pro Ile Gln Lys Glu Thr Trp
385                 390                 395                 400

Glu Thr Trp Trp Thr Asp Tyr Trp Gln Ala Thr Trp Ile Pro Glu Trp
                405                 410                 415

Glu Phe Val Asn Thr Pro Pro Leu Val Lys Leu Trp Tyr Gln Leu Glu
                420                 425                 430

Lys Asp Pro Ile Ala Gly Val Glu Thr Phe Tyr Val Ala Gly Ala Ala
                435                 440                 445

Asn Arg Glu Thr Lys Leu Gly Lys Ala Gly Tyr Val Thr Asp Arg Gly
                450                 455                 460

Arg Gln Lys Ile Val Ser Leu Thr Glu Thr Thr Asn Gln Lys Thr Ala
465                 470                 475                 480

Leu Gln Ala Ile Tyr Leu Ala Leu Gln Asp Ser Gly Ser Glu Val Asn
                485                 490                 495

Ile Val Thr Ala Ser Gln Tyr Ala Leu Gly Ile Ile Gln Ala Gln Pro
                500                 505                 510
```

Asp Lys Ser Glu Ser Glu Leu Val Asn Gln Ile Ile Glu Gln Leu Ile
            515                 520                 525

Lys Lys Glu Arg Val Tyr Leu Ser Trp Val Pro Ala His Lys Gly Ile
        530                 535                 540

Gly Gly Asn Glu Gln Val Asp Lys Leu Val Ser Ser Gly Ile Arg Lys
545                 550                 555                 560

Val Leu Phe Leu Asp Gly Ile Asp Lys Ala Gln Glu Glu His Glu Lys
                565                 570                 575

Tyr His Ser Asn Trp Arg Ala Met Ala Ser Asp Phe Asn Leu Pro Pro
            580                 585                 590

Val Val Ala Lys Glu Ile Val Ala Ser Cys Asp Gln Cys Gln Leu Lys
        595                 600                 605

Gly Glu Ala Met His Gly Gln Val Asp Cys Ser Pro Gly Ile Trp Gln
610                 615                 620

Leu Ala Cys Thr His Leu Glu Gly Lys Ile Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Ile Leu Lys Leu Ala Gly Arg Trp Pro Val
            660                 665                 670

Lys Val Ile His Thr Ala Asn Gly Ser Asn Phe Thr Ser Ala Ala Val
        675                 680                 685

Lys Ala Ala Cys Trp Trp Ala Gly Ile Gln Gln Glu Phe Gly Ile Pro
690                 695                 700

Tyr Asn Pro Gln Ser Gln Gly Val Val Ala Ser Met Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Gly Tyr Ser Ala Gly Glu Arg Ile Ile Asp Ile Ile Ala Thr
        755                 760                 765

Asp Ile Gln Thr Lys Glu Leu Gln Lys Gln Ile Ile Lys Ile Gln Asn
770                 775                 780

Phe Arg Val Tyr Tyr Arg Asp Ser Arg Asp Pro Ile Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Val Lys Ile Ile Lys Asp
            820                 825                 830

Tyr Gly Lys Gln Met Ala Gly Ala Asp Cys Val Ala Gly Arg Gln Asp
        835                 840                 845

Glu Asp
    850

<210> SEQ ID NO 4
<211> LENGTH: 850
<212> TYPE: PRT
<213> ORGANISM: Artificial Sequence
<220> FEATURE:
<223> OTHER INFORMATION: mos2Pol mosaic antigen sequence

<400> SEQUENCE: 4

Met Ala Pro Ile Ser Pro Ile Glu Thr Val Pro Val Lys Leu Lys Pro
1               5                   10                  15

```
Gly Met Asp Gly Pro Lys Val Lys Gln Trp Pro Leu Thr Glu Glu Lys
             20                  25                  30

Ile Lys Ala Leu Val Glu Ile Cys Thr Glu Met Glu Lys Glu Gly Lys
         35                  40                  45

Ile Ser Lys Ile Gly Pro Glu Asn Pro Tyr Asn Thr Pro Ile Phe Ala
 50                  55                  60

Ile Lys Lys Lys Asp Ser Thr Lys Trp Arg Lys Leu Val Asp Phe Arg
 65                  70                  75                  80

Glu Leu Asn Lys Arg Thr Gln Asp Phe Trp Glu Val Gln Leu Gly Ile
                 85                  90                  95

Pro His Pro Ala Gly Leu Lys Lys Lys Ser Val Thr Val Leu Ala
                100                 105                 110

Val Gly Asp Ala Tyr Phe Ser Val Pro Leu Asp Glu Asp Phe Arg Lys
         115                 120                 125

Tyr Thr Ala Phe Thr Ile Pro Ser Ile Asn Asn Glu Thr Pro Gly Ile
130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Arg Lys Gln
                165                 170                 175

Asn Pro Asp Ile Val Ile Tyr Gln Tyr Met Ala Ala Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Phe Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Gln Lys Leu Val Gly Lys Leu Asn Trp Ala Ser Gln Ile
            260                 265                 270

Tyr Ala Gly Ile Lys Val Lys Gln Leu Cys Lys Leu Leu Arg Gly Thr
        275                 280                 285

Lys Ala Leu Thr Glu Val Val Pro Leu Thr Glu Glu Ala Glu Leu Glu
290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
            340                 345                 350

Thr Gly Lys Tyr Ala Arg Met Arg Gly Ala His Thr Asn Asp Val Lys
        355                 360                 365

Gln Leu Thr Glu Ala Val Gln Lys Ile Ala Thr Glu Ser Ile Val Ile
    370                 375                 380

Trp Gly Lys Thr Pro Lys Phe Lys Leu Pro Ile Gln Lys Glu Thr Trp
385                 390                 395                 400

Glu Ala Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
            420                 425                 430
```

-continued

```
Lys Glu Pro Ile Val Gly Ala Glu Thr Phe Tyr Val Ala Gly Ala Ala
            435                 440                 445

Asn Arg Glu Thr Lys Leu Gly Lys Ala Gly Tyr Val Thr Asp Arg Gly
450                 455                 460

Arg Gln Lys Val Val Ser Leu Thr Asp Thr Thr Asn Gln Lys Thr Ala
465                 470                 475                 480

Leu Gln Ala Ile His Leu Ala Leu Gln Asp Ser Gly Leu Glu Val Asn
                485                 490                 495

Ile Val Thr Ala Ser Gln Tyr Ala Leu Gly Ile Ile Gln Ala Gln Pro
                500                 505                 510

Asp Lys Ser Glu Ser Glu Leu Val Ser Gln Ile Glu Gln Leu Ile
            515                 520                 525

Lys Lys Glu Lys Val Tyr Leu Ala Trp Val Pro Ala His Lys Gly Ile
530                 535                 540

Gly Gly Asn Glu Gln Val Asp Lys Leu Val Ser Arg Gly Ile Arg Lys
545                 550                 555                 560

Val Leu Phe Leu Asp Gly Ile Asp Lys Ala Gln Glu Glu His Glu Lys
                565                 570                 575

Tyr His Ser Asn Trp Arg Ala Met Ala Ser Glu Phe Asn Leu Pro Pro
                580                 585                 590

Ile Val Ala Lys Glu Ile Val Ala Ser Cys Asp Lys Cys Gln Leu Lys
                595                 600                 605

Gly Glu Ala Ile His Gly Gln Val Asp Cys Ser Pro Gly Ile Trp Gln
            610                 615                 620

Leu Ala Cys Thr His Leu Glu Gly Lys Val Ile Leu Val Ala Val His
625                 630                 635                 640

Val Ala Ser Gly Tyr Ile Glu Ala Glu Val Ile Pro Ala Glu Thr Gly
                645                 650                 655

Gln Glu Thr Ala Tyr Phe Leu Leu Lys Leu Ala Gly Arg Trp Pro Val
            660                 665                 670

Lys Thr Ile His Thr Ala Asn Gly Ser Asn Phe Thr Ser Ala Thr Val
            675                 680                 685

Lys Ala Ala Cys Trp Trp Ala Gly Ile Lys Gln Glu Phe Gly Ile Pro
690                 695                 700

Tyr Asn Pro Gln Ser Gln Gly Val Val Ala Ser Ile Asn Lys Glu Leu
705                 710                 715                 720

Lys Lys Ile Ile Gly Gln Val Arg Asp Gln Ala Glu His Leu Lys Thr
                725                 730                 735

Ala Val Gln Met Ala Val Phe Ile His Asn Phe Lys Arg Lys Gly Gly
            740                 745                 750

Ile Gly Glu Tyr Ser Ala Gly Glu Arg Ile Val Asp Ile Ile Ala Ser
            755                 760                 765

Asp Ile Gln Thr Lys Glu Leu Gln Lys Gln Ile Thr Lys Ile Gln Asn
770                 775                 780

Phe Arg Val Tyr Tyr Arg Asp Ser Arg Asp Pro Leu Trp Lys Gly Pro
785                 790                 795                 800

Ala Lys Leu Leu Trp Lys Gly Glu Gly Ala Val Val Ile Gln Asp Asn
                805                 810                 815

Ser Asp Ile Lys Val Val Pro Arg Arg Lys Ala Lys Ile Ile Arg Asp
            820                 825                 830

Tyr Gly Lys Gln Met Ala Gly Asp Asp Cys Val Ala Ser Arg Gln Asp
            835                 840                 845

Glu Asp
```

-continued

```
                850

<210> SEQ ID NO 5
<211> LENGTH: 685
<212> TYPE: PRT
<213> ORGANISM: Artificial Sequence
<220> FEATURE:
<223> OTHER INFORMATION: mos1Env mosaic antigen sequence

<400> SEQUENCE: 5

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Asn Ala Thr Asn Thr
    130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
            180                 185                 190

Asn Thr Asn Tyr Arg Leu Ile Ser Cys Asn Thr Ser Val Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
        275                 280                 285

Ile Met Val Gln Leu Asn Val Ser Val Glu Ile Asn Cys Thr Arg Pro
    290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
```

```
                355                 360                 365
Ser Gly Gly Asp Pro Glu Ile Val Met His Ser Phe Asn Cys Gly Gly
            370                 375                 380
Glu Phe Phe Tyr Cys Asn Ser Thr Lys Leu Phe Asn Ser Thr Trp Thr
385                 390                 395                 400
Trp Asn Asn Ser Thr Trp Asn Asn Thr Lys Arg Ser Asn Asp Thr Glu
                405                 410                 415
Glu His Ile Thr Leu Pro Cys Arg Ile Lys Gln Ile Ile Asn Met Trp
            420                 425                 430
Gln Glu Val Gly Lys Ala Met Tyr Ala Pro Pro Ile Arg Gly Gln Ile
        435                 440                 445
Arg Cys Ser Ser Asn Ile Thr Gly Leu Leu Leu Thr Arg Asp Gly Gly
            450                 455                 460
Asn Asp Thr Ser Gly Thr Glu Ile Phe Arg Pro Gly Gly Gly Asp Met
465                 470                 475                 480
Arg Asp Asn Trp Arg Ser Glu Leu Tyr Lys Tyr Lys Val Val Lys Ile
                485                 490                 495
Glu Pro Leu Gly Val Ala Pro Thr Lys Ala Lys Arg Arg Val Val Gln
            500                 505                 510
Ser Glu Lys Ser Ala Val Gly Ile Gly Ala Val Phe Leu Gly Phe Leu
        515                 520                 525
Gly Ala Ala Gly Ser Thr Met Gly Ala Ala Ser Met Thr Leu Thr Val
    530                 535                 540
Gln Ala Arg Leu Leu Leu Ser Gly Ile Val Gln Gln Gln Asn Asn Leu
545                 550                 555                 560
Leu Arg Ala Ile Glu Ala Gln Gln His Leu Leu Gln Leu Thr Val Trp
                565                 570                 575
Gly Ile Lys Gln Leu Gln Ala Arg Val Leu Ala Val Glu Arg Tyr Leu
            580                 585                 590
Lys Asp Gln Gln Leu Leu Gly Ile Trp Gly Cys Ser Gly Lys Leu Ile
        595                 600                 605
Cys Thr Thr Thr Val Pro Trp Asn Ala Ser Trp Ser Asn Lys Ser Leu
    610                 615                 620
Asp Lys Ile Trp Asn Asn Met Thr Trp Met Glu Trp Glu Arg Glu Ile
625                 630                 635                 640
Asn Asn Tyr Thr Ser Leu Ile Tyr Thr Leu Ile Glu Glu Ser Gln Asn
                645                 650                 655
Gln Gln Glu Lys Asn Glu Gln Glu Leu Leu Glu Leu Asp Lys Trp Ala
            660                 665                 670
Ser Leu Trp Asn Trp Phe Asp Ile Ser Asn Trp Leu Trp
        675                 680                 685

<210> SEQ ID NO 6
<211> LENGTH: 684
<212> TYPE: PRT
<213> ORGANISM: Artificial Sequence
<220> FEATURE:
<223> OTHER INFORMATION: mos2Env mosaic antigen sequence

<400> SEQUENCE: 6

Met Arg Val Arg Gly Ile Gln Arg Asn Trp Pro Gln Trp Trp Ile Trp
1               5                   10                  15
Gly Ile Leu Gly Phe Trp Met Ile Ile Cys Arg Val Met Gly Asn
                20                  25                  30
Leu Trp Val Thr Val Tyr Tyr Gly Val Pro Val Trp Lys Glu Ala Lys
```

```
                35                  40                  45
Thr Thr Leu Phe Cys Ala Ser Asp Ala Lys Ala Tyr Glu Lys Glu Val
 50                  55                  60

His Asn Val Trp Ala Thr His Ala Cys Val Pro Thr Asp Pro Asn Pro
 65                  70                  75                  80

Gln Glu Met Val Leu Glu Asn Val Thr Glu Asn Phe Asn Met Trp Lys
                     85                  90                  95

Asn Asp Met Val Asp Gln Met His Glu Asp Ile Ile Arg Leu Trp Asp
                100                 105                 110

Gln Ser Leu Lys Pro Cys Val Lys Leu Thr Pro Leu Cys Val Thr Leu
            115                 120                 125

Glu Cys Arg Asn Val Arg Asn Val Ser Ser Asn Gly Thr Tyr Asn Ile
130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Asn Phe
        355                 360                 365

Thr Ser Ser Gly Gly Asp Leu Glu Ile Thr Thr His Ser Phe Asn
370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
            420                 425                 430

Arg Ala Met Tyr Ala Pro Pro Ile Ala Gly Asn Ile Thr Cys Arg Ser
        435                 440                 445

Asn Ile Thr Gly Leu Leu Leu Thr Arg Asp Gly Gly Ser Asn Asn Gly
450                 455                 460
```

Val Pro Asn Asp Thr Glu Thr Phe Arg Pro Gly Gly Asp Met Arg
465                 470                 475                 480

Asn Asn Trp Arg Ser Glu Leu Tyr Lys Tyr Lys Val Val Glu Val Lys
            485                 490                 495

Pro Leu Gly Val Ala Pro Thr Glu Ala Lys Arg Arg Val Val Glu Ser
                500                 505                 510

Glu Lys Ser Ala Val Gly Ile Gly Ala Val Phe Leu Gly Ile Leu Gly
            515                 520                 525

Ala Ala Gly Ser Thr Met Gly Ala Ala Ser Ile Thr Leu Thr Val Gln
530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
            595                 600                 605

Thr Thr Ala Val Pro Trp Asn Thr Ser Trp Ser Asn Lys Ser Gln Thr
610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Ser Gln Asn Gln
                645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp
            675                 680

<210> SEQ ID NO 7
<211> LENGTH: 708
<212> TYPE: PRT
<213> ORGANISM: Artificial Sequence
<220> FEATURE:
<223> OTHER INFORMATION: stabilized clade C gp140 trimer:
    C97ZA012-gp140-foldon with cleavage mutations

<400> SEQUENCE: 7

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Glu Asn
            20                  25                  30

Leu Trp Val Gly Asn Met Trp Val Thr Val Tyr Tyr Gly Val Pro Val
        35                  40                  45

Trp Thr Asp Ala Lys Thr Thr Leu Phe Cys Ala Ser Asp Thr Lys Ala
50                  55                  60

Tyr Asp Arg Glu Val His Asn Val Trp Ala Thr His Ala Cys Val Pro
65                  70                  75                  80

Thr Asp Pro Asn Pro Gln Glu Ile Val Leu Glu Asn Val Thr Glu Asn
                85                  90                  95

Phe Asn Met Trp Lys Asn Asp Met Val Asp Gln Met His Glu Asp Ile
            100                 105                 110

Ile Ser Leu Trp Asp Gln Ser Leu Lys Pro Cys Val Lys Leu Thr Pro
        115                 120                 125

Leu Cys Val Thr Leu His Cys Thr Asn Ala Thr Phe Lys Asn Asn Val

```
                130             135             140
Thr Asn Asp Met Asn Lys Glu Ile Arg Asn Cys Ser Phe Asn Thr Thr
145                 150                 155                 160
Thr Glu Ile Arg Asp Lys Lys Gln Gln Gly Tyr Ala Leu Phe Tyr Arg
                165                 170                 175
Pro Asp Ile Val Leu Lys Glu Asn Arg Asn Asn Ser Asn Asn Ser
                180                 185                 190
Glu Tyr Ile Leu Ile Asn Cys Asn Ala Ser Thr Ile Thr Gln Ala Cys
                195                 200                 205
Pro Lys Val Asn Phe Asp Pro Ile Pro Ile His Tyr Cys Ala Pro Ala
                210                 215                 220
Gly Tyr Ala Ile Leu Lys Cys Asn Asn Lys Thr Phe Ser Gly Lys Gly
225                 230                 235                 240
Pro Cys Asn Asn Val Ser Thr Val Gln Cys Thr His Gly Ile Lys Pro
                245                 250                 255
Val Val Ser Thr Gln Leu Leu Leu Asn Gly Ser Leu Ala Glu Lys Glu
                260                 265                 270
Ile Ile Ile Arg Ser Glu Asn Leu Thr Asp Asn Val Lys Thr Ile Ile
                275                 280                 285
Val His Leu Asn Lys Ser Val Glu Ile Val Cys Thr Arg Pro Asn Asn
                290                 295                 300
Asn Thr Arg Lys Ser Met Arg Ile Gly Pro Gly Gln Thr Phe Tyr Ala
305                 310                 315                 320
Thr Gly Asp Ile Ile Gly Asp Ile Arg Gln Ala Tyr Cys Asn Ile Ser
                325                 330                 335
Gly Ser Lys Trp Asn Glu Thr Leu Lys Arg Val Lys Glu Lys Leu Gln
                340                 345                 350
Glu Asn Tyr Asn Asn Lys Thr Ile Lys Phe Ala Pro Ser Ser Gly
                355                 360                 365
Gly Asp Leu Glu Ile Thr Thr His Ser Phe Asn Cys Arg Gly Glu Phe
                370                 375                 380
Phe Tyr Cys Asn Thr Thr Arg Leu Phe Asn Asn Asn Ala Thr Glu Asp
385                 390                 395                 400
Glu Thr Ile Thr Leu Pro Cys Arg Ile Lys Gln Ile Ile Asn Met Trp
                405                 410                 415
Gln Gly Val Gly Arg Ala Met Tyr Ala Pro Pro Ile Ala Gly Asn Ile
                420                 425                 430
Thr Cys Lys Ser Asn Ile Thr Gly Leu Leu Leu Val Arg Asp Gly Gly
                435                 440                 445
Glu Asp Asn Lys Thr Glu Glu Ile Phe Arg Pro Gly Gly Gly Asn Met
450                 455                 460
Lys Asp Asn Trp Arg Ser Glu Leu Tyr Lys Tyr Lys Val Ile Glu Leu
465                 470                 475                 480
Lys Pro Leu Gly Ile Ala Pro Thr Gly Ala Lys Glu Arg Val Val Glu
                485                 490                 495
Arg Glu Glu Arg Ala Val Gly Ile Gly Ala Val Phe Leu Gly Phe Leu
                500                 505                 510
Gly Ala Ala Gly Ser Thr Met Gly Ala Ala Ser Leu Thr Leu Thr Val
                515                 520                 525
Gln Ala Arg Gln Leu Leu Ser Ser Ile Val Gln Gln Ser Asn Leu
530                 535                 540
Leu Arg Ala Ile Glu Ala Gln Gln His Met Leu Gln Leu Thr Val Trp
545                 550                 555                 560
```

```
Gly Ile Lys Gln Leu Gln Thr Arg Val Leu Ala Ile Glu Arg Tyr Leu
            565                 570                 575

Lys Asp Gln Gln Leu Leu Gly Ile Trp Gly Cys Ser Gly Lys Leu Ile
            580                 585                 590

Cys Thr Thr Asn Val Pro Trp Asn Ser Ser Trp Ser Asn Lys Ser Gln
            595                 600                 605

Thr Asp Ile Trp Asn Asn Met Thr Trp Met Glu Trp Asp Arg Glu Ile
            610                 615                 620

Ser Asn Tyr Thr Asp Thr Ile Tyr Arg Leu Leu Glu Asp Ser Gln Thr
625                 630                 635                 640

Gln Gln Glu Lys Asn Glu Lys Asp Leu Leu Ala Leu Asp Ser Trp Lys
            645                 650                 655

Asn Leu Trp Ser Trp Phe Asp Ile Ser Asn Trp Leu Trp Tyr Ile Lys
            660                 665                 670

Ser Arg Ile Glu Gly Arg Gly Ser Gly Gly Tyr Ile Pro Glu Ala Pro
            675                 680                 685

Arg Asp Gly Gln Ala Tyr Val Arg Lys Asp Gly Glu Trp Val Leu Leu
            690                 695                 700

Ser Thr Phe Leu
705

<210> SEQ ID NO 8
<211> LENGTH: 625
<212> TYPE: PRT
<213> ORGANISM: Artificial Sequence
<220> FEATURE:
<223> OTHER INFORMATION: C4 fragment: gp120-truncated gp41 without
      signal peptide and transmembrane domain

<400> SEQUENCE: 8

Met Gly Asn Leu Trp Val Thr Val Tyr Tyr Gly Val Pro Val Trp Lys
1               5                   10                  15

Asp Ala Lys Thr Thr Leu Phe Cys Ala Ser Asp Ala Lys Ala Tyr Glu
            20                  25                  30

Lys Glu Val His Asn Val Trp Ala Thr His Ala Cys Val Pro Thr Asp
            35                  40                  45

Pro Asn Pro Gln Glu Ile Val Leu Gly Asn Val Thr Glu Asn Phe Asn
        50                  55                  60

Met Trp Lys Asn Asp Met Val Asp Gln Met His Glu Asp Ile Ile Ser
65                  70                  75                  80

Leu Trp Asp Ala Ser Leu Glu Pro Cys Val Lys Leu Thr Pro Leu Cys
            85                  90                  95

Val Thr Leu Asn Cys Arg Asn Val Arg Asn Val Ser Ser Asn Gly Thr
            100                 105                 110

Tyr Asn Ile Ile His Asn Glu Thr Tyr Lys Glu Met Lys Asn Cys Ser
            115                 120                 125

Phe Asn Ala Thr Thr Val Val Glu Asp Arg Lys Gln Lys Val His Ala
        130                 135                 140

Leu Phe Tyr Arg Leu Asp Ile Val Pro Leu Asp Glu Asn Asn Ser Ser
145                 150                 155                 160

Glu Lys Ser Ser Glu Asn Ser Ser Glu Tyr Tyr Arg Leu Ile Asn Cys
            165                 170                 175

Asn Thr Ser Ala Ile Thr Gln Ala Cys Pro Lys Val Ser Phe Asp Pro
            180                 185                 190

Ile Pro Ile His Tyr Cys Ala Pro Ala Gly Tyr Ala Ile Leu Lys Cys
```

```
            195                 200                 205
Asn Asn Lys Thr Phe Asn Gly Thr Gly Pro Cys Asn Asn Val Ser Thr
210                 215                 220
Val Gln Cys Thr His Gly Ile Lys Pro Val Val Ser Thr Gln Leu Leu
225                 230                 235                 240
Leu Asn Gly Ser Leu Ala Glu Glu Ile Ile Arg Ser Glu Asn
            245                 250                 255
Leu Thr Asn Asn Ala Lys Thr Ile Ile Val His Leu Asn Glu Thr Val
            260                 265                 270
Asn Ile Thr Cys Thr Arg Pro Asn Asn Asn Thr Arg Lys Ser Ile Arg
        275                 280                 285
Ile Gly Pro Gly Gln Thr Phe Tyr Ala Thr Gly Asp Ile Ile Gly Asp
        290                 295                 300
Ile Arg Gln Ala His Cys Asn Leu Ser Arg Asp Gly Trp Asn Lys Thr
305                 310                 315                 320
Leu Gln Gly Val Lys Lys Leu Ala Glu His Phe Pro Asn Lys Thr
                325                 330                 335
Ile Lys Phe Ala Pro His Ser Gly Gly Asp Leu Glu Ile Thr Thr His
            340                 345                 350
Thr Phe Asn Cys Arg Gly Glu Phe Phe Tyr Cys Asn Thr Ser Asn Leu
        355                 360                 365
Phe Asn Glu Ser Asn Ile Glu Arg Asn Asp Ser Ile Ile Thr Leu Pro
370                 375                 380
Cys Arg Ile Lys Gln Ile Ile Asn Met Trp Gln Glu Val Gly Arg Ala
385                 390                 395                 400
Ile Tyr Ala Pro Pro Ile Ala Gly Asn Ile Thr Cys Arg Ser Asn Ile
                405                 410                 415
Thr Gly Leu Leu Leu Thr Arg Asp Gly Gly Ser Asn Asn Gly Val Pro
            420                 425                 430
Asn Asp Thr Glu Thr Phe Arg Pro Gly Gly Gly Asp Met Arg Asn Asn
        435                 440                 445
Trp Arg Ser Glu Leu Tyr Lys Tyr Lys Val Val Glu Val Lys Pro Leu
    450                 455                 460
Gly Val Ala Pro Thr Glu Ala Lys Arg Arg Val Val Glu Arg Glu Lys
465                 470                 475                 480
Arg Ala Val Gly Ile Gly Ala Val Phe Leu Gly Ile Leu Gly Ala Ala
                485                 490                 495
Gly Ser Thr Met Gly Ala Ala Ser Ile Thr Leu Thr Val Gln Ala Arg
                500                 505                 510
Gln Leu Leu Ser Gly Ile Val Gln Gln Gln Ser Asn Leu Leu Arg Ala
            515                 520                 525
Ile Glu Ala Gln Gln His Met Leu Gln Leu Thr Val Trp Gly Ile Lys
            530                 535                 540
Gln Leu Gln Thr Arg Val Leu Ala Ile Glu Arg Tyr Leu Gln Asp Gln
545                 550                 555                 560
Gln Leu Leu Gly Leu Trp Gly Cys Ser Gly Lys Leu Ile Cys Thr Thr
            565                 570                 575
Ala Val Pro Trp Asn Thr Ser Trp Ser Asn Lys Ser Gln Thr Asp Ile
            580                 585                 590
Trp Asp Asn Met Thr Trp Met Gln Trp Asp Lys Glu Ile Gly Asn Tyr
        595                 600                 605
Thr Gly Glu Ile Tyr Arg Leu Leu Glu Glu Ser Gln Asn Gln Gln Glu
610                 615                 620
```

Lys
625

<210> SEQ ID NO 9
<211> LENGTH: 29
<212> TYPE: PRT
<213> ORGANISM: Artificial Sequence
<220> FEATURE:
<223> OTHER INFORMATION: signal sequence

<400> SEQUENCE: 9

Met Arg Val Arg Gly Met Leu Arg Asn Trp Gln Gln Trp Trp Ile Trp
1               5                   10                  15

Ser Ser Leu Gly Phe Trp Met Leu Met Ile Tyr Ser Val
            20                  25

<210> SEQ ID NO 10
<211> LENGTH: 29
<212> TYPE: PRT
<213> ORGANISM: Artificial Sequence
<220> FEATURE:
<223> OTHER INFORMATION: signal sequence

<400> SEQUENCE: 10

Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala
            20                  25

<210> SEQ ID NO 11
<211> LENGTH: 29
<212> TYPE: PRT
<213> ORGANISM: Artificial Sequence
<220> FEATURE:
<223> OTHER INFORMATION: signal sequence

<400> SEQUENCE: 11

Met Arg Val Arg Gly Ile Gln Arg Asn Trp Pro Gln Trp Trp Ile Trp
1               5                   10                  15

Gly Ile Leu Gly Phe Trp Met Ile Ile Ile Cys Arg Val
            20                  25

<210> SEQ ID NO 12
<211> LENGTH: 29
<212> TYPE: PRT
<213> ORGANISM: Artificial Sequence
<220> FEATURE:
<223> OTHER INFORMATION: signal sequence

<400> SEQUENCE: 12

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala
            20                  25

<210> SEQ ID NO 13
<211> LENGTH: 22
<212> TYPE: PRT
<213> ORGANISM: Artificial Sequence
<220> FEATURE:
<223> OTHER INFORMATION: transmembrane domain

<400> SEQUENCE: 13

Ile Phe Ile Met Ile Val Gly Gly Leu Ile Gly Leu Arg Ile Ile Phe

```
              1               5                  10                  15

Ala Val Leu Ser Ile Val
            20

<210> SEQ ID NO 14
<211> LENGTH: 7
<212> TYPE: PRT
<213> ORGANISM: Artificial Sequence
<220> FEATURE:
<223> OTHER INFORMATION: truncated cytoplasmic region

<400> SEQUENCE: 14

Asn Arg Val Arg Gln Gly Tyr
1               5

<210> SEQ ID NO 15
<211> LENGTH: 32
<212> TYPE: PRT
<213> ORGANISM: Artificial Sequence
<220> FEATURE:
<223> OTHER INFORMATION: GCN4 trimerization domain

<400> SEQUENCE: 15

Met Lys Gln Ile Glu Asp Lys Ile Glu Glu Ile Leu Ser Lys Ile Tyr
1               5                  10                  15

His Ile Glu Asn Glu Ile Ala Arg Ile Lys Lys Leu Ile Gly Glu Val
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: foldon trimerization domain

<400> SEQUENCE: 16

Gly Ser Gly Gly Tyr Ile Pro Glu Ala Pro Arg Asp Gly Gln Ala Tyr
1               5                  10                  15

Val Arg Lys Asp Gly Glu Trp Val Leu Leu Ser Thr Phe Leu
            20                  25                  30

<210> SEQ ID NO 17
<211> LENGTH: 862
<212> TYPE: PRT
<213> ORGANISM: Artificial Sequence
<220> FEATURE:
<223> OTHER INFORMATION: C4 sequence

<400> SEQUENCE: 17

Met Arg Val Arg Gly Met Leu Arg Asn Trp Gln Gln Trp Trp Ile Trp
1               5                  10                  15

Ser Ser Leu Gly Phe Trp Met Leu Met Ile Tyr Ser Val Met Gly Asn
            20                  25                  30

Leu Trp Val Thr Val Tyr Tyr Gly Val Pro Val Trp Lys Asp Ala Lys
            35                  40                  45

Thr Thr Leu Phe Cys Ala Ser Asp Ala Lys Ala Tyr Glu Lys Glu Val
        50                  55                  60

His Asn Val Trp Ala Thr His Ala Cys Val Pro Thr Asp Pro Asn Pro
65                  70                  75                  80

Gln Glu Ile Val Leu Gly Asn Val Thr Glu Asn Phe Asn Met Trp Lys
                85                  90                  95

Asn Asp Met Val Asp Gln Met His Glu Asp Ile Ile Ser Leu Trp Asp
```

```
                100             105              110
Ala Ser Leu Glu Pro Cys Val Lys Leu Thr Pro Leu Cys Val Thr Leu
        115                 120                 125
Asn Cys Arg Asn Val Arg Asn Val Ser Ser Asn Gly Thr Tyr Asn Ile
        130                 135             140
Ile His Asn Glu Thr Tyr Lys Glu Met Lys Asn Cys Ser Phe Asn Ala
145                 150                 155                 160
Thr Thr Val Val Glu Asp Arg Lys Gln Lys Val His Ala Leu Phe Tyr
                165                 170                 175
Arg Leu Asp Ile Val Pro Leu Asp Glu Asn Asn Ser Ser Glu Lys Ser
            180                 185                 190
Ser Glu Asn Ser Ser Glu Tyr Tyr Arg Leu Ile Asn Cys Asn Thr Ser
        195                 200                 205
Ala Ile Thr Gln Ala Cys Pro Lys Val Ser Phe Asp Pro Ile Pro Ile
        210                 215                 220
His Tyr Cys Ala Pro Ala Gly Tyr Ala Ile Leu Lys Cys Asn Asn Lys
225                 230                 235                 240
Thr Phe Asn Gly Thr Gly Pro Cys Asn Asn Val Ser Thr Val Gln Cys
                245                 250                 255
Thr His Gly Ile Lys Pro Val Val Ser Thr Gln Leu Leu Leu Asn Gly
            260                 265                 270
Ser Leu Ala Glu Glu Glu Ile Ile Ile Arg Ser Glu Asn Leu Thr Asn
        275                 280                 285
Asn Ala Lys Thr Ile Ile Val His Leu Asn Glu Thr Val Asn Ile Thr
        290                 295                 300
Cys Thr Arg Pro Asn Asn Asn Thr Arg Lys Ser Ile Arg Ile Gly Pro
305                 310                 315                 320
Gly Gln Thr Phe Tyr Ala Thr Gly Asp Ile Ile Gly Asp Ile Arg Gln
                325                 330                 335
Ala His Cys Asn Leu Ser Arg Asp Gly Trp Asn Lys Thr Leu Gln Gly
            340                 345                 350
Val Lys Lys Lys Leu Ala Glu His Phe Pro Asn Lys Thr Ile Lys Phe
        355                 360                 365
Ala Pro His Ser Gly Gly Asp Leu Glu Ile Thr Thr His Thr Phe Asn
        370                 375                 380
Cys Arg Gly Glu Phe Phe Tyr Cys Asn Thr Ser Asn Leu Phe Asn Glu
385                 390                 395                 400
Ser Asn Ile Glu Arg Asn Asp Ser Ile Ile Thr Leu Pro Cys Arg Ile
                405                 410                 415
Lys Gln Ile Ile Asn Met Trp Gln Glu Val Gly Arg Ala Ile Tyr Ala
            420                 425                 430
Pro Pro Ile Ala Gly Asn Ile Thr Cys Arg Ser Asn Ile Thr Gly Leu
        435                 440                 445
Leu Leu Thr Arg Asp Gly Gly Ser Asn Asn Gly Val Pro Asn Asp Thr
        450                 455                 460
Glu Thr Phe Arg Pro Gly Gly Gly Asp Met Arg Asn Asn Trp Arg Ser
465                 470                 475                 480
Glu Leu Tyr Lys Tyr Lys Val Val Glu Val Lys Pro Leu Gly Val Ala
                485                 490                 495
Pro Thr Glu Ala Lys Arg Arg Val Val Glu Arg Glu Lys Arg Ala Val
            500                 505                 510
Gly Ile Gly Ala Val Phe Leu Gly Ile Leu Gly Ala Ala Gly Ser Thr
        515                 520                 525
```

```
Met Gly Ala Ala Ser Ile Thr Leu Thr Val Gln Ala Arg Gln Leu Leu
            530                 535                 540

Ser Gly Ile Val Gln Gln Ser Asn Leu Leu Arg Ala Ile Glu Ala
545                 550                 555                 560

Gln Gln His Met Leu Gln Leu Thr Val Trp Gly Ile Lys Gln Leu Gln
                565                 570                 575

Thr Arg Val Leu Ala Ile Glu Arg Tyr Leu Gln Asp Gln Gln Leu Leu
            580                 585                 590

Gly Leu Trp Gly Cys Ser Gly Lys Leu Ile Cys Thr Thr Ala Val Pro
        595                 600                 605

Trp Asn Thr Ser Trp Ser Asn Lys Ser Gln Thr Asp Ile Trp Asp Asn
610                 615                 620

Met Thr Trp Met Gln Trp Asp Lys Glu Ile Gly Asn Tyr Thr Gly Glu
625                 630                 635                 640

Ile Tyr Arg Leu Leu Glu Glu Ser Gln Asn Gln Gln Glu Lys Asn Glu
                645                 650                 655

Lys Asp Leu Leu Ala Leu Asp Ser Trp Asn Asn Leu Trp Asn Trp Phe
            660                 665                 670

Ser Ile Ser Lys Trp Leu Trp Tyr Ile Lys Ile Phe Ile Met Ile Val
        675                 680                 685

Gly Gly Leu Ile Gly Leu Arg Ile Ile Phe Ala Val Leu Ser Ile Val
690                 695                 700

Asn Arg Val Arg Gln Gly Tyr Ser Pro Leu Ser Leu Gln Thr Leu Thr
705                 710                 715                 720

Gln Asn Pro Gly Gly Leu Asp Arg Leu Gly Arg Ile Glu Glu Glu Gly
                725                 730                 735

Gly Glu Gln Asp Lys Asp Arg Ser Ile Arg Leu Val Asn Gly Phe Phe
            740                 745                 750

Ala Leu Phe Trp Asp Asp Leu Arg Ser Leu Cys Leu Phe Ser Tyr His
        755                 760                 765

Arg Leu Arg Asp Phe Ile Leu Ile Val Ala Arg Ala Val Glu Leu Leu
770                 775                 780

Gly Arg Ser Ser Leu Arg Gly Leu Gln Arg Gly Trp Glu Ile Leu Lys
785                 790                 795                 800

Tyr Leu Gly Ser Leu Leu Gln Tyr Trp Gly Leu Glu Leu Lys Lys Ser
                805                 810                 815

Ala Ile Asn Leu Leu Asp Thr Ile Ala Ile Ala Val Ala Glu Gly Thr
            820                 825                 830

Asp Arg Ile Ile Glu Leu Ile Gln Arg Ile Cys Arg Ala Ile Cys Asn
        835                 840                 845

Ile Pro Arg Arg Ile Arg Gln Gly Phe Glu Ala Ala Leu Gln
    850                 855                 860

<210> SEQ ID NO 18
<211> LENGTH: 711
<212> TYPE: PRT
<213> ORGANISM: Artificial Sequence
<220> FEATURE:
<223> OTHER INFORMATION: C4D7 sequence

<400> SEQUENCE: 18

Met Arg Val Arg Gly Met Leu Arg Asn Trp Gln Gln Trp Trp Ile Trp
1               5                   10                  15

Ser Ser Leu Gly Phe Trp Met Leu Met Ile Tyr Ser Val Met Gly Asn
                20                  25                  30
```

```
Leu Trp Val Thr Val Tyr Tyr Gly Val Pro Val Trp Lys Asp Ala Lys
         35                  40                  45

Thr Thr Leu Phe Cys Ala Ser Asp Ala Lys Ala Tyr Glu Lys Glu Val
         50                  55                  60

His Asn Val Trp Ala Thr His Ala Cys Val Pro Thr Asp Pro Asn Pro
 65              70                  75                  80

Gln Glu Ile Val Leu Gly Asn Val Thr Glu Asn Phe Asn Met Trp Lys
                 85                  90                  95

Asn Asp Met Val Asp Gln Met His Glu Asp Ile Ile Ser Leu Trp Asp
             100                 105                 110

Ala Ser Leu Glu Pro Cys Val Lys Leu Thr Pro Leu Cys Val Thr Leu
         115                 120                 125

Asn Cys Arg Asn Val Arg Asn Val Ser Ser Asn Gly Thr Tyr Asn Ile
         130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                 165                 170                 175

Arg Leu Asp Ile Val Pro Leu Asp Glu Asn Asn Ser Ser Glu Lys Ser
             180                 185                 190

Ser Glu Asn Ser Ser Glu Tyr Tyr Arg Leu Ile Asn Cys Asn Thr Ser
         195                 200                 205

Ala Ile Thr Gln Ala Cys Pro Lys Val Ser Phe Asp Pro Ile Pro Ile
         210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                 245                 250                 255

Thr His Gly Ile Lys Pro Val Val Ser Thr Gln Leu Leu Leu Asn Gly
             260                 265                 270

Ser Leu Ala Glu Glu Glu Ile Ile Arg Ser Glu Asn Leu Thr Asn
         275                 280                 285

Asn Ala Lys Thr Ile Ile Val His Leu Asn Glu Thr Val Asn Ile Thr
         290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                 325                 330                 335

Ala His Cys Asn Leu Ser Arg Asp Gly Trp Asn Lys Thr Leu Gln Gly
             340                 345                 350

Val Lys Lys Lys Leu Ala Glu His Phe Pro Asn Lys Thr Ile Lys Phe
         355                 360                 365

Ala Pro His Ser Gly Gly Asp Leu Glu Ile Thr Thr His Thr Phe Asn
         370                 375                 380

Cys Arg Gly Glu Phe Phe Tyr Cys Asn Thr Ser Asn Leu Phe Asn Glu
385                 390                 395                 400

Ser Asn Ile Glu Arg Asn Asp Ser Ile Ile Thr Leu Pro Cys Arg Ile
                 405                 410                 415

Lys Gln Ile Ile Asn Met Trp Gln Glu Val Gly Arg Ala Ile Tyr Ala
             420                 425                 430

Pro Pro Ile Ala Gly Asn Ile Thr Cys Arg Ser Asn Ile Thr Gly Leu
         435                 440                 445
```

Leu Leu Thr Arg Asp Gly Gly Ser Asn Asn Gly Val Pro Asn Asp Thr
450                 455                 460

Glu Thr Phe Arg Pro Gly Gly Gly Asp Met Arg Asn Asn Trp Arg Ser
465                 470                 475                 480

Glu Leu Tyr Lys Tyr Lys Val Val Glu Val Lys Pro Leu Gly Val Ala
            485                 490                 495

Pro Thr Glu Ala Lys Arg Arg Val Val Glu Arg Glu Lys Arg Ala Val
                500                 505                 510

Gly Ile Gly Ala Val Phe Leu Gly Ile Leu Gly Ala Ala Gly Ser Thr
        515                 520                 525

Met Gly Ala Ala Ser Ile Thr Leu Thr Val Gln Ala Arg Gln Leu Leu
530                 535                 540

Ser Gly Ile Val Gln Gln Gln Ser Asn Leu Leu Arg Ala Ile Glu Ala
545                 550                 555                 560

Gln Gln His Met Leu Gln Leu Thr Val Trp Gly Ile Lys Gln Leu Gln
            565                 570                 575

Thr Arg Val Leu Ala Ile Glu Arg Tyr Leu Gln Asp Gln Gln Leu Leu
                580                 585                 590

Gly Leu Trp Gly Cys Ser Gly Lys Leu Ile Cys Thr Thr Ala Val Pro
        595                 600                 605

Trp Asn Thr Ser Trp Ser Asn Lys Ser Gln Thr Asp Ile Trp Asp Asn
610                 615                 620

Met Thr Trp Met Gln Trp Asp Lys Glu Ile Gly Asn Tyr Thr Gly Glu
625                 630                 635                 640

Ile Tyr Arg Leu Leu Glu Glu Ser Gln Asn Gln Gln Glu Lys Asn Glu
            645                 650                 655

Lys Asp Leu Leu Ala Leu Asp Ser Trp Asn Asn Leu Trp Asn Trp Phe
                660                 665                 670

Ser Ile Ser Lys Trp Leu Trp Tyr Ile Lys Ile Phe Ile Met Ile Val
        675                 680                 685

Gly Gly Leu Ile Gly Leu Arg Ile Ile Phe Ala Val Leu Ser Ile Val
            690                 695                 700

Asn Arg Val Arg Gln Gly Tyr
705                 710

<210> SEQ ID NO 19
<211> LENGTH: 704
<212> TYPE: PRT
<213> ORGANISM: Artificial Sequence
<220> FEATURE:
<223> OTHER INFORMATION: sC4 sequence

<400> SEQUENCE: 19

Met Arg Val Arg Gly Met Leu Arg Asn Trp Gln Gln Trp Trp Ile Trp
1               5                   10                  15

Ser Ser Leu Gly Phe Trp Met Leu Met Ile Tyr Ser Val Met Gly Asn
                20                  25                  30

Leu Trp Val Thr Val Tyr Tyr Gly Val Pro Val Trp Lys Asp Ala Lys
            35                  40                  45

Thr Thr Leu Phe Cys Ala Ser Asp Ala Lys Ala Tyr Glu Lys Glu Val
50                  55                  60

His Asn Val Trp Ala Thr His Ala Cys Val Pro Thr Asp Pro Asn Pro
65                  70                  75                  80

Gln Glu Ile Val Leu Gly Asn Val Thr Glu Asn Phe Asn Met Trp Lys
                85                  90                  95

```
Asn Asp Met Val Asp Gln Met His Glu Asp Ile Ile Ser Leu Trp Asp
            100                 105                 110
Ala Ser Leu Glu Pro Cys Val Lys Leu Thr Pro Leu Cys Val Thr Leu
        115                 120                 125
Asn Cys Arg Asn Val Arg Asn Val Ser Ser Asn Gly Thr Tyr Asn Ile
    130                 135                 140
Ile His Asn Glu Thr Tyr Lys Glu Met Lys Asn Cys Ser Phe Asn Ala
145                 150                 155                 160
Thr Thr Val Val Glu Asp Arg Lys Gln Lys Val His Ala Leu Phe Tyr
                165                 170                 175
Arg Leu Asp Ile Val Pro Leu Asp Glu Asn Asn Ser Ser Glu Lys Ser
            180                 185                 190
Ser Glu Asn Ser Ser Glu Tyr Tyr Arg Leu Ile Asn Cys Asn Thr Ser
        195                 200                 205
Ala Ile Thr Gln Ala Cys Pro Lys Val Ser Phe Asp Pro Ile Pro Ile
    210                 215                 220
His Tyr Cys Ala Pro Ala Gly Tyr Ala Ile Leu Lys Cys Asn Asn Lys
225                 230                 235                 240
Thr Phe Asn Gly Thr Gly Pro Cys Asn Asn Val Ser Thr Val Gln Cys
                245                 250                 255
Thr His Gly Ile Lys Pro Val Val Ser Thr Gln Leu Leu Leu Asn Gly
            260                 265                 270
Ser Leu Ala Glu Glu Glu Ile Ile Arg Ser Glu Asn Leu Thr Asn
        275                 280                 285
Asn Ala Lys Thr Ile Ile Val His Leu Asn Glu Thr Val Asn Ile Thr
    290                 295                 300
Cys Thr Arg Pro Asn Asn Asn Thr Arg Lys Ser Ile Arg Ile Gly Pro
305                 310                 315                 320
Gly Gln Thr Phe Tyr Ala Thr Gly Asp Ile Ile Gly Asp Ile Arg Gln
                325                 330                 335
Ala His Cys Asn Leu Ser Arg Asp Gly Trp Asn Lys Thr Leu Gln Gly
            340                 345                 350
Val Lys Lys Lys Leu Ala Glu His Phe Pro Asn Lys Thr Ile Lys Phe
        355                 360                 365
Ala Pro His Ser Gly Gly Asp Leu Glu Ile Thr Thr His Thr Phe Asn
    370                 375                 380
Cys Arg Gly Glu Phe Phe Tyr Cys Asn Thr Ser Asn Leu Phe Asn Glu
385                 390                 395                 400
Ser Asn Ile Glu Arg Asn Asp Ser Ile Ile Thr Leu Pro Cys Arg Ile
                405                 410                 415
Lys Gln Ile Ile Asn Met Trp Gln Glu Val Gly Arg Ala Ile Tyr Ala
            420                 425                 430
Pro Pro Ile Ala Gly Asn Ile Thr Cys Arg Ser Asn Ile Thr Gly Leu
        435                 440                 445
Leu Leu Thr Arg Asp Gly Gly Ser Asn Asn Gly Val Pro Asn Asp Thr
    450                 455                 460
Glu Thr Phe Arg Pro Gly Gly Asp Met Arg Asn Asn Trp Arg Ser
465                 470                 475                 480
Glu Leu Tyr Lys Tyr Lys Val Val Glu Val Lys Pro Leu Gly Val Ala
                485                 490                 495
Pro Thr Glu Ala Lys Arg Arg Val Val Glu Arg Glu Arg Ala Val
            500                 505                 510
Gly Ile Gly Ala Val Phe Leu Gly Ile Leu Gly Ala Ala Gly Ser Thr
```

```
                515                 520                 525
Met Gly Ala Ala Ser Ile Thr Leu Thr Val Gln Ala Arg Gln Leu Leu
    530                 535                 540

Ser Gly Ile Val Gln Gln Ser Asn Leu Leu Arg Ala Ile Glu Ala
545                 550                 555                 560

Gln Gln His Met Leu Gln Leu Thr Val Trp Gly Ile Lys Gln Leu Gln
                565                 570                 575

Thr Arg Val Leu Ala Ile Glu Arg Tyr Leu Gln Asp Gln Gln Leu Leu
            580                 585                 590

Gly Leu Trp Gly Cys Ser Gly Lys Leu Ile Cys Thr Thr Ala Val Pro
                595                 600                 605

Trp Asn Thr Ser Trp Ser Asn Lys Ser Gln Thr Asp Ile Trp Asp Asn
            610                 615                 620

Met Thr Trp Met Gln Trp Asp Lys Glu Ile Gly Asn Tyr Thr Gly Glu
625                 630                 635                 640

Ile Tyr Arg Leu Leu Glu Glu Ser Gln Asn Gln Gln Glu Lys Met Lys
                645                 650                 655

Gln Ile Glu Asp Lys Ile Glu Glu Ile Leu Ser Lys Ile Tyr His Ile
            660                 665                 670

Glu Asn Glu Ile Ala Arg Ile Lys Lys Leu Ile Gly Glu Val Gly Ser
            675                 680                 685

Gly Ala Pro Thr Lys Ala Lys Arg Arg Val Val Gln Arg Glu Lys Arg
        690                 695                 700

<210> SEQ ID NO 20
<211> LENGTH: 4050
<212> TYPE: DNA
<213> ORGANISM: Artificial Sequence
<220> FEATURE:
<223> OTHER INFORMATION: nucleotide sequence encoding mos1GagPol

<400> SEQUENCE: 20
atgggagcca gagccagcgt gctgtccgga ggggagctgg accgctggga gaagatcagg      60
ctgaggcctg gagggaagaa gaagtacagg ctgaagcaca tcgtgtgggc cagcagagag     120
ctggaacggt ttgccgtgaa ccctggcctg ctggaaacca gcgagggctg taggcagatt     180
ctgggacagc tgcagcccag cctgcagaca ggcagcgagg aactgcggag cctgtacaac     240
accgtggcca ccctgtactg cgtgcaccag cggatcgaga tcaaggacac caagaagcc      300 ctggaaaaga tcgaggaaga gcagaacaag agcaagaaga agcccagca ggctgccgct      360 gacacaggca cagcagcca ggtgtcccag aactacccca tcgtgcagaa catccaggga     420
cagatggtgc accaggccat cagccctcgg accctgaacg cctgggtgaa ggtggtggag     480
gaaaaggcct tcagccctga ggtgatcccc atgttctctg ccctgagcga gggagccaca     540
ccccaggacc tgaacaccat gctgaacacc gtgggagggc accaggctgc catgcagatg     600
ctgaaagaga caatcaacga ggaagctgcc gagtgggaca gggtccaccc agtgcacgct     660
ggacctatcg ctcctggcca gatgagagag cccagaggca gcgatattgc tggcaccacc     720
tccacactgc aggaacagat cggctggatg accaacaacc ctcccatccc tgtgggagag     780
atctacaagc ggtggatcat tctgggactg aacaagatcg tgcggatgta cagccctgtg     840
agcatcctgg acatcaggca gggacccaaa gagcccttca ggactacgt ggaccggttc     900 tacaagaccc tgagagccga gcaggccagc caggacgtga gaactggat gaccgagaca     960 ctgctggtgc agaacgccaa ccctgactgc aagaccatcc tgaaagccct gggacctgct    1020
```

```
gccaccctgg aagagatgat gacagcctgc cagggagtgg gaggacctgg ccacaaggcc    1080
agggtgctgg ccgaggccat gagccaggtg accaactctg ccaccatcat gatgcagaga    1140
ggcaacttcc ggaaccagag aaagaccgtg aagtgcttca actgtggcaa agagggacac    1200
attgccaaga actgcagggc tcccaggaag aaaggctgct ggaagtgcgg aaaagaaggc    1260
caccagatga aggactgcac cgagaggcag gccaacttcc tgggcaagat ctggcctagc    1320
aacaagggca ggcctggcaa cttcctgcag aacagacccg agccaccgc tcctcccgag     1380 gaaagcttcc ggtttggcga ggaaaccacc accccctagcc agaagcagga acccatcgac   1440
aaagagatgt accctctggc cagcctgaag agcctgttcg gcaacgaccc cagcagccag    1500
atggctccca tcagcccaat cgagacagtg cctgtgaagc tgaagcctgg catggacgga   1560
cccagggtga agcagtggcc tctgaccgag gaaaagatca agccctgac agccatctgc    1620 gaggaaatgg aaaagagggg caagatcacc aagatcggac ccgagaaccc ctacaacacc   1680
cctgtgttcg ccatcaagaa gaaagacagc accaagtgga ggaaactggt ggacttcaga   1740
gagctgaaca gcggaccca ggacttctgg gaggtgcagc tgggcatccc tcaccctgct     1800
ggcctgaaga aaaagaaaag cgtgaccgtg ctggctgtgg agatgccta cttcagcgtg     1860 cctctggacg agggcttccg gaagtacaca gccttcacca tccccagcac caacaacgag    1920
acacctggca tcagatacca gtacaacgtg ctgcctcagg gctggaaagg cagccctgcc    1980
atcttccagt gcagcatgac cagaatcctg gaacccttca gagccaagaa ccctgagatc    2040
gtgatctacc agtatatggc tgccctctac gtgggcagcg acctggaaat cggacagcac    2100
agagccaaaa tcgaagaact ccgcgagcac ctgctgaagt ggggattcac caccccctgac  2160 aagaagcacc agaaagagcc tccttcctg tggatgggct acgagctgca ccctgacaag     2220
tggaccgtgc agcccatcca gctgccagag aaggactcct ggaccgtgaa cgacatccag    2280
aaactggtcg gcaagctgaa ctgggccagc cagatctacc ctggcatcaa agtcagacag    2340
ctgtgtaagc tgctgagggg agccaaagca ctgaccgaca tcgtgcctct gacagaagaa    2400
gccgagctgg aactggccga gaacagagag atcctgaaag aacccgtgca cggagtgtac    2460 tacgaccccct ccaaggacct gattgccgag atccagaaac agggacacga ccagtggacc   2520
taccagatct atcaggaacc tttcaagaac ctgaaaacag gcaagtacgc caagatgcgg    2580
acagcccaca ccaacgacgt gaagcagctg accgaagccg tgcagaaaat cgccatggaa    2640
agcatcgtga tctggggaaa gacacccaag ttcaggctgc ccatccagaa agagacatgg    2700
gaaacctggt ggaccgacta ctggcaggcc acctggattc ccgagtggga gttcgtgaac    2760
accccacccc tggtgaagct gtggtatcag ctggaaaagg accctatcgc tggcgtggag    2820
acattctacg tggctggagc tgccaacaga gagacaaagc tgggcaaggc tggctacgtg    2880
accgacagag gcagacagaa aatcgtgagc ctgaccgaaa ccaccaacca gaaaacagcc    2940
ctgcaggcca tctatctggc actgcaggac agcggaagcg aggtgaacat cgtgacagcc   3000
agccagtatg ccctgggcat catccaggcc agcctgaca agagcgagag cgagctggtg    3060
aaccagatca tcgagcagct gatcaagaaa gaacgggtgt acctgagctg ggtgccagcc    3120
cacaagggca tcgagggaa cgagcaggtg gacaagctgg tgtccagcgg aatccggaag    3180
gtgctgttcc tggacggcat cgataaagcc caggaagagc acgagaagta ccacagcaat    3240
tggagagcca tggccagcga cttcaacctg cctcccgtgg tggccaaaga aatcgtggcc    3300
agctgcgacc agtgccagct gaaaggcgag gccatgcacg gacaggtgga ctgctcccct    3360
ggcatctggc agctggcatg cacccacctg gaaggcaaga tcattctggt ggccgtgcac    3420
```

```
gtggccagcg atacatcga agccgaagtg atccctgccg agacagggca ggaaacagcc    3480
tacttcatcc tgaagctggc tggcagatgg cctgtgaagg tgatccacac agccaacggc    3540
agcaacttca cctctgctgc cgtgaaggct gcctgttggt gggctggcat tcagcaggaa    3600
tttggcatcc cctacaatcc ccagtctcag ggagtggtgg ccagcatgaa caaagagctg    3660
aagaagatca tcggacaggt cagggatcag gccgagcacc tgaaaactgc cgtccagatg    3720
gccgtgttca tccacaactt caagcggaag ggagggatcg gagggtactc tgctggcgag    3780
cggatcatcg acatcattgc caccgatatc cagaccaaag agctgcagaa acagatcatc    3840
aagatccaga acttcagggt gtactacagg gacagcaggg accccatctg aagggacct    3900 gccaagctgc tgtggaaagg cgaaggagcc gtcgtcatcc aggacaacag cgacatcaag    3960
gtggtgccca cacggaaggt gaaaatcatc aaggactacg gcaaacagat ggctggagcc    4020
gactgtgtcg ctggcaggca ggacgaggac                                    4050

<210> SEQ ID NO 21
<211> LENGTH: 4023
<212> TYPE: DNA
<213> ORGANISM: Artificial Sequence
<220> FEATURE:
<223> OTHER INFORMATION: nucleotide sequence encoding mos2GagPol

<400> SEQUENCE: 21
atgggagcca gagccagcat cctgcgagga gggaagctgg acaagtggga gaagatcagg      60
ctgaggcctg gagggaagaa acactacatg ctgaagcacc tggtctgggc cagcagagag     120
ctggaacggt ttgccctcaa tcctggcctg ctggaaacca gcgagggctg caagcagatc     180
atcaagcagc tgcagcctgc cctgcagaca ggcaccgagg aactgcggag cctgttcaac     240
accgtggcca ccctgtactg cgtgcatgcc gagatcgaag tgagggacac caaagaagcc     300
ctggacaaga tcgaggaaga gcagaacaag agccagcaga aaacccagca ggccaaagaa     360
gccgacggca aggtctccca gaactacccc atcgtgcaga acctgcaggg acagatggtg     420
caccagccca tcagccctcg cacactgaat gcctgggtga aggtgatcga ggaaaaggcc     480
ttcagccctg aggtgatccc catgttcaca gccctgagcg agggagccac acccccaggac    540 ctgaacacca tgctgaacac cgtgggaggg caccaggctg ccatgcagat gctgaaggac    600
accatcaacg aggaagctgc cgagtgggac aggctgcacc ctgtgcacgc tggacctgtg    660
gctcctggcc agatgagaga gcccagaggc agcgatattg ctggcaccac ctccaatctg    720
caggaacaga tcgcctggat gaccagcaac cctcccatcc ctgtgggaga catctacaag    780
cggtggatca tcctgggact gaacaagatc gtgcggatgt acagccctac ctccatcctg    840
gacatcaagc agggacccaa agagcctttc agggactacg tggaccggtt cttcaagacc    900
ctgagagccg agcaggccac ccaggacgtg aagaactgga tgaccgacac cctgctggtg    960
cagaacgcca cccctgactg caagaccatc ctgagagccc tggaacctgg agccaccctg    1020
gaagagatga tgacagcctg ccagggagtg ggaggaccct tcacaaggc tagggtgctg    1080 gccgaggcca tgagccagac caacagcacc atcctgatgc agcggagcaa cttcaagggc    1140
agcaagcgga tcgtgaagtg cttcaactgt ggcaaagagg gacacattgc cagaaactgt    1200
agggcaccca ggaagaaagg ctgctggaag tgcggaaaag aaggccacca gatgaaggac    1260
tgcaccgaga gcaggccaa cttcctgggc aagatctggc ctagccacaa gggcagacct    1320
ggcaacttcc tgcagagcag accccagccc accgctcctc cagccgagag cttccggttc    1380
```

```
gaggaaacca cccctgctcc caagcaggaa cctaaggaca gagagcctct gaccagcctg    1440
agaagcctgt tcggcagcga ccctctgagc cagatggctc ccatctcccc tatcgagaca    1500
gtgcctgtga agctgaagcc tggcatggac ggacccaagg tgaaacagtg gcctctgacc    1560
gaggaaaaga tcaaagccct ggtggagatc tgtaccgaga tggaaaaaga gggcaagatc    1620
agcaagatcg gacccgagaa ccccctacaac accccctatct tcgccatcaa gaagaaagac    1680
agcaccaagt ggaggaaact ggtggacttc agagagctga acaagcggac ccaggacttc    1740
tgggaggtgc agctgggcat ccctcaccct gctggcctga agaaaaagaa aagcgtgacc    1800
gtgctggccg tgggagatgc ctacttcagc gtgcctctgg acgaggactt cagaaagtac    1860
acagccttca ccatccccag catcaacaac gagacacctg gcatcagata ccagtacaac    1920
gtgctgcctc agggatggaa gggctctcct gcaatcttcc agagcagcat gaccaagatc    1980
ctggaaccct tccggaagca gaaccctgac atcgtgatct accagtacat ggcagccctg    2040
tacgtcggca gcgacctgga atcggacag caccggacca agatcgaaga actcaggcag    2100
cacctgctgc ggtggggatt caccacccct gacaagaagc accagaaaga gcctccttc    2160 ctgtggatgg gctacgagct gcacccagac aagtggaccg tgcagcccat cgtgctgcct    2220
gagaaggact cctggaccgt gaacgacatc cagaaactgg tcggcaagct gaactgggcc    2280
agccagatct acgctggcat caaagtgaag cagctgtgta agctcctgag aggcaccaaa    2340
gccctgaccg aggtggtgcc actgacagag gaagccgagc tggaactggc cgagaacaga    2400
gagatcctga agaacccgt gcacggagtg tactacgacc ccagcaagga cctgattgcc    2460
gagatccaga agcagggaca gggacagtgg acctaccaga tctaccagga acccttcaag    2520
aacctgaaaa caggcaagta cgccaggatg aggggagccc acaccaacga cgtcaaacag    2580
ctgaccgaag ccgtgcagaa gatcgccacc gagagcatcg tgatttgggg aaagacaccc    2640
aagttcaagc tgcccatcca gaaagagaca tgggaggcct ggtggaccga gtactggcag    2700
gccacctgga ttcccgagtg ggagttcgtg aacacccccac ccctggtgaa gctgtggtat    2760
cagctggaaa agaacccat cgtgggagcc gagacattct acgtggctgg agctgccaac    2820
agagagacaa agctgggcaa ggctggctac gtgaccgaca gaggcaggca gaaagtggtg    2880
tccctgaccg ataccaccaa ccagaaaaca gccctgcagg ccatccacct ggctctgcag    2940
gactctggcc tggaagtgaa catcgtgaca gccagccagt atgccctggg catcattcag    3000
gcacagcctg acaagagcga gagcgagctg gtgtctcaga tcattgagca gctgatcaag    3060
aaagaaaagg tgtacctggc ctgggtgcca gcccacaagg ggatcggagg aaacgagcag    3120
gtggacaagc tggtgtccag gggcatccgg aaggtgctgt ttctggacgg catcgacaaa    3180
gcccaggaag agcacgagaa gtaccacagc aattggagag ccatggccag cgagttcaac    3240
ctgcctccca tcgtggccaa agaaatcgtg gcctcttgcg acaagtgcca gctgaaaggc    3300
gaggccattc acggacaggt ggactgcagc ccaggcatct ggcagctggc ctgcacccac    3360
ctggaaggca aggtgatcct ggtggccgtg cacgtggcct ctggatacat cgaagccgaa    3420
gtgatccctg ccgagacagg ccaggaaaca gcctacttcc tgctgaagct ggctggcagg    3480
tggcctgtga aaaccatcca cacagccaac ggcagcaact tcacctctgc caccgtgaag    3540
gctgcctgtt ggtgggctgg cattaagcag gaatttggca tccctacaa ccctcagtct    3600 cagggagtgg tggcctccat caacaaagag ctgaagaaga tcatcggaca ggtcagggat    3660
caggccgagc atctgaaaac agccgtccag atggccgtgt tcatccacaa cttcaagcgg    3720
aagggaggga tcggagagta ctctgctggc gagaggatcg tggacattat cgccagcgat    3780
```

```
atccagacca aagaactgca gaagcagatc acaaagatcc agaacttcag ggtgtactac    3840
agggacagca gagatcccct gtggaaggga cctgccaagc tgctgtggaa aggcgaagga    3900
gccgtcgtca tccaggacaa cagcgacatc aaggtggtgc ccagacggaa ggccaagatc    3960
atcagagact acggcaaaca gatggctggc gacgactgcg tcgcctctag gcaggacgag    4020
gac                                                                 4023
```

<210> SEQ ID NO 22
<211> LENGTH: 2055
<212> TYPE: DNA
<213> ORGANISM: Artificial Sequence
<220> FEATURE:
<223> OTHER INFORMATION: nucleotide sequence encoding mos1Env

<400> SEQUENCE: 22

```
atgcgggtga ccggcatccg gaagaactac cagcacctgt ggcggtgggg caccatgctg      60
ctgggcatcc tgatgatttg ctctgccgcc ggaaagctgt gggtgaccgt gtactacggc     120
gtgcccgtgt ggaaagaggc caccaccacc ctgttctgcg ccagcgacgc caaggcctac     180
gacaccgagg tgcacaacgt gtgggccacc acgccctgcg tgcccaccga ccccaacccc     240
caggaagtgg tcctggaaaa cgtgaccgag aacttcaaca tgtggaagaa caacatggtg     300
gagcagatgc acgaggacat catcagcctg tgggaccaga gcctgaagcc ctgcgtgaag     360 ctgaccccec tgtgcgtgac cctgaactgc accgacgacg tgcggaacgt gaccaacaac     420
gccaccaaca ccaacagcag ctggggcgag cctatggaaa agggcgagat caagaactgc     480
agcttcaaca tcaccaccct catccggaac aaggtgcaga agcagtacgc cctgttctac     540
aagctggacg tggtgcccat cgacaacgac agcaacaaca ccaactaccg gctgatcagc     600
tgcaacacca gcgtgatcac ccaggcctgc cccaaggtgt ccttcgagcc catccccatc     660
cactactgcg cccctgccgg cttcgccatc ctgaagtgca acgacaagaa gttcaacggc     720
accggcccct gcaccaacgt gagcaccgtg cagtgcaccc acggcatccg gcccgtggtg     780
tccacccagc tgctgctgaa cggcagcctg gccgaggaag aggtggtgat cagaagcgag     840
aatttcacca acaatgccaa gaccatcatg gtgcagctga acgtgagcgt ggagatcaac     900
tgcacccggc caacaacaa cacccggaag agcatccaca tcggccctgg cagggccttc     960
tacacagccg gcgacatcat cggcgacatc cggcaggccc actgcaacat cagccgggcc    1020
aactggaaca cacccctgcg gcagatcgtg gagaagctgg gcaagcagtt cggcaacaac    1080
aagaccatcg tgttcaacca cagcagcggc ggagacccccg agatcgtgat gcacagcttc    1140
aactgtggcg gcgagttctt ctactgcaac agcaccaagc tgttcaacag cacctggacc    1200
tggaacaact ccacctggaa taacaccaag cggagcaacg acaccgaaga gcacatcacc    1260
ctgccctgcc ggatcaagca gattatcaat atgtggcagg aggtcggcaa ggccatgtac    1320 gccccctccca tccggggcca gatccggtgc agcagcaaca tcaccggcct gctgctgacc    1380
cgggacggcg gcaacgatac cagcggcacc gagatcttcc ggcctggcgg cggagatatg    1440
cgggacaact ggcggagcga gctgtacaag tacaaggtgg tgaagatcga gcccctgggc    1500
gtggctccca ccaaggccaa gcggcgggtg gtgcagagcg agaagagcgc cgtgggcatc    1560
ggcgccgtgt ttctgggctt cctgggagcc gccggaagca ccatgggagc cgccagcatg    1620
accctgaccg tgcaggcccg gctgctgctg tccggcatcg tgcagcagca gaacaacctg    1680
ctccgggcca tcgaggccca gcagcacctg ctgcagctga ccgtgtgggg catcaagcag    1740
```

| | |
|---|---:|
| ctgcaggcca gggtgctggc cgtggagaga tacctgaagg atcagcagct cctggggatc | 1800 |
| tggggctgca gcggcaagct gatctgcacc accaccgtgc cctggaacgc cagctggtcc | 1860 |
| aacaagagcc tggacaagat ctggaacaat atgacctgga tggaatggga gcgcgagatc | 1920 |
| aacaattaca ccagcctgat ctacacccctg atcgaggaaa gccagaacca gcaggaaaag | 1980 |
| aacgagcagg aactgctgga actggacaag tgggccagcc tgtggaactg gttcgacatc | 2040 |
| agcaactggc tgtgg | 2055 |

<210> SEQ ID NO 23
<211> LENGTH: 2052
<212> TYPE: DNA
<213> ORGANISM: Artificial Sequence
<220> FEATURE:
<223> OTHER INFORMATION: nucleotide sequence encoding mos2Env

<400> SEQUENCE: 23

| | |
|---|---:|
| atgagagtgc ggggcatcca gcggaactgg ccccagtggt ggatctgggg catcctgggc | 60 |
| ttttggatga tcatcatctg ccgggtgatg ggcaacctgt gggtgaccgt gtactacggc | 120 |
| gtgcccgtgt ggaaagaggc caagaccacc ctgttctgcg ccagcgacgc caaggcctac | 180 |
| gagaaagagg tgcacaacgt gtgggccacc acgcctgcg tgcccaccga ccccaacccc | 240 |
| caggaaatgg tcctggaaaa cgtgaccgag aacttcaaca tgtggaagaa cgacatggtg | 300 |
| gaccagatgc acgaggacat catccggctg tgggaccaga gcctgaagcc ctgcgtgaag | 360 |
| ctgaccccc tgtgcgtgac cctggaatgc cggaacgtga aaacgtgag cagcaacggc | 420 |
| acctacaaca tcatccacaa cgagacctac aaagagatga gaactgcag cttcaacgcc | 480 |
| accaccgtgg tggaggaccg gaagcagaag gtgcacgccc tgttctaccg gctggacatc | 540 |
| gtgcccctgg acgagaacaa cagcagcgag aagtccagcg agaacagctc cgagtactac | 600 |
| cggctgatca actgcaacac cagcgccatc acccaggcct gccccaaggt gtccttcgac | 660 |
| cccatcccca tccactactg cgcccctgcc ggctacgcca tcctgaagtg caacaacaag | 720 |
| accttcaacg gcaccggccc ctgcaacaac gtgagcaccg tgcagtgcac ccacggcatc | 780 |
| aagcccgtgt gtccacccca gctgctgctg aacggcagcc tggccgagga agagatcatc | 840 |
| atccggtccg agaacctgac caacaacgcc aagaccatca tcgtgcacct gaatgagacc | 900 |
| gtgaacatca cctgcacccg gcccaacaac aacacccgga gagcatccg gatcggccct | 960 |
| ggccagacct tttacgccac cggcgacatc atcggcgaca tccggcaggc ccactgcaac | 1020 |
| ctgagccggg acggctggaa caagaccctg cagggcgtga agaagaagct ggccgagcac | 1080 |
| ttccccaata gaccatcaa cttccaccagc agcagcggcg gagacctgga aatcaccacc | 1140 |
| cacagcttca actgcagggg cgagttcttc tactgcaata cctccggcct gttcaatggc | 1200 |
| acctacatgc ccaacggcac caacagcaac agcagcagca acatcaccct gccctgccgg | 1260 |
| atcaagcaga tcatcaatat gtggcaggag gtcggcaggg ccatgtacgc ccctcccatc | 1320 |
| gccggcaata tcacctgccg gtccaacatc accggcctgc tgctgaccag ggacggcggc | 1380 |
| agcaacaacg gcgtgcctaa cgacaccgag accttccggc ctggcggcgg agatatgcgg | 1440 |
| aacaactggc ggagcgagct gtacaagtac aaggtggtgg aggtgaagcc cctgggcgtg | 1500 |
| gctcctaccg aggccaagcg gcgggtggtg gagagcgaga gagcgccgt gggcatcggc | 1560 |
| gccgtgtttc tggcattcct gggagccgcc ggaagcacca tgggagccgc cagcatcacc | 1620 |
| ctgaccgtgc aggcccggca gctgctgtcc ggcatcgtgc agcagcagag caacctgctg | 1680 |
| agagccatcg aggcccagca gcacatgctg cagctgaccg tgtgggcat caagcagctg | 1740 |

```
cagacccggg tgctggccat cgagagatac ctgcaggatc agcagctcct gggcctgtgg      1800
ggctgcagcg gcaagctgat ctgcaccacc gccgtgccct ggaacaccag ctggtccaac      1860
aagagccaga ccgacatctg gacaacatg acctggatgc agtgggacaa agagatcggc       1920
aactacaccg gcgagatcta caggctgctg aagagagcc agaaccagca ggaaaagaac       1980
gagaaggacc tgctggccct ggacagctgg aagaacctgt ggaactggtt cgacatcacc      2040
aactggctgt gg                                                         2052

<210> SEQ ID NO 24
<211> LENGTH: 829
<212> TYPE: DNA
<213> ORGANISM: Artificial Sequence
<220> FEATURE:
<223> OTHER INFORMATION: CMV promoter used for expression of antigens in
      Ad26 vectors

<400> SEQUENCE: 24
tcaatattgg ccattagcca tattattcat tggttatata gcataaatca atattggcta       60
ttggccattg catacgttgt atccatatca taatatgtac atttatattg gctcatgtcc      120
aacattaccg ccatgttgac attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca ataatgacgt atgttcccat     300
agtaacgcca tagggacttt ccattgacg tcaatgggtg gagtatttac ggtaaactgc      360
ccacttggca gtacatcaag tgtatcatat gccaagtacg ccccctattg acgtcaatga    420
cggtaaatgg cccgcctggc attatgccca gtacatgacc ttatgggact ttcctacttg    480
gcagtacatc tacgtattag tcatcgctat taccatggtg atgcggtttt ggcagtacat    540
caatgggcgt ggatagcggt ttgactcacg gggatttcca agtctccacc ccattgacgt    600
caatgggagt ttgttttggc accaaaatca acgggacttt ccaaaatgtc gtaacaactc    660
cgccccattg acgcaaatgg gcggtaggcg tgtacggtgg gaggtctata taagcagagc    720
tcgtttagtg aaccgtcaga tcgcctggag acgccatcca cgctgttttg acctccatag    780
aagacaccgg gaccgatcca gcctccgcgg ccgggaacgg tgcattgga               829

<210> SEQ ID NO 25
<211> LENGTH: 2586
<212> TYPE: DNA
<213> ORGANISM: Artificial Sequence
<220> FEATURE:
<223> OTHER INFORMATION: nucleotide sequence encoding C4

<400> SEQUENCE: 25
atgagagtgc ggggcatgct gagaaactgg cagcagtggt ggatctggtc cagcctgggc      60
ttctggatgc tgatgatcta cagcgtgatg ggcaacctgt gggtcaccgt gtactacggc     120
gtgcccgtgt ggaaggacgc caagaccacc ctgttttgcg cctccgatgc caaggcctac     180
gagaaagagg tgcacaacgt ctgggccacc cacgcctgtg tgcccaccga ccccaatccc    240
caggaaatcg tcctgggcaa cgtgaccgag aacttcaaca tgtggaagaa cgacatggtc    300
gatcagatgc acgaggacat catctcctg tgggacgcct ccctggaacc ctgcgtgaag    360
ctgacccctc tgtgcgtgac cctgaactgc ggaacgtgc gcaacgtgtc agcaacggc     420 acctacaaca tcatccacaa cgagacatac aaagagatga gaactgcag cttcaacgct     480 accaccgtgg tcgaggaccg gaagcagaag gtgcacgccc tgttctaccg gctggacatc    540
```

```
gtgcccctgg acgagaacaa cagcagcgag aagtcctccg agaacagctc cgagtactac    600
agactgatca actgcaacac cagcgccatc acccaggcct gccccaaggt gtccttcgac    660
cctatcccca tccactactg cgcccctgcc ggctacgcca tcctgaagtg caacaacaag    720
accttcaatg gcaccggccc ctgcaacaat gtgtccaccg tgcagtgcac ccacggcatc    780
aagcccgtgg tgtctaccca gctgctgctg aacggcagcc tggccgagga agagatcatt    840
atcagaagcg agaacctgac caacaacgcc aaaaccatca tcgtccacct gaacgaaacc    900
gtgaacatca cctgtacccg gcctaacaac aacacccgga agtccatccg gatcggccct    960
ggccagacct tttacgccac cggcgatatt atcggcgaca tccggcaggc ccactgcaat   1020
ctgagccggg acggctggaa caagacactg cagggcgtca gaagaagct ggccgaacac    1080 ttccctaaca agactatcaa gttcgcccct cactctggcg cgacctgga aatcaccacc    1140 cacaccttca actgtcgggg cgagttcttc tactgcaata cctccaacct gttcaacgag    1200
agcaacatcg agcggaacga cagcatcatc acactgcctt gccggatcaa gcagattatc    1260
aatatgtggc aggaagtggg cagagccatc tacgcccctc caatcgccgg caacatcaca    1320
tgccggtcca atatcaccgg cctgctgctc accagagatg gcggctccaa caatggcgtg    1380
ccaaacgaca ccgagacatt cagacccggc ggaggcgaca tgcggaacaa ttggcggagc    1440
gagctgtaca agtacaaggt ggtggaagtg aagcccctgg gcgtggcccc taccgaggcc    1500
aagagaagag tggtcgaacg cgagaagcgg gccgtgggaa tcggagccgt gtttctggga    1560
atcctgggag ccgctggctc taccatgggc gctgcctcta tcaccctgac agtgcaggcc    1620
agacagctgc tcagcggcat cgtgcagcag cagagcaacc tgctgagagc cattgaggcc    1680
cagcagcaca tgctgcagct gaccgtgtgg ggcattaagc agctccagac acgggtgctg    1740
gccatcgaga gatacctgca ggatcagcag ctcctgggcc tgtggggctg tagcggcaag    1800
ctgatctgta ccaccgccgt gcctggaat acctcttgga gcaacaagag ccagaccgac    1860
atctgggaca acatgacctg gatgcagtgg gacaaagaaa tcggcaacta taccggcgag    1920
atctatagac tgctggaaga gtcccagaac cagcaggaaa agaacgagaa ggaccctgctg    1980 gccctggatt cttggaacaa tctgtggaac tggttcagca tctccaagtg gctgtggtac    2040
atcaagatct tcatcatgat cgtgggcggc ctgatcggcc tgcggatcat ctttgccgtg    2100
ctgagcatcg tgaaccgcgt gcggcaggga tacagccctc tgagcctgca gaccctgact    2160
cagaaccctg gcggactgga cagactgggc cggattgagg aagaaggcgg cgagcaggac    2220
aaggatcgga gcatcaggct ggtcaacggc ttcttcgctc tgttttggga cgacctgcgg    2280
agcctgtgcc tgttcagcta ccacagactg cgggacttta tcctgattgt ggccagagcc    2340
gtcgaactgc tggggagaag ctctctgaga ggcctgcagc ggggctggga gattctgaag    2400
tacctgggct ccctgctgca gtactgggc ctggaactga agaagtctgc catcaatctg    2460
ctcgacacaa tcgctattgc cgtggccgaa ggcaccgata gaatcatcga gctgatccag    2520
cggatctgcc gggccatctg caacatcccc agacggatca gacagggctt cgaggccgct    2580
ctgcag                                                              2586
```

<210> SEQ ID NO 26
<211> LENGTH: 2133
<212> TYPE: DNA
<213> ORGANISM: Artificial Sequence
<220> FEATURE:
<223> OTHER INFORMATION: nucleotide sequence encoding C4D7

<400> SEQUENCE: 26

```
atgagagtgc ggggcatgct gagaaactgg cagcagtggt ggatctggtc cagcctgggc    60
ttctggatgc tgatgatcta cagcgtgatg ggcaacctgt gggtcaccgt gtactacggc   120
gtgcccgtgt ggaaggacgc caagaccacc ctgttttgcg cctccgatgc caaggcctac   180
gagaagagg tgcacaacgt ctgggccacc cacgcctgtg tgcccaccga ccccaatccc    240
caggaaatcg tcctgggcaa cgtgaccgag aacttcaaca tgtggaagaa cgacatggtc   300
gatcagatgc acgaggacat catctccctg tgggacgcct ccctggaacc ctgcgtgaag   360
ctgaccccctc tgtgcgtgac cctgaactgc cggaacgtgc gcaacgtgtc cagcaacggc   420
acctacaaca tcatccacaa cgagacatac aaagagatga gaactgcag cttcaacgct    480
accaccgtgg tcgaggaccg gaagcagaag gtgcacgccc tgttctaccg gctggacatc   540
gtgcccctgg acgagaacaa cagcagcgag aagtcctccg agaacagctc cgagtactac   600
agactgatca actgcaacac cagcgccatc acccaggcct gccccaaggt gtccttcgac   660
cctatcccca tccactactg cgcccctgcc ggctacgcca tcctgaagtg caacaacaag   720
accttcaatg gcaccggccc ctgcaacaat gtgtccaccg tgcagtgcac ccacggcatc   780
aagcccgtgg tgtctaccca gctgctgctg aacggcagcc tggccgagga agagatcatt   840
atcagaagcg agaacctgac caacaacgcc aaaaccatca tcgtccacct gaacgaaacc   900
gtgaacatca ccctgtaccc ggcctaacaa cacacccgga agtccatccg gatcggccct   960
ggccagacct tttacgccac cggcgatatt atcggcgaca tccggcaggc ccactgcaat  1020
ctgagccggg acggctggaa caagacactg cagggcgtca gaagaagct ggccgaacac   1080
ttccctaaca agactatcaa gttcgccccct cactctggcg gcgacctgga aatcaccacc   1140
cacaccttca actgtcgggg cgagttcttc tactgcaata cctccaacct gttcaacgag   1200
agcaacatcg agcggaacga cagcatcatc acactgcctt gccggatcaa gcagattatc   1260
aatatgtggc aggaagtggg cagagccatc tacgcccctc caatcgccgg caacatcaca   1320
tgccggtcca atatcaccgg cctgctgctc accagagatg cggctccaa caatggcgtg   1380
ccaaacgaca ccgagacatt cagacccggc ggaggcgaca tgcggaacaa ttggcggagc   1440
gagctgtaca agtacaaggt ggtggaagtg aagcccctgg gcgtggcccc taccgaggcc   1500
aagagaagag tggtcgaacg cgagaagcgg gccgtgggaa tcgagccgt gtttctggga   1560
atcctgggag ccgctggctc taccatgggc gctgcctcta tcaccctgac agtgcaggcc   1620
agacagctgc tcagcggcat cgtgcagcag cagagcaacc tgctgagagc cattgaggcc   1680
cagcagcaca tgctgcagct gaccgtgtgg ggcattaagc agctccagac acgggtgctg   1740
gccatcgaga gatacctgca ggatcagcag ctcctgggcc tgtggggctg tagcggcaag   1800
ctgatctgta ccaccgccgt gccctggaat acctcttgga gcaacaagag ccagaccgac   1860
atctgggaca catgacctg gatgcagtgg gacaaagaaa tcggcaacta taccggcgag   1920
atctatagac tgctggaaga gtcccagaac cagcaggaaa agaacgagaa ggacctgctg   1980
gccctggatt cttggaacaa tctgtggaac tggttcagca tctccaagtg gctgtggtac   2040
atcaagatct tcatcatgat cgtgggcggc ctgatcggcc tgcggatcat ctttgccgtg   2100
ctgagcatcg tgaaccgcgt gcggcagggc tac                               2133
```

<210> SEQ ID NO 27
<211> LENGTH: 2112
<212> TYPE: DNA
<213> ORGANISM: Artificial Sequence
<220> FEATURE:
<223> OTHER INFORMATION: nucleotide sequence encoding sC4

<400> SEQUENCE: 27

```
atgagagtgc ggggcatgct gagaaactgg cagcagtggt ggatctggtc cagcctgggc      60
ttctggatgc tgatgatcta cagcgtgatg ggcaacctgt gggtcaccgt gtactacggc     120
gtgcccgtgt ggaaggacgc caagaccacc ctgttttgcg cctccgatgc caaggcctac     180
gagaaagagg tgcacaacgt ctgggccacc cacgcctgtg tgcccaccga ccccaatccc     240
caggaaatcg tcctgggcaa cgtgaccgag aacttcaaca tgtggaagaa cgacatggtc     300
gatcagatgc acgaggacat catctccctg tgggacgcct ccctggaacc tgcgtgaag     360
ctgaccccctc tgtgcgtgac cctgaactgc cggaacgtgc gcaacgtgtc cagcaacggc     420
acctacaaca tcatccacaa cgagacatac aaagagatga gaactgcag cttcaacgct     480
accaccgtgg tcgaggaccg gaagcagaag gtgcacgccc tgttctaccg gctggacatc     540
gtgcccctgg acgagaacaa cagcagcgag aagtcctccg agaacagctc cgagtactac     600
agactgatca actgcaacac cagcgccatc acccaggcct gccccaaggt gtccttcgac     660
cctatcccca tccactactg cgcccctgcc ggctacgcca tcctgaagtg caacaacaag     720
accttcaatg gcaccggccc ctgcaacaat gtgtccaccg tgcagtgcac ccacggcatc     780
aagcccgtgg tgtctaccca gctgctgctg aacggcagcc tggccgagga agagatcatt     840
atcagaagcg agaacctgac caacaacgcc aaaaccatca tcgtccacct gaacgaaacc     900
gtgaacatca cctgtacccg gcctaacaac aacacccgga gtccatccg gatcggccct     960
ggccagacct tttacgccac cggcgatatt atcggcgaca tccggcaggc ccactgcaat    1020
ctgagccggg acggctggaa caagacactg cagggcgtca gaagaagct ggccgaacac    1080
ttccctaaca agactatcaa gttcgcccct cactctggcg gcgacctgga aatcaccacc    1140
cacaccttca actgtcgggg cgagttcttc tactgcaata cctccaacct gttcaacgag    1200
agcaacatcg agcggaacga cagcatcatc acactgcctt gccggatcaa gcagattatc    1260
aatatgtggc aggaagtggg cagagccatc tacgcccctc caatcgccgg caacatcaca    1320
tgccggtcca atatcaccgg cctgctgctc accagagatg cgggctccaa caatggcgtg    1380
ccaaacgaca ccgagacatt cagacccggc ggaggcgaca tgcggaacaa ttggcggagc    1440
gagctgtaca gtacaaggt ggtggaagtg aagcccctgg gcgtggcccc taccgaggcc    1500
aagagaagag tggtcgaacg cgaggaacgg gccgtgggaa tcggagccgt gtttctggga    1560
atcctgggag ccgctggctc taccatgggc gctgcctcta tcaccctgac agtgcaggcc    1620
agacagctgc tcagcggcat cgtgcagcag cagagcaacc tgctgagagc cattgaggcc    1680
cagcagcaca tgctgcagct gaccgtgtgg ggcattaagc agctccagac acgggtgctg    1740
gccatcgaga gatacctgca ggatcagcag ctcctgggcc tgtggggctg tagcggcaag    1800
ctgatctgta ccaccgccgt gccctggaat acctcttgga gcaacaagag ccagaccgac    1860
atctgggaca acatgacctg gatgcagtgg gacaaagaaa tcggcaacta taccggcgag    1920
atctatagac tgctggaaga gtcccagaac cagcaggaaa agatgaagca gatcgaggac    1980
aagatcgaag agattctgag caagatctac cacatcgaga acgagatcgc cgcatcaag    2040
aaactgatcg gcgaagtggg atccggcgct cccacaaagg ccaaaagacg ggtggtgcag    2100
cgcgagaaac gc                                                         2112
```

<210> SEQ ID NO 28

<211> LENGTH: 1350
<212> TYPE: PRT
<213> ORGANISM: Artificial Sequence
<220> FEATURE:
<223> OTHER INFORMATION: mos1GagPol mosaic antigen sequence

<400> SEQUENCE: 28

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

Lys Lys Ala Gln Gln Ala Ala Ala Asp Thr Gly Asn Ser Ser Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Val Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Asp Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Ser Ala Thr Ile Met Met Gln Arg Gly Asn Phe Arg
    370                 375                 380
```

```
Asn Gln Arg Lys Thr Val Lys Cys Phe Asn Cys Gly Lys Glu Gly His
385                 390                 395                 400

Ile Ala Lys Asn Cys Arg Ala Pro Arg Lys Gly Cys Trp Lys Cys
                405                 410                 415

Gly Lys Glu Gly His Gln Met Lys Asp Cys Thr Glu Arg Gln Ala Asn
            420                 425                 430

Phe Leu Gly Lys Ile Trp Pro Ser Asn Lys Gly Arg Pro Gly Asn Phe
            435                 440                 445

Leu Gln Asn Arg Pro Glu Pro Thr Ala Pro Glu Glu Ser Phe Arg
        450                 455                 460

Phe Gly Glu Glu Thr Thr Thr Pro Ser Gln Lys Gln Glu Pro Ile Asp
465                 470                 475                 480

Lys Glu Met Tyr Pro Leu Ala Ser Leu Lys Ser Leu Phe Gly Asn Asp
                485                 490                 495

Pro Ser Ser Gln Met Ala Pro Ile Ser Pro Ile Glu Thr Val Pro Val
                500                 505                 510

Lys Leu Lys Pro Gly Met Asp Gly Pro Arg Val Lys Gln Trp Pro Leu
            515                 520                 525

Thr Glu Glu Lys Ile Lys Ala Leu Thr Ala Ile Cys Glu Glu Met Glu
            530                 535                 540

Lys Glu Gly Lys Ile Thr Lys Ile Gly Pro Glu Asn Pro Tyr Asn Thr
545                 550                 555                 560

Pro Val Phe Ala Ile Lys Lys Lys Asp Ser Thr Lys Trp Arg Lys Leu
                565                 570                 575

Val Asp Phe Arg Glu Leu Asn Lys Arg Thr Gln Asp Phe Trp Glu Val
            580                 585                 590

Gln Leu Gly Ile Pro His Pro Ala Gly Leu Lys Lys Lys Lys Ser Val
            595                 600                 605

Thr Val Leu Ala Val Gly Asp Ala Tyr Phe Ser Val Pro Leu Asp Glu
        610                 615                 620

Gly Phe Arg Lys Tyr Thr Ala Phe Thr Ile Pro Ser Thr Asn Asn Glu
625                 630                 635                 640

Thr Pro Gly Ile Arg Tyr Gln Tyr Asn Val Leu Pro Gln Gly Trp Lys
                645                 650                 655

Gly Ser Pro Ala Ile Phe Gln Cys Ser Met Thr Arg Ile Leu Glu Pro
                660                 665                 670

Phe Arg Ala Lys Asn Pro Glu Ile Val Ile Tyr Gln Tyr Met Ala Ala
            675                 680                 685

Leu Tyr Val Gly Ser Asp Leu Glu Ile Gly Gln His Arg Ala Lys Ile
            690                 695                 700

Glu Glu Leu Arg Glu His Leu Leu Lys Trp Gly Phe Thr Thr Pro Asp
705                 710                 715                 720

Lys Lys His Gln Lys Glu Pro Pro Phe Leu Trp Met Gly Tyr Glu Leu
                725                 730                 735

His Pro Asp Lys Trp Thr Val Gln Pro Ile Gln Leu Pro Glu Lys Asp
            740                 745                 750

Ser Trp Thr Val Asn Asp Ile Gln Lys Leu Val Gly Lys Leu Asn Trp
            755                 760                 765

Ala Ser Gln Ile Tyr Pro Gly Ile Lys Val Arg Gln Leu Cys Lys Leu
        770                 775                 780

Leu Arg Gly Ala Lys Ala Leu Thr Asp Ile Val Pro Leu Thr Glu Glu
785                 790                 795                 800
```

```
Ala Glu Leu Glu Leu Ala Glu Asn Arg Glu Ile Leu Lys Glu Pro Val
                805                 810                 815
His Gly Val Tyr Tyr Asp Pro Ser Lys Asp Leu Ile Ala Glu Ile Gln
        820                 825                 830
Lys Gln Gly His Asp Gln Trp Thr Tyr Gln Ile Tyr Gln Glu Pro Phe
        835                 840                 845
Lys Asn Leu Lys Thr Gly Lys Tyr Ala Lys Met Arg Thr Ala His Thr
850                 855                 860
Asn Asp Val Lys Gln Leu Thr Glu Ala Val Gln Lys Ile Ala Met Glu
865                 870                 875                 880
Ser Ile Val Ile Trp Gly Lys Thr Pro Lys Phe Arg Leu Pro Ile Gln
                885                 890                 895
Lys Glu Thr Trp Glu Thr Trp Trp Thr Asp Tyr Trp Gln Ala Thr Trp
            900                 905                 910
Ile Pro Glu Trp Glu Phe Val Asn Thr Pro Pro Leu Val Lys Leu Trp
                915                 920                 925
Tyr Gln Leu Glu Lys Asp Pro Ile Ala Gly Val Glu Thr Phe Tyr Val
        930                 935                 940
Ala Gly Ala Ala Asn Arg Glu Thr Lys Leu Gly Lys Ala Gly Tyr Val
945                 950                 955                 960
Thr Asp Arg Gly Arg Gln Lys Ile Val Ser Leu Thr Glu Thr Thr Asn
                965                 970                 975
Gln Lys Thr Ala Leu Gln Ala Ile Tyr Leu Ala Leu Gln Asp Ser Gly
            980                 985                 990
Ser Glu Val Asn Ile Val Thr Ala  Ser Gln Tyr Ala Leu  Gly Ile Ile
            995                 1000                1005
Gln Ala  Gln Pro Asp Lys Ser  Glu Ser Glu Leu Val  Asn Gln Ile
     1010                1015                1020
Ile Glu  Gln Leu Ile Lys Lys  Glu Arg Val Tyr Leu  Ser Trp Val
     1025                1030                1035
Pro Ala  His Lys Gly Ile Gly  Gly Asn Glu Gln Val  Asp Lys Leu
     1040                1045                1050
Val Ser  Ser Gly Ile Arg Lys  Val Leu Phe Leu Asp  Gly Ile Asp
     1055                1060                1065
Lys Ala  Gln Glu Glu His Glu  Lys Tyr His Ser Asn  Trp Arg Ala
     1070                1075                1080
Met Ala  Ser Asp Phe Asn Leu  Pro Pro Val Val Ala  Lys Glu Ile
     1085                1090                1095
Val Ala  Ser Cys Asp Gln Cys  Gln Leu Lys Gly Glu  Ala Met His
     1100                1105                1110
Gly Gln  Val Asp Cys Ser Pro  Gly Ile Trp Gln Leu  Ala Cys Thr
     1115                1120                1125
His Leu  Glu Gly Lys Ile Ile  Leu Val Ala Val His  Val Ala Ser
     1130                1135                1140
Gly Tyr  Ile Glu Ala Glu Val  Ile Pro Ala Glu Thr  Gly Gln Glu
     1145                1150                1155
Thr Ala  Tyr Phe Ile Leu Lys  Leu Ala Gly Arg Trp  Pro Val Lys
     1160                1165                1170
Val Ile  His Thr Ala Asn Gly  Ser Asn Phe Thr Ser  Ala Ala Val
     1175                1180                1185
Lys Ala  Ala Cys Trp Trp Ala  Gly Ile Gln Gln Glu  Phe Gly Ile
     1190                1195                1200
Pro Tyr  Asn Pro Gln Ser Gln  Gly Val Val Ala Ser  Met Asn Lys
```

```
                1205                1210                1215

Glu  Leu  Lys  Lys  Ile  Ile  Gly  Gln  Val  Arg  Asp  Gln  Ala  Glu  His
          1220                1225                1230

Leu  Lys  Thr  Ala  Val  Gln  Met  Ala  Val  Phe  Ile  His  Asn  Phe  Lys
     1235                1240                1245

Arg  Lys  Gly  Gly  Ile  Gly  Gly  Tyr  Ser  Ala  Gly  Glu  Arg  Ile  Ile
1250                1255                1260

Asp  Ile  Ile  Ala  Thr  Asp  Ile  Gln  Thr  Lys  Glu  Leu  Gln  Lys  Gln
1265                1270                1275

Ile  Ile  Lys  Ile  Gln  Asn  Phe  Arg  Val  Tyr  Tyr  Arg  Asp  Ser  Arg
     1280                1285                1290

Asp  Pro  Ile  Trp  Lys  Gly  Pro  Ala  Lys  Leu  Leu  Trp  Lys  Gly  Glu
          1295                1300                1305

Gly  Ala  Val  Val  Ile  Gln  Asp  Asn  Ser  Asp  Ile  Lys  Val  Val  Pro
     1310                1315                1320

Arg  Arg  Lys  Val  Lys  Ile  Ile  Lys  Asp  Tyr  Gly  Lys  Gln  Met  Ala
1325                1330                1335

Gly  Ala  Asp  Cys  Val  Ala  Gly  Arg  Gln  Asp  Glu  Asp
     1340                1345                1350

<210> SEQ ID NO 29
<211> LENGTH: 1341
<212> TYPE: PRT
<213> ORGANISM: Artificial Sequence
<220> FEATURE:
<223> OTHER INFORMATION: mos2GagPol mosaic antigen sequence

<400> SEQUENCE: 29

Met  Gly  Ala  Arg  Ala  Ser  Ile  Leu  Arg  Gly  Gly  Lys  Leu  Asp  Lys  Trp
1                 5                  10                 15

Glu  Lys  Ile  Arg  Leu  Arg  Pro  Gly  Gly  Lys  Lys  His  Tyr  Met  Leu  Lys
                 20                  25                 30

His  Leu  Val  Trp  Ala  Ser  Arg  Glu  Leu  Glu  Arg  Phe  Ala  Leu  Asn  Pro
             35                  40                  45

Gly  Leu  Leu  Glu  Thr  Ser  Glu  Gly  Cys  Lys  Gln  Ile  Ile  Lys  Gln  Leu
         50                  55                  60

Gln  Pro  Ala  Leu  Gln  Thr  Gly  Thr  Glu  Glu  Leu  Arg  Ser  Leu  Phe  Asn
65                  70                  75                  80

Thr  Val  Ala  Thr  Leu  Tyr  Cys  Val  His  Ala  Glu  Ile  Glu  Val  Arg  Asp
                 85                  90                  95

Thr  Lys  Glu  Ala  Leu  Asp  Lys  Ile  Glu  Glu  Glu  Gln  Asn  Lys  Ser  Gln
             100                 105                 110

Gln  Lys  Thr  Gln  Gln  Ala  Lys  Glu  Ala  Asp  Gly  Lys  Val  Ser  Gln  Asn
         115                 120                 125

Tyr  Pro  Ile  Val  Gln  Asn  Leu  Gln  Gly  Gln  Met  Val  His  Gln  Pro  Ile
130                 135                 140

Ser  Pro  Arg  Thr  Leu  Asn  Ala  Trp  Val  Lys  Val  Ile  Glu  Glu  Lys  Ala
145                 150                 155                 160

Phe  Ser  Pro  Glu  Val  Ile  Pro  Met  Phe  Thr  Ala  Leu  Ser  Glu  Gly  Ala
                 165                 170                 175

Thr  Pro  Gln  Asp  Leu  Asn  Thr  Met  Leu  Asn  Thr  Val  Gly  Gly  His  Gln
             180                 185                 190

Ala  Ala  Met  Gln  Met  Leu  Lys  Asp  Thr  Ile  Asn  Glu  Glu  Ala  Ala  Glu
         195                 200                 205

Trp  Asp  Arg  Leu  His  Pro  Val  His  Ala  Gly  Pro  Val  Ala  Pro  Gly  Gln
```

```
              210                 215                 220
Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
                260                 265                 270

Met Tyr Ser Pro Thr Ser Ile Leu Asp Ile Lys Gln Gly Pro Lys Glu
            275                 280                 285

Pro Phe Arg Asp Tyr Val Asp Arg Phe Phe Lys Thr Leu Arg Ala Glu
        290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
                340                 345                 350

Pro Ser His Lys Ala Arg Val Leu Ala Glu Ala Met Ser Gln Thr Asn
            355                 360                 365

Ser Thr Ile Leu Met Gln Arg Ser Asn Phe Lys Gly Ser Lys Arg Ile
        370                 375                 380

Val Lys Cys Phe Asn Cys Gly Lys Glu Gly His Ile Ala Arg Asn Cys
385                 390                 395                 400

Arg Ala Pro Arg Lys Lys Gly Cys Trp Lys Cys Gly Lys Glu Gly His
                405                 410                 415

Gln Met Lys Asp Cys Thr Glu Arg Gln Ala Asn Phe Leu Gly Lys Ile
                420                 425                 430

Trp Pro Ser His Lys Gly Arg Pro Gly Asn Phe Leu Gln Ser Arg Pro
            435                 440                 445

Glu Pro Thr Ala Pro Pro Ala Glu Ser Phe Arg Phe Glu Glu Thr Thr
        450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                485                 490                 495

Pro Ile Glu Thr Val Pro Val Lys Leu Lys Pro Gly Met Asp Gly Pro
                500                 505                 510

Lys Val Lys Gln Trp Pro Leu Thr Glu Glu Lys Ile Lys Ala Leu Val
            515                 520                 525

Glu Ile Cys Thr Glu Met Glu Lys Glu Gly Lys Ile Ser Lys Ile Gly
        530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
                565                 570                 575

Thr Gln Asp Phe Trp Glu Val Gln Leu Gly Ile Pro His Pro Ala Gly
                580                 585                 590

Leu Lys Lys Lys Lys Ser Val Thr Val Leu Ala Val Gly Asp Ala Tyr
            595                 600                 605

Phe Ser Val Pro Leu Asp Glu Asp Phe Arg Lys Tyr Thr Ala Phe Thr
        610                 615                 620

Ile Pro Ser Ile Asn Asn Glu Thr Pro Gly Ile Arg Tyr Gln Tyr Asn
625                 630                 635                 640
```

```
Val Leu Pro Gln Gly Trp Lys Gly Ser Pro Ala Ile Phe Gln Ser Ser
                645                 650                 655

Met Thr Lys Ile Leu Glu Pro Phe Arg Lys Gln Asn Pro Asp Ile Val
            660                 665                 670

Ile Tyr Gln Tyr Met Ala Ala Leu Tyr Val Gly Ser Asp Leu Glu Ile
        675                 680                 685

Gly Gln His Arg Thr Lys Ile Glu Glu Leu Arg Gln His Leu Leu Arg
    690                 695                 700

Trp Gly Phe Thr Thr Pro Asp Lys Lys His Gln Lys Glu Pro Pro Phe
705                 710                 715                 720

Leu Trp Met Gly Tyr Glu Leu His Pro Asp Lys Trp Thr Val Gln Pro
                725                 730                 735

Ile Val Leu Pro Glu Lys Asp Ser Trp Thr Val Asn Asp Ile Gln Lys
            740                 745                 750

Leu Val Gly Lys Leu Asn Trp Ala Ser Gln Ile Tyr Ala Gly Ile Lys
        755                 760                 765

Val Lys Gln Leu Cys Lys Leu Leu Arg Gly Thr Lys Ala Leu Thr Glu
    770                 775                 780

Val Val Pro Leu Thr Glu Glu Ala Glu Leu Glu Leu Ala Glu Asn Arg
785                 790                 795                 800

Glu Ile Leu Lys Glu Pro Val His Gly Val Tyr Tyr Asp Pro Ser Lys
                805                 810                 815

Asp Leu Ile Ala Glu Ile Gln Lys Gln Gly Gln Gly Gln Trp Thr Tyr
            820                 825                 830

Gln Ile Tyr Gln Glu Pro Phe Lys Asn Leu Lys Thr Gly Lys Tyr Ala
        835                 840                 845

Arg Met Arg Gly Ala His Thr Asn Asp Val Lys Gln Leu Thr Glu Ala
    850                 855                 860

Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
                885                 890                 895

Glu Tyr Trp Gln Ala Thr Trp Ile Pro Glu Trp Glu Phe Val Asn Thr
            900                 905                 910

Pro Pro Leu Val Lys Leu Trp Tyr Gln Leu Glu Lys Glu Pro Ile Val
        915                 920                 925

Gly Ala Glu Thr Phe Tyr Val Ala Gly Ala Ala Asn Arg Glu Thr Lys
    930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
                965                 970                 975

Leu Ala Leu Gln Asp Ser Gly Leu Glu Val Asn Ile Val Thr Ala Ser
            980                 985                 990

Gln Tyr Ala Leu Gly Ile Ile Gln Ala Gln Pro Asp Lys Ser Glu Ser
        995                 1000                1005

Glu Leu Val Ser Gln Ile Ile Glu Gln Leu Ile Lys Lys Glu Lys
        1010                1015                1020

Val Tyr Leu Ala Trp Val Pro Ala His Lys Gly Ile Gly Gly Asn
        1025                1030                1035

Glu Gln Val Asp Lys Leu Val Ser Arg Gly Ile Arg Lys Val Leu
        1040                1045                1050
```

```
Phe Leu Asp Gly Ile Asp Lys Ala Gln Glu Glu His Glu Lys Tyr
1055                1060                1065

His Ser Asn Trp Arg Ala Met Ala Ser Glu Phe Asn Leu Pro Pro
    1070                1075                1080

Ile Val Ala Lys Glu Ile Val Ala Ser Cys Asp Lys Cys Gln Leu
        1085                1090                1095

Lys Gly Glu Ala Ile His Gly Gln Val Asp Cys Ser Pro Gly Ile
    1100                1105                1110

Trp Gln Leu Ala Cys Thr His Leu Glu Gly Lys Val Ile Leu Val
    1115                1120                1125

Ala Val His Val Ala Ser Gly Tyr Ile Glu Ala Glu Val Ile Pro
    1130                1135                1140

Ala Glu Thr Gly Gln Glu Thr Ala Tyr Phe Leu Leu Lys Leu Ala
    1145                1150                1155

Gly Arg Trp Pro Val Lys Thr Ile His Thr Ala Asn Gly Ser Asn
    1160                1165                1170

Phe Thr Ser Ala Thr Val Lys Ala Ala Cys Trp Trp Ala Gly Ile
    1175                1180                1185

Lys Gln Glu Phe Gly Ile Pro Tyr Asn Pro Gln Ser Gln Gly Val
    1190                1195                1200

Val Ala Ser Ile Asn Lys Glu Leu Lys Lys Ile Gly Gln Val
    1205                1210                1215

Arg Asp Gln Ala Glu His Leu Lys Thr Ala Val Gln Met Ala Val
    1220                1225                1230

Phe Ile His Asn Phe Lys Arg Lys Gly Gly Ile Gly Glu Tyr Ser
    1235                1240                1245

Ala Gly Glu Arg Ile Val Asp Ile Ile Ala Ser Asp Ile Gln Thr
    1250                1255                1260

Lys Glu Leu Gln Lys Gln Ile Thr Lys Ile Gln Asn Phe Arg Val
    1265                1270                1275

Tyr Tyr Arg Asp Ser Arg Asp Pro Leu Trp Lys Gly Pro Ala Lys
    1280                1285                1290

Leu Leu Trp Lys Gly Glu Gly Ala Val Val Ile Gln Asp Asn Ser
    1295                1300                1305

Asp Ile Lys Val Val Pro Arg Arg Lys Ala Lys Ile Ile Arg Asp
    1310                1315                1320

Tyr Gly Lys Gln Met Ala Gly Asp Asp Cys Val Ala Ser Arg Gln
    1325                1330                1335

Asp Glu Asp
    1340
```

<210> SEQ ID NO 30
<211> LENGTH: 709
<212> TYPE: PRT
<213> ORGANISM: Artificial Sequence
<220> FEATURE:
<223> OTHER INFORMATION: sC1 sequence

<400> SEQUENCE: 30

```
Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
                20                  25                  30

Leu Trp Val Thr Val Tyr Tyr Gly Val Pro Val Trp Lys Glu Ala Lys
            35                  40                  45
```

-continued

```
Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
            100                 105                 110

Gln Ser Leu Lys Pro Cys Val Lys Leu Thr Pro Leu Cys Val Thr Leu
        115                 120                 125

Glu Cys Arg Asn Val Arg Asn Val Ser Ser Asn Gly Thr Tyr Asn Ile
    130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
    210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
    290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Asn Phe
        355                 360                 365

Thr Ser Ser Ser Gly Gly Asp Leu Glu Ile Thr Thr His Ser Phe Asn
    370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
            420                 425                 430

Arg Ala Met Tyr Ala Pro Pro Ile Ala Gly Asn Ile Thr Cys Arg Ser
        435                 440                 445

Asn Ile Thr Gly Leu Leu Leu Thr Arg Asp Gly Gly Ser Asn Asn Gly
    450                 455                 460

Val Pro Asn Asp Thr Glu Thr Phe Arg Pro Gly Gly Gly Asp Met Arg
```

```
                465                 470                 475                 480
Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Arg
                500                 505                 510

Glu Glu Arg Ala Val Gly Ile Gly Ala Val Phe Leu Gly Ile Leu Gly
                515                 520                 525

Ala Ala Gly Ser Thr Met Gly Ala Ala Ser Ile Thr Leu Thr Val Gln
530                 535                 540

Ala Arg Gln Leu Leu Ser Gly Ile Val Gln Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
                580                 585                 590

Asp Gln Gln Leu Leu Gly Leu Trp Gly Cys Ser Gly Lys Leu Ile Cys
                595                 600                 605

Thr Thr Ala Val Pro Trp Asn Thr Ser Trp Ser Asn Lys Ser Gln Thr
                610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Met Lys Gln Ile Glu Asp Lys Ile Glu Glu Ile Leu Ser
                660                 665                 670

Lys Ile Tyr His Ile Glu Asn Glu Ile Ala Arg Ile Lys Lys Leu Ile
                675                 680                 685

Gly Glu Val Gly Ser Gly Ala Pro Thr Lys Ala Lys Arg Arg Val Val
                690                 695                 700

Gln Arg Glu Lys Arg
705

<210> SEQ ID NO 31
<211> LENGTH: 867
<212> TYPE: PRT
<213> ORGANISM: Artificial Sequence
<220> FEATURE:
<223> OTHER INFORMATION: C1 sequence

<400> SEQUENCE: 31

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
                20                  25                  30

Leu Trp Val Thr Val Tyr Tyr Gly Val Pro Val Trp Lys Glu Ala Lys
                35                  40                  45

Thr Thr Leu Phe Cys Ala Ser Asp Ala Lys Ala Tyr Glu Lys Glu Val
                50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
                100                 105                 110

Gln Ser Leu Lys Pro Cys Val Lys Leu Thr Pro Leu Cys Val Thr Leu
```

```
            115                 120                 125
Glu Cys Arg Asn Val Arg Asn Val Ser Ser Asn Gly Thr Tyr Asn Ile
130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
                195                 200                 205

Ala Ile Thr Gln Ala Cys Pro Lys Val Ser Phe Asp Pro Ile Pro Ile
        210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
            260                 265                 270

Ser Leu Ala Glu Glu Ile Ile Ile Arg Ser Glu Asn Leu Thr Asn
            275                 280                 285

Asn Ala Lys Thr Ile Ile Val His Leu Asn Glu Thr Val Asn Ile Thr
290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Asn Phe
            355                 360                 365

Thr Ser Ser Ser Gly Gly Asp Leu Glu Ile Thr Thr His Ser Phe Asn
        370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
            420                 425                 430

Arg Ala Met Tyr Ala Pro Pro Ile Ala Gly Asn Ile Thr Cys Arg Ser
        435                 440                 445

Asn Ile Thr Gly Leu Leu Thr Arg Asp Gly Gly Ser Asn Asn Gly
        450                 455                 460

Val Pro Asn Asp Thr Glu Thr Phe Arg Pro Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Glu Arg
            500                 505                 510

Glu Lys Arg Ala Val Gly Ile Gly Ala Val Phe Leu Gly Ile Leu Gly
            515                 520                 525

Ala Ala Gly Ser Thr Met Gly Ala Ala Ser Ile Thr Leu Thr Val Gln
530                 535                 540
```

```
Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
            565                 570                 575

Ile Lys Gln Leu Gln Thr Arg Val Leu Ala Ile Glu Arg Tyr Leu Gln
                580                 585                 590

Asp Gln Gln Leu Leu Gly Leu Trp Gly Cys Ser Gly Lys Leu Ile Cys
            595                 600                 605

Thr Thr Ala Val Pro Trp Asn Thr Ser Trp Ser Asn Lys Ser Gln Thr
610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
            645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp Tyr Ile Lys Ile
            675                 680                 685

Phe Ile Met Ile Val Gly Gly Leu Ile Gly Leu Arg Ile Ile Phe Ala
            690                 695                 700

Val Leu Ser Ile Val Asn Arg Val Arg Gln Gly Tyr Ser Pro Leu Ser
705                 710                 715                 720

Leu Gln Thr Leu Thr Gln Asn Pro Gly Gly Leu Asp Arg Leu Gly Arg
                725                 730                 735

Ile Glu Glu Glu Gly Gly Glu Gln Asp Lys Asp Arg Ser Ile Arg Leu
            740                 745                 750

Val Asn Gly Phe Phe Ala Leu Phe Trp Asp Asp Leu Arg Ser Leu Cys
            755                 760                 765

Leu Phe Ser Tyr His Arg Leu Arg Asp Phe Ile Leu Ile Val Ala Arg
            770                 775                 780

Ala Val Glu Leu Leu Gly Arg Ser Ser Leu Arg Gly Leu Gln Arg Gly
785                 790                 795                 800

Trp Glu Ile Leu Lys Tyr Leu Gly Ser Leu Leu Gln Tyr Trp Gly Leu
                805                 810                 815

Glu Leu Lys Lys Ser Ala Ile Asn Leu Leu Asp Thr Ile Ala Ile Ala
            820                 825                 830

Val Ala Glu Gly Thr Asp Arg Ile Ile Glu Leu Ile Gln Arg Ile Cys
            835                 840                 845

Arg Ala Ile Cys Asn Ile Pro Arg Arg Ile Arg Gln Gly Phe Glu Ala
850                 855                 860

Ala Leu Gln
865

<210> SEQ ID NO 32
<211> LENGTH: 716
<212> TYPE: PRT
<213> ORGANISM: Artificial Sequence
<220> FEATURE:
<223> OTHER INFORMATION: C1D7 sequence

<400> SEQUENCE: 32

Met Arg Val Arg Gly Ile Gln Arg Asn Trp Pro Gln Trp Trp Ile Trp
1               5                   10                  15

Gly Ile Leu Gly Phe Trp Met Ile Ile Cys Arg Val Met Gly Asn
            20                  25                  30
```

-continued

```
Leu Trp Val Thr Val Tyr Tyr Gly Val Pro Val Trp Lys Glu Ala Lys
             35                  40                  45

Thr Thr Leu Phe Cys Ala Ser Asp Ala Lys Ala Tyr Glu Lys Glu Val
             50                  55                  60

His Asn Val Trp Ala Thr His Ala Cys Val Pro Thr Asp Pro Asn Pro
 65                  70                  75                  80

Gln Glu Met Val Leu Glu Asn Val Thr Glu Asn Phe Asn Met Trp Lys
                     85                  90                  95

Asn Asp Met Val Asp Gln Met His Glu Asp Ile Ile Arg Leu Trp Asp
                    100                 105                 110

Gln Ser Leu Lys Pro Cys Val Lys Leu Thr Pro Leu Cys Val Thr Leu
            115                 120                 125

Glu Cys Arg Asn Val Arg Asn Val Ser Ser Asn Gly Thr Tyr Asn Ile
        130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                    165                 170                 175

Arg Leu Asp Ile Val Pro Leu Asp Glu Asn Asn Ser Ser Glu Lys Ser
            180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                    245                 250                 255

Thr His Gly Ile Lys Pro Val Val Ser Thr Gln Leu Leu Leu Asn Gly
            260                 265                 270

Ser Leu Ala Glu Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                    325                 330                 335

Ala His Cys Asn Leu Ser Arg Asp Gly Trp Asn Lys Thr Leu Gln Gly
            340                 345                 350

Val Lys Lys Lys Leu Ala Glu His Phe Pro Asn Lys Thr Ile Asn Phe
        355                 360                 365

Thr Ser Ser Ser Gly Gly Asp Leu Glu Ile Thr Thr His Ser Phe Asn
370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                    405                 410                 415

Leu Pro Cys Arg Ile Lys Gln Ile Ile Asn Met Trp Gln Glu Val Gly
            420                 425                 430

Arg Ala Met Tyr Ala Pro Pro Ile Ala Gly Asn Ile Thr Cys Arg Ser
        435                 440                 445
```

Asn Ile Thr Gly Leu Leu Thr Arg Asp Gly Gly Ser Asn Asn Gly
            450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Arg
            500                 505                 510

Glu Lys Arg Ala Val Gly Ile Gly Ala Val Phe Leu Gly Ile Leu Gly
        515                 520                 525

Ala Ala Gly Ser Thr Met Gly Ala Ala Ser Ile Thr Leu Thr Val Gln
530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
        595                 600                 605

Thr Thr Ala Val Pro Trp Asn Thr Ser Trp Ser Asn Lys Ser Gln Thr
610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp Tyr Ile Lys Ile
        675                 680                 685

Phe Ile Met Ile Val Gly Gly Leu Ile Gly Leu Arg Ile Ile Phe Ala
        690                 695                 700

Val Leu Ser Ile Val Asn Arg Val Arg Gln Gly Tyr
705                 710                 715

<210> SEQ ID NO 33
<211> LENGTH: 2127
<212> TYPE: DNA
<213> ORGANISM: Artificial Sequence
<220> FEATURE:
<223> OTHER INFORMATION: nucleotide sequence encoding sC1

<400> SEQUENCE: 33
atgagagtgc ggggcattca gagaaactgg ccccagtggt ggatctgggg catcctgggc    60
ttttggatga tcattatctg ccgcgtgatg ggcaacctgt gggtcaccgt gtactacggc   120
gtgcccgtgt ggaaagaggc caagaccacc ctgttctgcg ccagcgacgc caaggcctac   180
gagaaagagg tgcacaacgt ctgggccacc cacgcctgtg tgcccaccga ccccaatccc   240
caggaaatgg tcctggaaaa cgtgaccgag aacttcaaca tgtggaagaa cgacatggtg   300
gaccagatgc acgaggacat catccggctg tgggaccaga gcctgaagcc ctgcgtgaag   360
ctgacccctc tgtgcgtgac cctggaatgc ggaacgtgc gcaacgtgtc cagcaacggc   420
acctacaata tcatccacaa cgagacatac aaagagatga agaactgcag cttcaacgct   480
accaccgtgg tcgaggaccg gaagcagaag gtgcacgccc tgttttaccg gctggacatc   540

```
gtgccctgg acgagaacaa cagcagcgag aagtcctccg agaacagctc cgagtactac    600
agactgatca actgcaacac cagcgccatc acccaggcct gccccaaggt gtccttcgac    660
cctatcccca tccactactg cgcccctgcc ggctacgcca tcctgaagtg caacaacaag    720
accttcaatg gcaccggccc ctgcaacaat gtgtccaccg tgcagtgcac ccacggcatc    780
aagcccgtgg tgtctaccca gctgctgctg aacggcagcc tggccgagga agagatcatc    840
atcagaagcg agaacctgac caacaacgcc aagacaatca tcgtccacct gaacgaaacc    900
gtgaacatca cctgtacccg gcctaacaac aacacccgga agtccatccg gatcggccct    960
ggccagacct tttacgccac cggcgatatt atcggcgaca tccggcaggc ccactgcaat   1020
ctgagccggg acggctggaa caagacactg cagggcgtca agaagaagct ggccgaacac   1080
ttccccaaca aaaccatcaa cttcaccagc tcctctggcg cgacctgga  aatcaccacc   1140 cacagcttta actgcagagg cgagttcttc tactgcaata cctccggcct gttcaatgga   1200
acctacatgc ccaacgggac caacagcaac tccagcagca atatcaccct gccttgccgg   1260
atcaagcaga ttatcaatat gtggcaggaa gtgggcagag ctatgtacgc ccctccaatc   1320
gccggcaaca tcacatgcag aagcaacatt accggcctgc tgctcaccag ggacggcggc   1380
tctaacaatg gcgtgccaaa cgacaccgag acattcagac ccggcggagg cgacatgcgg   1440
aacaattggc ggagcgagct gtacaagtac aaggtggtgg aagtgaagcc cctgggcgtg   1500
gcccctaccg aagccaagag aagagtggtc gaacgcgagg aacgggccgt gggcattgga   1560
gccgtgtttc tgggaatcct gggagccgct ggcagcacca tgggcgctgc ctctatcaca   1620
ctgacagtgc aggccagaca gctcctgagc ggcatcgtgc agcagcagag caacctgctg   1680
agagccatcg aggcacagca gcacatgctg cagctgaccg tgtgggcat  taagcagctc   1740 cagacacggg tgctggccat tgagagatac ctgcaggatc agcagctgct cggcctgtgg   1800
ggctgtagcg gcaagctgat ctgtaccacc gccgtgcctt ggaacaccct ctggtccaac   1860
aagagccaga ccgacatctg gacaacatg  acctggatgc agtgggacaa agaaatcggc   1920
aactataccg gcgagatcta ccgactgctg gaagagtccc agaaccagca ggaaaagatg   1980
aagcagatcg aggacaagat cgaagagatt ctgagcaaaa tctaccacat cgagaacgag   2040
atcgcccgca tcaagaaact gatcggcgaa gtgggatccg gcgctcccac aaaggccaaa   2100
agacgggtgg tgcagcgcga gaaacgc                                      2127
```

<210> SEQ ID NO 34
<211> LENGTH: 2601
<212> TYPE: DNA
<213> ORGANISM: Artificial Sequence
<220> FEATURE:
<223> OTHER INFORMATION: nucleotide sequence encoding C1

<400> SEQUENCE: 34

```
atgagagtgc ggggcattca gagaaactgg ccccagtggt ggatctgggg catcctgggc     60
ttttggatga tcattatctg ccgcgtgatg ggcaacctgt gggtcaccgt gtactacggc    120
gtgcccgtgt ggaaagaggc caagaccacc ctgttctgcg ccagcgacgc caaggcctac    180
gagaaagagg tgcacaacgt ctgggccacc cacgcctgtg tgcccaccga ccccaatccc    240
caggaaatgg tcctggaaaa cgtgaccgag aacttcaaca tgtggaagaa cgacatggtg    300
gaccagatgc acgaggacat catccggctg tgggaccaga gcctgaagcc ctgcgtgaag    360
ctgacccctc tgtgcgtgac cctggaatgc cggaacgtgc gcaacgtgtc cagcaacggc    420
acctacaata tcatccacaa cgagacatac aaagagatga agaactgcag cttcaacgct    480
```

```
accaccgtgg tcgaggaccg gaagcagaag gtgcacgccc tgttttaccg gctggacatc    540
gtgcccctgg acgagaacaa cagcagcgag aagtcctccg agaacagctc cgagtactac    600
agactgatca actgcaacac cagcgccatc acccaggcct gccccaaggt gtccttcgac    660
cctatcccca tccactactg cgcccctgcc ggctacgcca tcctgaagtg caacaacaag    720
accttcaatg gcaccggccc ctgcaacaat gtgtccaccg tgcagtgcac ccacggcatc    780
aagcccgtgg tgtctaccca gctgctgctg aacggcagcc tggccgagga agagatcatc    840
atcagaagcg agaacctgac caacaacgcc aagacaatca tcgtccacct gaacgaaacc    900
gtgaacatca cctgtacccg gcctaacaac aacacccgga agtccatccg gatcggccct    960
ggccagacct tttacgccac cggcgatatt atcggcgaca tccggcaggc ccactgcaat   1020
ctgagccggg acggctggaa caagacactg cagggcgtca agaagaagct ggccgaacac   1080
ttccccaaca aaaccatcaa cttcaccagc tcctctggcg gcgacctgga aatcaccacc   1140
cacagcttta actgcagagg cgagttcttc tactgcaata cctccggcct gttcaatgga   1200
acctacatgc ccaacgggac caacagcaac tccagcagca atatcaccct gccttgccgg   1260
atcaagcaga ttatcaatat gtggcaggaa gtgggcagag ctatgtacgc ccctccaatc   1320
gccggcaaca tcacatgcag aagcaacatt accggcctgc tgctcaccag ggacggcggc   1380
tctaacaatg gcgtgccaaa cgacaccgag acattcagac ccggcggagg cgacatgcgg   1440
aacaattggc ggagcgagct gtacaagtac aaggtggtgg aagtgaagcc cctgggcgtg   1500
gcccctaccg aagccaagag aagagtggtc gaacgcgaga gcgggccgt gggcattgga   1560 gccgtgtttc tgggaatcct gggagccgct ggcagcacca tgggcgctgc ctctatcaca   1620
ctgacagtgc aggccagaca gctcctgagc ggcatcgtgc agcagcagag caacctgctg   1680
agagccatcg aggcacagca gcacatgctg cagctgaccg tgtgggcat taagcagctc   1740 cagacacggg tgctggccat tgagagatac ctgcaggatc agcagctgct cggcctgtgg   1800
ggctgtagcg gcaagctgat ctgtaccacc gccgtgcctt ggaacacctc ctggtccaac   1860
aagagccaga ccgacatctg gacaacatg acctggatgc agtgggacaa agaaatcggc   1920
aactataccg gcgagatcta ccgactgctg gaagagtccc agaaccagca ggaaaagaac   1980
gagaaggacc tgctggccct ggacagctgg aaaaatctgt ggaattggtt cgacatcacc   2040
aactggctgt ggtacatcaa gatcttcatc atgatcgtgg cggcctgat cggcctgcgg   2100 atcatctttg ccgtgctgag catcgtgaac cgcgtgcggc agggatacag ccctctgagc   2160
ctgcagaccc tgacccagaa tccaggcgga ctggatcggc tgggccggat tgaggaagaa   2220
ggcggcgagc aggacaagga ccgcagcatc agactcgtga acggcttctt cgctctgttt   2280
tgggacgacc tgcggagcct gtgcctgttc tcctaccaca gactgcggga ctttatcctg   2340
attgtggcca gagccgtcga gctgctgggc agatcttctc tgagaggcct gcagcggggc   2400
tgggagattc tgaagtacct gggctcccg ctgcagtatt ggggcctgga actgaagaag   2460
tccgccatca atctgctcga cacaatcgct attgccgtgg ccgaaggcac cgacagaatc   2520
atcgagctga tccagcggat ctgccgggcc atctgcaaca tccccagacg gatcagacag   2580
ggctttgaag ccgccctcca g                                             2601
```

<210> SEQ ID NO 35
<211> LENGTH: 2148
<212> TYPE: DNA
<213> ORGANISM: Artificial Sequence
<220> FEATURE:

<223> OTHER INFORMATION: nucleotide sequence encoding C1D7

<400> SEQUENCE: 35

```
atgagagtgc ggggcattca gagaaactgg ccccagtggt ggatctgggg catcctgggc      60
ttttggatga tcattatctg ccgcgtgatg ggcaacctgt gggtcaccgt gtactacggc     120
gtgcccgtgt ggaaagaggc caagaccacc ctgttctgcg ccagcgacgc caaggcctac     180
gagaaagagg tgcacaacgt ctgggccacc cacgcctgtg tgcccaccga ccccaatccc     240
caggaaatgg tcctggaaaa cgtgaccgag aacttcaaca tgtggaagaa cgacatggtg     300
gaccagatgc acgaggacat catccggctg tgggaccaga gcctgaagcc ctgcgtgaag     360
ctgacccctc tgtgcgtgac cctggaatgc cggaacgtgc gcaacgtgtc cagcaacggc     420
acctacaata tcatccacaa cgagacatac aaagagatga gaactgcagc cttcaacgct     480
accaccgtgg tcgaggaccg gaagcagaag gtgcacgccc tgttttaccg gctggacatc     540
gtgcccctgg acgagaacaa cagcagcgag aagtcctccg agaacagctc cgagtactac     600
agactgatca actgcaacac cagcgccatc acccaggcct gccccaaggt gtccttcgac     660
cctatcccca tccactactg cgcccctgcc ggctacgcca tcctgaagtg caacaacaag     720
accttcaatg gcaccggccc ctgcaacaat gtgtccaccg tgcagtgcac ccacggcatc     780
aagcccgtgg tgtctaccca gctgctgctg aacggcagcc tggccgagga agagatcatc     840
atcagaagcg agaacctgac caacaacgcc aagacaatca tcgtccacct gaacgaaacc     900
gtgaacatca cctgtacccg gcctaacaac aacacccgga agtccatccg gatcggccct     960
ggccagacct tttacgccac cggcgatatt atcggcgaca tccggcaggc ccactgcaat    1020
ctgagccggg acggctggaa caagacactg caggcgtca gaagaagct ggccgaacac     1080
ttccccaaca aaaccatcaa cttcaccagc tcctctggcg cgacctgga aatcaccacc     1140
cacagcttta actgcagagg cgagttcttc tactgcaata cctccggcct gttcaatgga    1200
acctacatgc caacgggac caacagcaac tccagcagca atatcaccct gccttgccgg    1260
atcaagcaga ttatcaatat gtggcaggaa gtgggcagag ctatgtacgc ccctccaatc    1320
gccggcaaca tcacatgcag aagcaacatt accggcctgc tgctcaccag ggacggcggc    1380
tctaacaatg gcgtgccaaa cgacaccgag acattcagac ccggcggagg cgacatgcgg    1440
aacaattggc ggagcgagct gtacaagtac aaggtggtgg aagtgaagcc cctgggcgtg    1500
gcccctaccg aagccaagag aagagtggtc gaacgcgaga gcgggccgt gggcattgga    1560
gccgtgtttc tgggaatcct gggagccgct ggcagcacca tgggcgctgc ctctatcaca    1620
ctgacagtgc aggccagaca gctcctgagc ggcatcgtgc agcagcagag caacctgctg    1680
agagccatcg aggcacagca gcacatgctg cagctgaccg tgtggggcat taagcagctc    1740
cagacacggg tgctggccat tgagagatac ctgcaggatc agcagctgct cggcctgtgg    1800
ggctgtagcg gcaagctgat ctgtaccacc gccgtgcctt ggaacacctc ctggtccaac    1860
aagagccaga ccgacatctg gacaacatg acctggatgc agtgggacaa agaaatcggc    1920
aactataccg gcgagatcta ccgactgctg gaagagtccc agaaccagca ggaaaagaac    1980
gagaaggacc tgctggccct ggacagctgg aaaaatctgt ggaattggtt cgacatcacc    2040
aactggctgt ggtacatcaa gatcttcatc atgatcgtgg gcggcctgat cggcctgcgg    2100
atcatctttg ccgtgctgag catcgtgaac cgcgtgcggc agggctac                 2148
```

<210> SEQ ID NO 36
<211> LENGTH: 724

```
<212> TYPE: PRT
<213> ORGANISM: Artificial Sequence
<220> FEATURE:
<223> OTHER INFORMATION: mosaic Env trimer sequence

<400> SEQUENCE: 36

Met Arg Val Arg Gly Ile Gln Arg Asn Cys Gln His Leu Trp Arg Trp
1               5                   10                  15

Gly Thr Leu Ile Leu Gly Met Leu Met Ile Cys Ser Ala Ala Gly Lys
            20                  25                  30

Leu Trp Val Thr Val Tyr Tyr Gly Val Pro Val Trp Lys Glu Ala Thr
            35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Asn Ala Thr Asn Thr
130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
            180                 185                 190

Asn Thr Asn Tyr Arg Leu Ile Ser Cys Asn Thr Ser Val Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
        275                 280                 285

Ile Met Val Gln Leu Asn Val Ser Val Glu Ile Asn Cys Thr Arg Pro
    290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
                325                 330                 335

Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
        355                 360                 365

Ser Gly Gly Asp Pro Glu Ile Val Met His Ser Phe Asn Cys Gly Gly
    370                 375                 380
```

Glu Phe Phe Tyr Cys Asn Ser Thr Lys Leu Phe Asn Ser Thr Trp Thr
385                 390                 395                 400

Trp Asn Asn Ser Thr Trp Asn Asn Thr Lys Arg Ser Asn Asp Thr Glu
            405                 410                 415

Glu His Ile Thr Leu Pro Cys Arg Ile Lys Gln Ile Ile Asn Met Trp
            420                 425                 430

Gln Glu Val Gly Lys Ala Met Tyr Ala Pro Pro Ile Arg Gly Gln Ile
            435                 440                 445

Arg Cys Ser Ser Asn Ile Thr Gly Leu Leu Thr Arg Asp Gly Gly
450                 455                 460

Asn Asp Thr Ser Gly Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
            485                 490                 495

Glu Pro Leu Gly Val Ala Pro Thr Lys Ala Lys Glu Arg Val Val Gln
            500                 505                 510

Arg Glu Glu Arg Ala Val Gly Ile Gly Ala Val Phe Leu Gly Phe Leu
            515                 520                 525

Gly Ala Ala Gly Ser Thr Met Gly Ala Ala Ser Met Thr Leu Thr Val
530                 535                 540

Gln Ala Arg Leu Leu Leu Ser Gly Ile Val Gln Gln Asn Asn Leu
545                 550                 555                 560

Leu Arg Ala Ile Glu Ala Gln Gln His Leu Leu Gln Leu Thr Val Trp
            565                 570                 575

Gly Ile Lys Gln Leu Gln Ala Arg Val Leu Ala Val Glu Arg Tyr Leu
            580                 585                 590

Lys Asp Gln Gln Leu Leu Gly Ile Trp Gly Cys Ser Gly Lys Leu Ile
            595                 600                 605

Cys Thr Thr Thr Val Pro Trp Asn Ala Ser Trp Ser Asn Lys Ser Leu
610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
            645                 650                 655

Gln Gln Glu Lys Asn Glu Gln Glu Leu Leu Glu Leu Asp Lys Trp Ala
            660                 665                 670

Ser Leu Trp Asn Trp Phe Asp Ile Ser Asn Trp Leu Trp Tyr Ile Lys
            675                 680                 685

Ser Arg Ile Glu Gly Arg Gly Ser Gly Gly Tyr Ile Pro Glu Ala Pro
            690                 695                 700

Arg Asp Gly Gln Ala Tyr Val Arg Lys Asp Gly Glu Trp Val Leu Leu
705                 710                 715                 720

Ser Thr Phe Leu

<210> SEQ ID NO 37
<211> LENGTH: 28
<212> TYPE: PRT
<213> ORGANISM: Artificial Sequence
<220> FEATURE:
<223> OTHER INFORMATION: Residues 655-682 of SEQ ID NO:18

```
<400> SEQUENCE: 37

Asn Glu Lys Asp Leu Leu Ala Leu Asp Ser Trp Asn Asn Leu Trp Asn
1               5                   10                  15

Trp Phe Ser Ile Ser Lys Trp Leu Trp Tyr Ile Lys
            20                  25
```

RECOMBINANT ADENOVIRUSES ENCODING MOSAIC HUMAN IMMUNODEFICIENCY VIRUS (HIV) ENV, GAG, AND POL ANTIGENS

CROSS REFERENCE TO RELATED APPLICATIONS

This application is a divisional of U.S. patent application Ser. No. 15/380,123, filed on Dec. 15, 2016, which claims priority under 35 U.S.C. § 119(b) to European Patent Application No. EP 16194124.0, filed on Oct. 17, 2016, and European Patent Application No. EP 15200138.4, filed on Dec. 15, 2016, the disclosures of which are incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "688097-106U1 Sequence Listing" and a creation date of Apr. 7, 2019, and having a size of 156 kB. The sequence listing submitted via EFS-Web is part of the specification and is herein incorporated by reference in its entirety.

BACKGROUND OF THE INVENTION

Human Immunodeficiency Virus (HIV) affects millions of people worldwide, and the prevention of HIV through an efficacious vaccine remains a very high priority, even in an era of widespread antiretroviral treatment. HIV-1 is the most common and pathogenic strain of the virus, with more than 90% of HIV/AIDS cases deriving from infection with HIV-1 group M. The M group is subdivided further into clades or subtypes. An efficacious vaccine ideally would be capable of eliciting both potent cellular responses and broadly neutralizing antibodies capable of neutralizing HIV-1 strains from different clades.

The high genetic variability of HIV-1 makes the development of a HIV-1 vaccine an unprecedented challenge. In order to improve coverage of potential T-cell epitopes, and improve cellular responses, "mosaic" HIV-1 Gag, Pol and Env antigens, derived from HIV Group Antigen (Gag), Polymerase (Pol), and Envelope (Env) proteins, were described by others and developed in an attempt to provide maximal coverage of potential T-cell epitopes (e.g., Barouch et al, Nat Med 2010, 16: 319-323). The mosaic antigens are similar in length and domain structure to wild-type, naturally occurring HIV-1 antigens.

For example, mosaic HIV antigens described and used in vaccines include those described in Barouch et al, supra, and WO 2010/059732 such as:
 (a) Gag mosaic antigens including:
  (a)(i) a first mosaic Gag sequence ("mos1Gag") having the amino acid sequence as set forth herein in SEQ ID NO: 1, and
  (a)(ii) a second mosaic Gag sequence ("mos2Gag") having the amino acid sequence as set forth herein in SEQ ID NO: 2;
 (b) Pol mosaic antigens including:
  (b)(i) a first mosaic Pol sequence ("mos1Pol") having the amino acid sequence as set forth herein in SEQ ID NO: 3, and
  (b)(ii) a second mosaic Pol sequence ("mos2Pol") having the amino acid sequence as set forth herein in SEQ ID NO: 4; and
 (c) Env mosaic antigens including:
  (c)(i) a first mosaic Env sequence ("mos1Env") having the amino acid sequence as set forth herein in SEQ ID NO: 5, and
  (c)(ii) a second mosaic Env sequence ("mos2Env") having the amino acid sequence as set forth herein in SEQ ID NO: 6.

Sequences encoding these antigens have been cloned in vectors, for example, such as recombinant adenoviral vectors, e.g., recombinant adenovirus serotype 26 (rAd26), and these recombinant vectors were previously used as vaccines to generate immune responses to the antigens (see e.g. Barouch et al, supra; and WO 2010/059732). For example, the mos1Gag and mos1Pol mosaic antigen sequences are typically combined into a fusion protein of Gag and Pol ("mos1GagPol"), and the coding sequence of which is cloned into a first Ad26 vector ("rAd26.mos1GagPol"); and the mos2Gag and mos2Pol antigen sequences are combined into another fusion protein of Gag and Pol ("mos2GagPol"), and the coding sequence of which is cloned into a second Ad26 vector ("rAd26.mos2GagPol"). Constructs encoding mos1Env and mos2Env are typically cloned into separate Ad26 vectors ("rAd26.mos1Env" and "rAd26.mos2Env", respectively).

A set of such mosaic antigens as described above gives good global coverage of Group M HIV-1 isolates, where rAd26 vectors encoding mosaic 1 antigen sequences (e.g., rAd26.mos1GagPol and rAd26.mos1Env) favor clade B and CRF01 HIV-1 subtypes, and rAd26 vectors encoding mosaic 2 antigen sequences (e.g., rAd26.mos2GagPol and rAd26.mos2Env) favor clade C strains. Mosaic HIV-1 Gag, Pol, and Env antigens expressed in rAd26 vectors can be used to improve both the breadth and depth of antigen-specific T-lymphocyte responses in rhesus monkeys, without compromising the magnitude of both cellular and humoral responses when compared with consensus or natural sequence HIV-1 antigens (Barouch et al, supra; and WO 2010/059732).

However, upon further development efforts on the vaccine components described above, it was found that rAd26.mos2Env showed non-optimal cell surface expression and immune response in non-human primates, but moreover displayed a hitherto unreported, unexpected and unpredictable non-optimal genetic stability during the manufacturing process as compared to the other rAd26 vectors, such as rAd26.mos1Env. Thus, vaccines containing rAd26.mos2Env may result in non-optimal immune responses against Clade C HIV-1 subtypes, since the mos2Env mosaic antigen favors clade C HIV-1 strains. Accordingly, there is a need for an alternative to the mos2Env antigen in vaccines against HIV that can be used to induce improved immune responses against HIV-1 clade C.

BRIEF SUMMARY OF THE INVENTION

The invention relates to novel synthetic human immunodeficiency virus (HIV) envelope proteins that have improved cell surface expression and genetic stability as compared to the previously described mos2Env antigen. The invention also relates to compositions and methods of using such novel synthetic HIV envelope proteins and/or coding sequences thereof to induce increased immune responses against HIV-1, particularly HIV-1 clade C, preferably when used in combination with other HIV antigens.

In one general aspect, the invention relates to a nucleic acid encoding a synthetic HIV envelope protein comprising the amino acid sequence of SEQ ID NO: 8, or SEQ ID NO: 8 having one or more mutations selected from the group consisting of (i) I529P (i.e., a substitution of Ile to Pro at position 529 of SEQ ID NO:8), (ii) K480E (i.e., a substitution of Lys to Glu at position 480 of SEQ ID NO:8), and (iii) a combination of EK479-480RRRR (i.e. a replacement of Glu-Lys at positions 479-480 of SEQ ID NO:8 with four consecutive Arg residues), I529P, A471C (i.e., a substitution of Ala to Cys at position 471 of SEQ ID NO:8) and T575C (i.e., a substitution of Thr to Cys at position 575 of SEQ ID NO:8). In one embodiment, the synthetic HIV envelope protein further comprises a signal sequence, for instance a signal sequence having the amino acid sequence selected from the group consisting of SEQ ID NOs: 9-12. In one embodiment, the signal sequence has the amino acid sequence of SEQ ID NO: 9.

In certain embodiments, the synthetic HIV envelope protein further comprises a transmembrane domain, preferably a transmembrane domain having the amino acid sequence of SEQ ID NO: 13.

In certain embodiments, the synthetic HIV envelope protein further comprises a fragment of a cytoplasmic domain, preferably a fragment of a cytoplasmic domain comprising the amino acid sequence of SEQ ID NO: 14, or amino acids 1-4 thereof (i.e., NRVR). In embodiments wherein the synthetic HIV envelope protein further comprises a transmembrane domain and a fragment of a cytoplasmic domain, it is preferred that the protein also comprises the amino acid sequence of SEQ ID NO: 37, which is fused to the carboxyl-terminus (C-terminus) of SEQ ID NO: 8 and the amino-terminus (N-terminus) of the transmembrane region.

In another embodiment, the synthetic HIV envelope protein comprises a trimerization domain, for instance, a trimerization domain comprising the amino acid sequence of SEQ ID NO: 15 (GCN4) or SEQ ID NO: 16 (foldon domain). In one preferred embodiment, the trimerization domain comprises the amino acid sequence of SEQ ID NO: 15. Such embodiments with trimerization domains are useful for soluble (i.e. non membrane-bound) synthetic HIV envelope proteins based on the ectodomain sequences provided herein, such as that comprising the amino acid sequence of SEQ ID NO: 8, wherein the trimerization domain is located at the C-terminus of the synthetic HIV envelope protein.

In yet other embodiments, the synthetic HIV envelope protein comprises SEQ ID NO: 8 with the following mutations: EK479-480RRRR, I529P, A471C and T575C. The introduction of 6 consecutive arginine residues (positions 478 and 481 in the native sequence of SEQ ID NO: 8 already are Arg residues) results in a further optimized furin cleavage site, so that an improved processed (i.e., cleaved) ectodomain is obtained. The three mutations of I529P, A471C and T575C are known as SOSIP mutations, wherefrom the last two mutations result in introduction of a possible disulfide bridge between the newly created cysteine residues. Overall, these mutations result in a soluble, trimerized, synthetic HIV envelope protein, without necessity for a trimerization domain.

In a preferred embodiment, the invention relates to a nucleic acid encoding a synthetic HIV envelope protein comprising the amino acid sequence of SEQ ID NO: 17, SEQ ID NO: 18, or aa 1-686 of SEQ ID NO: 19. Most preferably the synthetic HIV envelope protein encoded by the nucleic acid comprises or consists of the amino acid sequence of SEQ ID NO: 18.

In another general aspect, the invention relates to a vector comprising a nucleic acid encoding a synthetic HIV envelope protein according to an embodiment of the invention. In one embodiment, the vector is a viral vector. In a preferred embodiment, the viral vector is an adenoviral vector. In one preferred embodiment, the adenoviral vector is an adenovirus 26 vector.

Another general aspect of the invention relates to a composition, preferably a vaccine composition, comprising an immunogenically effective amount of a vector according to an embodiment of the invention, and a carrier, wherein the nucleic acid encoding the synthetic HIV envelope protein is operably linked to a promoter sequence. In one embodiment, the composition comprises an adenovirus vector, preferably an adenovirus 26 vector, encoding a synthetic HIV envelope protein comprising the amino acid sequence of SEQ ID NO: 18.

In another general aspect, the invention relates to a vaccine combination for inducing an immune response against a human immunodeficiency virus (HIV) in a subject in need thereof. The vaccine combination comprises a first composition comprising an immunogenically effective amount of a vector, preferably an adenovirus vector, more preferably an adenovirus 26 vector, encoding a synthetic HIV envelope protein having the amino acid sequence of SEQ ID NO: 18, a second composition comprising an immunogenically effective amount of a second vector, preferably a second adenovirus vector, more preferably a second adenovirus 26 vector, encoding an HIV antigenic polypeptide comprising the amino acid sequence of SEQ ID NO: 5, and optionally at least one additional composition comprising an immunogenically effective amount of at least one selected from the group consisting of a vector encoding an antigenic polypeptide having the amino acid sequence selected from the group consisting of SEQ ID NOs: 1-4, 28 and 29, and a polypeptide comprising an immunogenically effective amount of an isolated HIV antigenic polypeptide, including but not limited to, a polypeptide having residues 30-708 of the amino acid sequence of SEQ ID NO: 7, or a polypeptide having residues 30-724 of SEQ ID NO:36, wherein the first composition, second composition and optional additional composition are present in the same composition or in one or more different compositions.

Yet another general aspect of the invention relates to methods of inducing an immune response against a human immunodeficiency virus (HIV) in a subject in need thereof, comprising administering to the subject a composition or vaccine combination according to an embodiment of the invention. The invention also relates to methods of inducing an immune response against an HIV comprising priming and boosting the immune response using a composition or a vaccine combination according to an embodiment of the invention.

Yet a further aspect of the invention relates to a synthetic HIV envelope protein comprising the amino acid sequence of SEQ ID NO: 8, or SEQ ID NO: 8 having one or more mutations selected from the group consisting of (i) I529P, (ii) K480E, (iii) a combination of EK479-480RRRR, I529P, A471C and T575C. In one embodiment, the synthetic HIV envelope protein comprises SEQ ID NO: 8 with the mutations of EK479-480RRRR, I529P, A471C and T575C. In another embodiment, the synthetic HIV envelope protein comprises residues 30-704 or 30-711 of the amino acid sequence of SEQ ID NO: 18. In yet another embodiment the synthetic HIV envelope protein comprises residues 30-686 of the amino acid sequence of SEQ ID NO: 19.

Another aspect of the invention relates to a cell, preferably an isolated cell, comprising a vector according to an embodiment of the invention.

BRIEF DESCRIPTION OF THE SEVERAL VIEWS OF THE DRAWINGS

The foregoing summary, as well as the following detailed description of the invention, will be better understood when read in conjunction with the appended drawings. It should be understood that the invention is not limited to the precise embodiments shown in the drawings.

In the drawings:

FIGS. 1A-1C are schematic representations of the structure of HIV envelope proteins; FIG. 1A shows a full length HIV envelope protein; FIG. 1B shows the structure of a soluble single chain HIV envelope protein according to an embodiment of the invention in which the transmembrane domain (TM) is replaced with a GCN4 trimerization domain, and the furin cleavage site is mutated (sC4); FIG. 1C shows the structure of a membrane bound HIV envelope protein according to an embodiment of the invention comprising a transmembrane domain and a fragment of a cytoplasmic domain (C4D7);

FIG. 3A shows binding of sC1; FIG. 3B shows binding of sC4;

FIG. 7A shows the results with VSV-G (negative control); and FIG. 7B shows the results with MW965.26 (Tier 1A clade C).

DETAILED DESCRIPTION OF THE INVENTION

Figure 2:
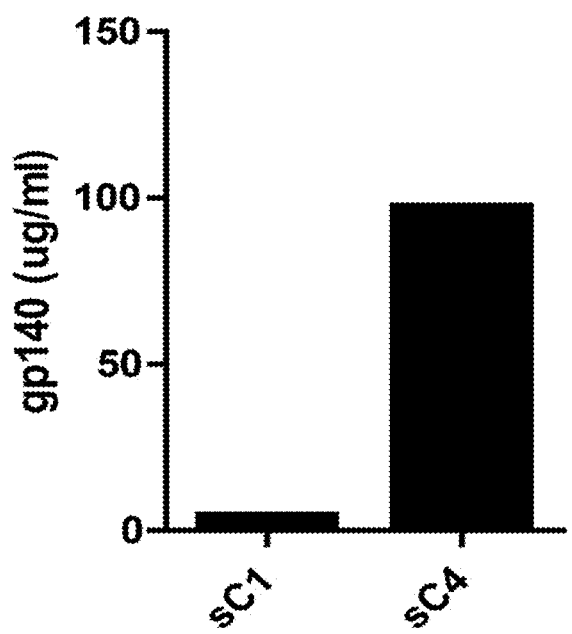
FIG. 2 shows expression levels of the soluble sC1 envelope protein, which is based on the mos2Env mosaic antigen sequence with an additional C-terminal trimerization domain, and a soluble synthetic HIV envelope protein (sC4) according to an embodiment of the invention; expression was measured by quantitative Western blot using a polyclonal antibody against gp120; plasmids encoding sC1 or sC4 were transiently expressed twice, and each transfection was quantified twice by densitometry; the sC1 protein showed very low expression levels compared to the sC4 synthetic HIV envelope protein, which showed relatively high expression levels.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

As used herein, "subject" means any animal, preferably a mammal, most preferably a human, to whom will be or has been administered a vector, composition or combination vaccine according to embodiments of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The invention generally relates to synthetic HIV envelope proteins, nucleic acid and vectors encoding the synthetic HIV envelope proteins, and methods of inducing an immune response against HIV with vectors encoding the synthetic HIV envelope proteins or the synthetic HIV envelope proteins, alone or in combination with one or more additional vectors encoding one or more additional HIV antigenic polypeptides and/or in combination with one or more additional isolated HIV antigenic polypeptides.

Human immunodeficiency virus (HIV) is a member of the genus Lentivirinae, which is part of the family of Retroviridae. Two species of HIV infect humans: HIV-1 and HIV-2. HIV-1 is the most common strain of HIV virus, and is known to be more pathogenic than HIV-2. As used herein, the terms "human immunodeficiency virus" and "HIV" refer, but are not limited to, HIV-1 and HIV-2.

HIV is categorized into multiple clades with a high degree of genetic divergence. As used herein, the term "HIV clade" or "HIV subtype" refers to related human immunodeficiency viruses classified according to their degree of genetic similarity. There are currently three groups of HIV-1 isolates: M, N and O. Group M (major strains) consists of at least ten clades, A through J. Group O (outer strains) can consist of a similar number of clades. Group N is a new HIV-1 isolate that has not been categorized in either group M or O.

As used herein, the terms "HIV antigenic polypeptide," "HIV antigenic protein," and "HIV immunogen" refer to a polypeptide capable of inducing an immune response, e.g., a humoral and/or cellular mediated response, against HIV in a subject. The antigenic polypeptide can be a protein of the HIV, a fragment or epitope thereof, or a combination of multiple HIV proteins or portions thereof, that can induce an immune response or produce an immunity, e.g., protective immunity, against the HIV in a subject.

Preferably, an antigenic polypeptide is capable of raising in a host a protective immune response, e.g., inducing an immune response against a viral disease or infection, and/or producing an immunity in (i.e., vaccinates) a subject against a viral disease or infection, that protects the subject against the viral disease or infection. For example, the antigenic polypeptide can comprise a protein or fragments thereof from Simian Immunodeficiency Virus (SIV) or an HIV, such as the HIV or SIV envelope gp160 protein, the HIV or SIV matrix/capsid proteins, and the HIV or SIV gag, pol and env gene products.

An HIV antigenic polypeptide can be any HIV-1 or HIV-2 antigen or fragment thereof. Examples of HIV antigens include, but are not limited to gag, pol, and env gene products, which encode structural proteins and essential enzymes. Gag, pol, and env gene products are synthesized as polyproteins, which are further processed into multiple other protein products. The primary protein product of the gag gene is the viral structural protein gag polyprotein, which is further processed into MA, CA, SP1, NC, SP2, and P6 protein products. The pol gene encodes viral enzymes (Pol, polymerase), and the primary protein product is further processed into RT, RNase H, IN, and PR protein products. The env gene encodes structural proteins, specifically glycoproteins of the virion envelope. The primary protein product of the env gene is gp160, which is further processed into gp120 and gp41. Other examples of HIV antigens include gene regulatory proteins Tat and Rev; accessory proteins Nef, Vpr, Vif and Vpu; capsid proteins, nucleocapsid proteins, and p24 viral protein.

In certain embodiments, the HIV antigenic polypeptide comprises an HIV Gag, Env, or Pol antigen, or any antigenic portion or epitope or combination thereof, preferably an HIV-1 Gag, Env, or Pol antigen or any antigenic portion or epitope or combination thereof.

HIV antigenic polypeptides can also be mosaic HIV antigens. As used herein, "mosaic antigen" refers to a recombinant protein assembled from fragments of natural sequences. Mosaic antigens resemble natural antigens, but are optimized to maximize the coverage of potential T-cell epitopes found in the natural sequences, which improves the breadth and coverage of the immune response. Mosaic HIV antigens for use with the invention are preferably mosaic Gag, Pol, and/or Env antigens, and more preferably a mosaic HIV-1 Gag, Pol, and/or Env antigens. As used herein, "a mosaic HIV Gag, Pol, and/or Env antigen" specifically refers to a mosaic antigen comprising multiple epitopes derived from one or more of the Gag, Pol and/or Env polyprotein sequences of HIV.

In one embodiment, a mosaic HIV antigen for use with the invention is a mosaic HIV Gag antigen with epitopes derived from the sequences of gag gene products (examples are provided in SEQ ID NOs: 1, 2); a mosaic HIV Pol antigen with epitopes derived from the sequences of pol gene products (examples are provided in SEQ ID NOs: 3, 4); or a mosaic HIV Env antigen with epitopes derived from the sequences of env gene products (examples are provided in SEQ ID NOs: 5, 6; also the novel antigens of the invention, e.g. in SEQ ID NOs: 8, 17, 18, 19, can be considered mosaic HIV Env antigens). In certain embodiments, a mosaic HIV antigen for use with the invention may comprise a combination of epitopes derived from sequences of gag, pol, and/or env gene products. Illustrative and non-limiting examples include mosaic Env-Pol antigens with epitopes derived from the sequences of env and pol gene products; mosaic Gag-Pol antigens with epitopes derived from the sequences of gag and pol gene products; and mosaic Gag-Env antigens with epitopes derived from the sequences of gag and env gene products. The sequences of gag, pol, and env gene products can be derived from one or more clades.

Examples of mosaic HIV Gag, Pol and/or Env antigens that can be used in the invention include those described in, e.g., US20120076812; Barouch et al., *Nat Med* 2010, 16:319-323; and Barouch et al., *Cell* 155:1-9, 2013, all of which are incorporated herein by reference in their entirety. Preferably, mosaic HIV Gag, Pol, and/or Env antigens for use with the present invention include, but are not limited to, mos1Gag (SEQ ID NO: 1), mos2Gag (SEQ ID NO: 2), mos1Pol (SEQ ID NO: 3), mos2Pol (SEQ ID NO: 4), mos1Env (SEQ ID NO: 5), mos2Env (SEQ ID NO: 6), mos1GagPol (SEQ ID NO: 28), mos2GagPol (SEQ ID NO: 29), and combinations thereof.

As used herein, each of the terms "HIV envelope protein," "env protein," and "Env" refers to a protein that is expressed on the envelope of an HIV virion and enables an HIV to target and attach to the plasma membrane of HIV infected cells, or a fragment or derivative thereof that can induce an immune response or produce an immunity against the HIV in a subject in need thereof. The HIV env gene encodes the precursor protein gp160, which is proteolytically cleaved into the two mature envelope glycoproteins, gp120 and gp41. The cleavage reaction is mediated by a host cell protease, furin, at a sequence highly conserved in retroviral envelope glycoprotein precursors. More specifically, gp160 trimerizes to $(gp160)_3$ and then undergoes cleavage into the two noncovalently associated gp120 and gp41. Viral entry is subsequently mediated by a trimer of gp120/gp41 heterodimers. Gp120 is the receptor binding fragment, and binds to the CD4 receptor on a target cell that has such a receptor, such as, e.g., a T-helper cell. Gp41, which is noncovalently bound to gp120, is the fusion fragment and provides the second step by which HIV enters the cell. Gp41 is originally buried within the viral envelope, but when gp120 binds to a CD4 receptor, gp120 changes its conformation causing gp41 to become exposed, where it can assist in fusion with the host cell. Gp140 is the uncleaved ectodomain of trimeric gp160, i.e., $(gp160)_3$, that has been used as a surrogate for the native state of the cleaved, viral spike.

According to embodiments of the invention, an "HIV envelope protein" can be a gp160, gp140, gp120, gp41 protein, combinations, fusions, truncations or derivatives thereof. For example, an "HIV envelope protein" can include a gp120 protein noncovalently associated with a gp41 protein. It can also include a stabilized trimeric gp140 protein that can have or can be modified to include a trimerization domain that stabilizes trimers of gp140. Examples of trimerization domains include, but are not limited to, the T4-fibritin "foldon" trimerization domain; the coiled-coil trimerization domain derived from GCN4; and the catalytic subunit of *E. coli* aspartate transcarbamoylase as a trimer tag. An "HIV envelope protein" can also be a truncated HIV envelope protein including, but not limited to, envelope proteins comprising a C-terminal truncation in the ectodomain (i.e. the domain that extends into the extracellular space), a truncation in the gp41, such as a truncation in the transmembrane domain of gp41, or a truncation in the cytoplasmic domain of gp41. An "HIV envelope protein" can further be a derivative of a naturally occurring HIV envelope protein having sequence mutations, e.g., in the furin cleavage sites, and/or so-called SOSIP mutations.

Preferably, an "HIV envelope protein" is a "synthetic HIV envelope protein." As used herein, the term "synthetic HIV envelope protein" refers to a non-naturally occurring HIV envelope protein that is optimized to induce an immune response or produce an immunity against one or more naturally occurring HIV strains in a subject in need thereof. Mosaic HIV Env proteins are examples of synthetic HIV Env proteins, and the invention provides novel synthetic HIV Env antigens, e.g. the ones comprising SEQ ID NOs: 8, 17, 18, or 19.

Synthetic HIV Envelope Proteins and Coding Sequences Thereof

Embodiments of the invention relate to novel synthetic HIV envelope proteins and nucleic acid molecules encoding these.

In one embodiment, the invention relates to a synthetic HIV envelope protein comprising the amino acid sequence of SEQ ID NO: 8, or SEQ ID NO: 8 having one or more mutations selected from the group consisting of (i) I529P, (ii) K480E, and (iii) a combination of EK479-480RRRR, I529P, A471C and T575C. SEQ ID NO: 8 comprises a synthetic mature gp120 and a synthetic truncated gp41 without the transmembrane region, nor the cytoplasmic domain. SEQ ID NO: 8 is a non-naturally occurring sequence comprised of a chimera of sequences from the mos2Env mosaic antigen (SEQ ID NO: 6), and other HIV envelope protein sequences. The sequence of the novel synthetic Env antigen comprising SEQ ID NO: 8 is optimized to provide broad coverage and an enhanced T-cell response against HIV clade C (as compared to the mos2Env antigen (SEQ ID NO: 6)). In certain embodiments, further amino acids can be added to SEQ ID NO: 8 or one of its variants defined herein.

In certain embodiments, the synthetic HIV envelope protein further comprises a signal sequence. The synthetic HIV envelope protein is synthesized with a signal sequence that is cleaved from the nascent polypeptide chain during its transport into the lumen of the endoplasmic reticulum (ER). In principle, any known signal sequence could be used. Preferably an HIV Env signal sequence or a variant thereof is used. Different signal sequences have been used in the art for HIV Env proteins (see e.g. WO 2014/107744). In certain embodiments, the signal sequence comprises SEQ ID NO:9, SEQ ID NO: 10, SEQ ID NO:11 or SEQ ID NO:12. In one preferred embodiment, the signal sequence comprises SEQ ID NO: 9.

In certain embodiments, the synthetic HIV envelope protein further comprises a transmembrane domain. The transmembrane domain anchors the synthetic HIV envelope protein to the ER membrane, and contributes to membrane assembly and function of the HIV envelope. Preferably, the transmembrane domain comprises SEQ ID NO: 13.

In another embodiment, the synthetic HIV envelope protein comprises a gp41 having a truncated cytoplasmic domain. The gp41 has an unusually long cytoplasmic domain at its carboxyl end, typically about 150 amino acids (Edwards et al., *J. Virology*, 2002, 76:2683-2691). Truncation of the cytoplasmic domain was reported to induce exposure of conserved regions in the ectodomain of HIV-1 Env protein (Id.). The truncated cytoplasmic domain in a synthetic HIV envelope of the invention can range from one to about 140 amino acids, such as 1, 2, 3, 4, 5, 6, 7, 8, 9, 10, 15, 20, 30, 40, 50, 60, 70, 80, 90, 100, 110, 120, 130, or 140 amino acids of a full-length cytoplasmic domain. In certain embodiments the truncated cytoplasmic domain is derived from amino acids 704-862 of SEQ ID NO: 17 (i.e. from the cytoplasmic domain of the C4 molecule of the invention), by truncation after a given amino acid up to the C-terminus. In a preferred embodiment, the synthetic HIV envelope protein comprises a truncated cytoplasmic domain having 1 to 10 amino acids residues, more preferably 4 to 8 amino acid residues, and most preferably 7 amino acid residues of an HIV gp41 cytoplasmic domain. The cytoplasmic domain or fragment thereof of a synthetic HIV envelope protein is located C-terminal to the extracellular domain (ectodomain), and when the synthetic HIV envelope protein also comprises a transmembrane domain, the cytoplasmic domain or fragment thereof is located C-terminal to the transmembrane domain. See, e.g., FIGS. 1A and 1C. In a particular embodiment, the synthetic HIV envelope protein comprises a gp41 with a truncated cytoplasmic domain having the amino acid sequence of SEQ ID NO: 14 or a fragment thereof, such as residues 1-4 thereof (i.e. NRVR). Other truncated cytoplasmic domains have been described and could be used (e.g. Schiernle et al., *PNAS* 1997; Abrahamyan et al., *J Virol* 2005).

In embodiments wherein the synthetic HIV envelope protein further comprises a transmembrane domain and a fragment of a cytoplasmic domain, it is preferred that the protein also comprises the amino acid sequence of SEQ ID NO: 37, which contains residues 655-682 of SEQ ID NO: 18, wherein the amino acid sequence of SEQ ID NO: 37 is fused to the C-terminus of SEQ ID NO: 8 and the N-terminus of the transmembrane domain.

In a particularly preferred embodiment of the invention, the synthetic HIV envelope protein further comprises a transmembrane domain, such as that having the amino acid sequence of SEQ ID NO: 13, and a truncated cytoplasmic domain or a fragment of a cytoplasmic domain, such as that having the amino acid sequence of SEQ ID NO: 14 or residues 1-4 of SEQ ID NO: 14 (i.e., NRVR). Most preferably, the synthetic HIV envelope protein comprises or consists of the amino acid sequence of SEQ ID NO: 18, with or without the signal sequence (i.e., amino acid resides 1-29 of SEQ ID NO: 18).

In another embodiment, the synthetic HIV envelope protein comprises a trimerization domain that replaces an Env transmembrane region. The trimerization domain increases the stability of an Env trimeric structure. Preferably, the synthetic HIV envelope protein comprises a gp140 polypeptide that is modified to include a trimerization domain that stabilizes trimers of gp140. Examples of trimerization domains include, but are not limited to, the T4-fibritin "foldon" trimerization domain, such as that comprising the amino acid sequence of SEQ ID: 16; the coiled-coil trimerization domain derived from GCN4, such as that comprising the amino acid sequence of SEQ ID:15; the catalytic subunit of *E. coli* aspartate transcarbamoylase as a trimer tag; or matrillin-based trimerization motifs. If present, the trimerization domain typically is located C-terminal to the extracellular domain (see FIG. 1B). In certain preferred embodiments where the synthetic HIV envelope protein comprises a trimerization domain, the synthetic HIV envelope protein comprises the amino acid sequence of SEQ ID NO: 19, with or without the signal sequence (i.e., amino acid residues 1-29 of SEQ ID NO: 19). These embodiments with trimerization domains are mainly useful for soluble ectodomain variants of the synthetic HIV envelope protein. In certain embodiments of such soluble variants of the invention, it is possible to mutate the furin cleavage site (e.g. mutation of Lys to Glu at position 480 in SEQ ID NO: 8) to inactivate this cleavage site, so that the protein will be a single chain; this combines well with a trimerization domain, especially with the GCN4 trimerization domain of SEQ ID NO: 19.

Alternative versions of such soluble ectodomain variants of the synthetic HIV envelope protein without use of trimerization domains are also embodiments of the invention, and can be prepared from SEQ ID NO: 8 by combining mutations that optimize the furin cleavage site (replacing the Gly-Lys dipeptide at positions 479-480 by four Arg residues) as well as so-called SOSIP mutations (I>P mutation at position 529, and introduction of a disulfide bridge between positions 471 and 575 by replacement of the respective Ala and Thr on those positions in SEQ ID NO: 8 each with a Cys residue). This yields a protein having the amino acid sequence of SEQ ID NO: 8 with the following combination of mutations: EK479-480RRRR, I529P, A471C and T575C.

One possible modification to further increase the trimer content of a synthetic HIV envelope protein of the invention (comprising SEQ ID NO: 8), is modification of Ile to Pro at position 529. This can be effective for both soluble and membrane-bound variants.

Vectors

Another general aspect of the invention relates to vectors comprising nucleic acid encoding a synthetic HIV envelope protein. According to embodiments of the invention, the vectors can comprise any of the synthetic HIV envelope proteins described herein. In a preferred embodiment of the invention, the vector comprises nucleic acid encoding a synthetic HIV envelope protein comprising the amino acid sequence of SEQ ID NO: 8, SEQ ID NO:17, SEQ ID NO: 18, or SEQ ID NO: 19, and more preferably SEQ ID NO: 18.

According to embodiments of the invention, the nucleic acid encoding the synthetic HIV envelope protein is operably linked to a promoter, meaning that the nucleic acid is under the control of a promoter. The promoter can be a homologous promoter (i.e., derived from the same genetic source as the vector) or a heterologous promoter (i.e., derived from a different vector or genetic source). Examples of suitable promoters include the cytomegalovirus (CMV) promoter and the Rous Sarcoma virus (RSV) promoter. Preferably, the promoter is located upstream of the nucleic acid within an expression cassette. An exemplary CMV promoter sequence that can be operably linked to nucleic acid encoding the synthetic HIV envelope protein is shown in SEQ ID NO: 24.

According to embodiments of the invention, a vector can be an expression vector. Expression vectors include, but are not limited to, vectors for recombinant protein expression and vector for delivery of nucleic acid into a subject for expression in a tissue of the subject, such as a viral vector. Examples of viral vectors suitable for use with the invention include, but are not limited to adenoviral vectors, adeno-associated virus vectors, pox virus vectors, MVA vectors, enteric virus vectors, Venezuelan Equine Encephalitis virus vectors, Semliki Forest Virus vectors, Tobacco Mosaic Virus vectors, lentiviral vectors, etc. The vector can also be a non-viral vector. Examples of non-viral vectors include, but are not limited to plasmids, bacterial artificial chromosomes, yeast artificial chromosomes, bacteriophages, etc.

In certain embodiments of the invention, the vector is an adenovirus vector. An adenovirus according to the invention belongs to the family of the Adenoviridae, and preferably is one that belongs to the genus Mastadenovirus. It can be a human adenovirus, but also an adenovirus that infects other species, including but not limited to a bovine adenovirus (e.g. bovine adenovirus 3, BAdV3), a canine adenovirus (e.g. CAdV2), a porcine adenovirus (e.g. PAdV3 or 5), or a simian adenovirus (which includes a monkey adenovirus and an ape adenovirus, such as a chimpanzee adenovirus or a gorilla adenovirus). Preferably, the adenovirus is a human adenovirus (HAdV, or AdHu), or a simian adenovirus such as chimpanzee or gorilla adenovirus (ChAd, AdCh, or SAdV). In the invention, a human adenovirus is meant if referred to as Ad without indication of species, e.g. the brief notation "Ad26" means the same as HadV26, which is human adenovirus serotype 26. Also as used herein, the notation "rAd" means recombinant adenovirus, e.g., "rAd26" refers to recombinant human adenovirus 26.

Most advanced studies have been performed using human adenoviruses, and human adenoviruses are preferred according to certain aspects of the invention. In certain preferred embodiments, a recombinant adenovirus according to the invention is based upon a human adenovirus. In preferred embodiments, the recombinant adenovirus is based upon a human adenovirus serotype 5, 11, 26, 34, 35, 48, 49, 50, 52, etc. According to a particularly preferred embodiment of the invention, an adenovirus is a human adenovirus of serotype 26. An advantage of this serotypes is a low seroprevalence and/or low pre-existing neutralizing antibody titers in the human population, and experience with use in human subjects in clinical trials.

Simian adenoviruses generally also have a low seroprevalence and/or low pre-existing neutralizing antibody titers in the human population, and a significant amount of work has been reported using chimpanzee adenovirus vectors (e.g. U.S. Pat. No. 6,083,716; WO 2005/071093; WO 2010/086189; WO 2010085984; Farina et al, 2001, *J Virol* 75: 11603-13 [13]; Cohen et al, 2002, *J Gen Virol* 83: 151-55 [69]; Kobinger et al, 2006, *Virology* 346: 394-401 [70]; Tatsis et al., 2007, *Molecular Therapy* 15: 608-17 [71]; see also review by Bangari and Mittal, 2006, *Vaccine* 24: 849-62 [72]; and review by Lasaro and Ertl, 2009, *Mol Ther* 17: 1333-39 [73]). Hence, in other embodiments, the recombinant adenovirus according to the invention is based upon a simian adenovirus, e.g. a chimpanzee adenovirus. In certain embodiments, the recombinant adenovirus is based upon simian adenovirus type 1, 7, 8, 21, 22, 23, 24, 25, 26, 27.1, 28.1, 29, 30, 31.1, 32, 33, 34, 35.1, 36, 37.2, 39, 40.1, 41.1, 42.1, 43, 44, 45, 46, 48, 49, 50 or SA7P.

Preferably, the adenovirus vector is a replication deficient recombinant viral vector, such as rAd26, rAd35, rAd48, rAd5HVR48, etc.

In a preferred embodiment of the invention, the adenoviral vectors comprise capsid proteins from rare serotypes including Ad26. In the typical embodiment, the vector is an rAd26 virus. An "adenovirus capsid protein" refers to a protein on the capsid of an adenovirus (e.g., Ad26, Ad35, rAd48, rAd5HVR48 vectors) that is involved in determining the serotype and/or tropism of a particular adenovirus.

Adenoviral capsid proteins typically include the fiber, penton and/or hexon proteins. As used herein a "capsid protein" for a particular adenovirus, such as an "Ad26 capsid protein" can be, for example, a chimeric capsid protein that includes at least a part of an Ad26 capsid protein. In certain embodiments, the capsid protein is an entire capsid protein of Ad26. In certain embodiments, the hexon, penton and fiber are of Ad26.

One of ordinary skill in the art will recognize that elements derived from multiple serotypes can be combined in a single recombinant adenovirus vector. Thus, a chimeric adenovirus that combines desirable properties from different serotypes can be produced. Thus, in some embodiments, a chimeric adenovirus of the invention could combine the absence of pre-existing immunity of a first serotype with characteristics such as temperature stability, assembly, anchoring, production yield, redirected or improved infection, stability of the DNA in the target cell, and the like.

In certain embodiments the recombinant adenovirus vector useful in the invention is derived mainly or entirely from Ad26 (i.e., the vector is rAd26). In some embodiments, the adenovirus is replication deficient, e.g., because it contains a deletion in the E1 region of the genome. For adenoviruses being derived from non-group C adenovirus, such as Ad26 or Ad35, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga, et al., 2006, *J Gen Virol* 87: 2135-43; WO 03/104467). However, such adenoviruses will not be capable of replicating in non-complementing cells that do not express the E1 genes of Ad5.

The preparation of recombinant adenoviral vectors is well known in the art. Preparation of rAd26 vectors is described, for example, in WO 2007/104792 and in Abbink et al., (2007) *Virol* 81(9): 4654-63. Exemplary genome sequences of Ad26 are found in GenBank Accession EF 153474 and in SEQ ID NO:1 of WO 2007/104792. Examples of vectors useful for the invention for instance include those described in WO2012/082918, the disclosure of which is incorporated herein by reference in its entirety.

Typically, a vector useful in the invention is produced using a nucleic acid comprising the entire recombinant adenoviral genome (e.g., a plasmid, cosmid, or baculovirus vector). Thus, the invention also provides isolated nucleic acid molecules that encode the adenoviral vectors of the invention. The nucleic acid molecules of the invention can be in the form of RNA or in the form of DNA obtained by cloning or produced synthetically. The DNA can be double-stranded or single-stranded.

The adenovirus vectors useful in the invention are typically replication deficient. In these embodiments, the virus is rendered replication deficient by deletion or inactivation of regions critical to replication of the virus, such as the E1 region. The regions can be substantially deleted or inactivated by, for example, inserting a gene of interest, such as a gene encoding a synthetic HIV envelope protein (usually linked to a promoter), or a gene encoding an HIV antigenic polypeptide (usually linked to a promoter) within the region. In some embodiments, the vectors of the invention can contain deletions in other regions, such as the E2, E3 or E4 regions, or insertions of heterologous genes linked to a promoter within one or more of these regions. For E2- and/or E4-mutated adenoviruses, generally E2- and/or E4-complementing cell lines are used to generate recombinant adenoviruses. Mutations in the E3 region of the adenovirus need not be complemented by the cell line, since E3 is not required for replication.

A packaging cell line is typically used to produce sufficient amounts of adenovirus vectors for use in the invention. A packaging cell is a cell that comprises those genes that have been deleted or inactivated in a replication deficient vector, thus allowing the virus to replicate in the cell. Suitable packaging cell lines for adenoviruses with a deletion in the E1 region include, for example, PER.C6, 911, 293, and E1 A549.

According to embodiments of the invention, and as noted above, any of the synthetic HIV envelope proteins described herein can be expressed in the vectors of the invention. In view of the degeneracy of the genetic code, the skilled person is well aware that several nucleic acid sequences can be designed that encode the same protein, according to methods entirely routine in the art. The nucleic acid encoding the synthetic HIV envelope protein can optionally be codon-optimized to ensure proper expression in the treated host (e.g., human). Codon-optimization is a technology widely applied in the art. Some non-limiting examples of sequences encoding a synthetic HIV envelope protein of the invention are provided in SEQ ID NOs: 25, 26 and 27. Typically, the nucleic acid encoding the synthetic HIV envelope protein is cloned into the E1 and/or the E3 region of the adenoviral genome.

In a preferred embodiment of the invention, the vector is an adenovirus vector, and more preferably a rAd26 vector, most preferably a rAd26 vector with at least a deletion in the E1 region of the adenoviral genome, e.g. such as that described in Abbink, *J Virol,* 2007. 81(9): p. 4654-63, which is incorporated herein by reference.

The invention also provides cells, preferably isolated cells, comprising any of the vectors described herein. The cells can be used for recombinant protein production, or for the production of viral particles.

Embodiments of the invention thus also relate to a method of a making a synthetic HIV antigenic polypeptide. The method comprises transfecting a host cell with an expression vector comprising nucleic acid encoding the synthetic HIV antigenic polypeptide operably linked to a promoter, growing the transfected cell under conditions suitable for expression of the synthetic HIV antigenic polypeptide, and isolating the synthetic HIV antigenic polypeptide from the cell. The synthetic HIV antigenic polypeptide can be isolated or collected from the cell by any method known in the art including affinity chromatography, etc. Techniques used for recombinant protein expression will be well known to one of ordinary skill in the art in view of the present disclosure.

The invention also includes a method for manufacturing a vector encoding a synthetic HIV antigenic polypeptide of the invention, the method comprising culturing a cell that comprises the vector, to propagate and multiply the vector during said culturing, and isolating the vector that encodes the synthetic HIV antigenic polypeptide of the invention from the cell culture, e.g. from the cells, from the culture medium, or both. The vector may be further purified according to methods known in the art.

In certain embodiments, the invention provides a vector according to an embodiment of the invention comprising a nucleic acid encoding a synthetic HIV antigenic polypeptide, and in certain exemplary embodiments the nucleic acid has a nucleotide sequence selected from the group consisting of SEQ ID NO: 25, 26 and 27.

Compositions

In another general aspect, the invention relates to a composition comprising a vector comprising a nucleic acid encoding a synthetic HIV envelope protein and a carrier. According to embodiments of the invention, any of the vectors described herein can be included in the composition. Preferably, the vector is a viral vector, more preferably an adenovirus vector, and even more preferably an adenovirus 26 vector. In a preferred embodiment, a composition comprises an adenovirus vector, preferably an adenovirus 26 vector encoding a synthetic HIV envelope protein comprising the amino acid sequence of SEQ ID NO: 8, SEQ ID NO: 18, or SEQ ID NO: 19, and more preferably the amino acid sequence of SEQ ID NO: 18.

In one aspect, the invention provides a combination vaccine comprising one or more vectors together comprising nucleic acid sequences encoding (i) a synthetic HIV envelope protein comprising the amino acid sequence of SEQ ID NO: 8 (e.g. SEQ ID NO: 18 or 19) and (ii) a second HIV envelope protein comprising the amino acid sequence of SEQ ID NO: 5. The vectors may each be in a separate composition, or be combined in a single composition. Both nucleic acids in the vector(s) are intended to be administered to one subject, which will result in an immune response to HIV that is broader than the immune response that would be obtained upon administration of either vector alone. Both nucleic acid sequences could also be present on one single vector.

According to embodiments of the invention, a composition comprises an immunogenically effective amount of a vector, such as a viral vector. As used herein, "an immunogenically effective amount" or "immunologically effective amount" means an amount of a composition sufficient to induce a desired immune effect or immune response in a subject in need thereof. In one embodiment, an immunogenically effective amount means an amount sufficient to induce an immune response in a subject in need thereof. In another embodiment, an immunogenically effective amount means an amount sufficient to produce immunity in a subject in need thereof, e.g., provide a protective effect against a disease such as a viral infection. An immunogenically effective amount can vary depending upon a variety of factors, such as the physical condition of the subject, age, weight, health, etc.; the particular application, whether inducing immune response or providing protective immunity; the specific recombinant vector administered; the immunogen or antigenic polypeptide encoded by the recombinant vector administered; the specific antigenic polypeptide administered; and the particular disease, e.g., viral infection, for which immunity is desired. An immunogenically effective amount can readily be determined by one of ordinary skill in the art in view of the present disclosure.

As general guidance, an immunogenically effective amount when used with reference to a recombinant viral vector such as an adenoviral vector can range from about $10^8$ viral particles to about $10^{12}$ viral particles, for example $10^8$, $10^9$, $10^{10}$, $10^{11}$, or $10^{12}$ viral particles. An immunogenically effective amount can be administered in a single composition, or in multiple compositions, such as 1, 2, 3, 4, 5, 6, 7, 8, 9, or 10 compositions (e.g., tablets, capsules or injectables), wherein the administration of the multiple capsules or injections collectively provides a subject with the immunogenically effective amount. In general, when used with reference to a polypeptide, such as an isolated antigenic polypeptide, an immunogenically effective amount can range from, e.g. about 0.3 to about 3000 microgram (μg), e.g. 1-1000 μg, e.g. 10-500 μg, e.g. about 10, 50, 100, 150, 200, 250, 300, 350, 400, 450 or 500 μg. As a non-limiting example, it is possible to combine administration of the vector encoding the synthetic HIV Env antigen of the invention (having SEQ ID NO: 8) with administration of an Env polypeptide, e.g. 250 μg of HIV Clade C Env trimer protein having amino acids 30-708 of SEQ ID NO: 7. It is also possible to administer an immunogenically effective amount to a subject, and subsequently administer another dose of an immunogenically effective amount to the same subject, in a so-called prime-boost regimen. This general concept of a prime-boost regimen is well known to the skill person in the vaccine field. Further booster administrations can optionally be added to the regimen, as needed.

Compositions of the invention further comprise a carrier. A carrier can include one or more pharmaceutically acceptable excipients such as binders, disintegrants, swelling agents, suspending agents, emulsifying agents, wetting agents, lubricants, flavorants, sweeteners, preservatives, dyes, solubilizers and coatings. The precise nature of the carrier or other material can depend on the route of administration, e.g., intramuscular, subcutaneous, oral, intravenous, cutaneous, intramucosal (e.g., gut), intranasal or intraperitoneal routes. For liquid injectable preparations, for example, suspensions and solutions, suitable carriers and additives include water, glycols, oils, alcohols, preservatives, coloring agents and the like. For solid oral preparations, for example, powders, capsules, caplets, gelcaps and tablets, suitable carriers and additives include starches, sugars, diluents, granulating agents, lubricants, binders, disintegrating agents and the like. For nasal sprays/inhalant mixtures, the aqueous solution/suspension can comprise water, glycols, oils, emollients, stabilizers, wetting agents, preservatives, aromatics, flavors, and the like as suitable carriers and additives.

Compositions of the invention can be formulated in any matter suitable for administration to a subject to facilitate administration and improve efficacy, including, but not limited to, oral (enteral) administration and parenteral injections. The parenteral injections include intravenous injection or infusion, intra-arterial injection, subcutaneous injection, intramuscular injection, and intra-articular injection. Compositions of the invention can also be formulated for other routes of administration including transmucosal, ocular, rectal, long acting implantation, sublingual administration, under the tongue, from oral mucosa bypassing the portal circulation, inhalation, or intranasal.

According to certain embodiments of the invention, a composition comprises an immunogenically effective amount of purified or partially purified adenovirus vector, such as an adenovirus 26 vector, comprising a nucleic acid encoding a synthetic HIV envelope protein of the invention. Said compositions can be formulated as a vaccine (also referred to as an "immunogenic composition") according to methods well known in the art.

Compositions of the invention can further optionally comprise an adjuvant to enhance immune responses. The terms "adjuvant" and "immune stimulant" are used interchangeably herein, and are defined as one or more substances that cause stimulation of the immune system. In this context, an adjuvant is used to enhance an immune response to the vectors encoding synthetic HIV envelope proteins of the invention and/or HIV antigenic polypeptides used in combination with vectors encoding synthetic HIV envelope proteins of the invention.

Adjuvants suitable for use with the invention should be ones that are potentially safe, well tolerated and effective in people, such as for instance QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, aluminum salts (e.g. AdjuPhos), Adjuplex, and MF59. The optimal ratios of each component in the formulation can be determined by techniques well known to those skilled in the art in view of the present disclosure.

In a preferred embodiment, the adjuvant is an aluminum salt, such as AdjuPhos.

The preparation and use of immunogenic compositions are well known to those of ordinary skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can also be included.

For instance recombinant adenovirus vector may be stored in the buffer that is also used for the Adenovirus World Standard (Hoganson et al., 2002, *Bioprocessing J* 1: 43-8): 20 mM Tris pH 8, 25 mM NaCl, 2.5% glycerol. Another useful adenovirus formulation buffer suitable for administration to humans is 20 mM Tris, 2 mM $MgCl_2$, 25 mM NaCl, sucrose 10% w/v, polysorbate-80 0.02% w/v. Another formulation buffer that is suitable for recombinant adenovirus comprises 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Obviously, many other buffers can be used, and several examples of suitable formulations for the storage and for pharmaceutical administration of purified vectors are known.

According to embodiments of the invention, a composition of the invention can be used together with one or more additional vectors encoding one or more additional HIV antigenic polypeptides, and/or one or more isolated HIV antigenic polypeptides. The additional vectors and/or HIV antigenic polypeptides can be present in the same composition comprising a synthetic HIV Env protein of the invention. They can also be present in one or more different compositions that can be used together with a composition comprising a synthetic HIV Env protein of the invention in a vaccine combination. Preferably, the one or more additional vectors are viral vectors, such as adenovirus vectors, and are most preferably adenovirus 26 vectors. The one or more additional vectors can encode any HIV antigenic polypeptide known to those skilled in the art in view of the present disclosure.

In one embodiment, a composition or a vaccine combination further comprises a second adenovirus vector, preferably an adenovirus 26 vector, encoding a HIV antigenic polypeptide comprising the amino acid sequence of SEQ ID NO: 5. An advantage of such embodiments is increased breadth of the immune response (covering strains from Clades B and C).

In another embodiment, a composition or a vaccine combination of the invention further comprises an adenovirus vector, preferably an adenovirus 26 vector, encoding an HIV antigenic polypeptide comprising the amino acid sequence of SEQ ID NO: 28 (mos1GagPol).

In another embodiment, a composition or a vaccine combination of the invention further comprises an adenovirus vector, preferably an adenovirus 26 vector, encoding an HIV antigenic polypeptide comprising the amino acid sequence of SEQ ID NO: 29 (mos2GagPol).

In a particular embodiment, a composition or a vaccine combination of the invention further comprises a second adenovirus vector, preferably an adenovirus 26 vector, encoding a HIV antigenic polypeptide comprising the amino acid sequence of SEQ ID NO: 5, and one or more additional adenovirus vectors, preferably adenovirus 26 vectors, encoding one or more HIV antigenic polypeptides comprising the amino acid sequence selected from the group consisting of SEQ ID NO: 28 or SEQ ID NO: 29. For example, a composition or a vaccine combination according to an embodiment of the invention can comprise four adenovirus vectors, preferably adenovirus 26 vectors, with a first vector encoding a synthetic HIV envelope protein comprising the amino acid sequence of SEQ ID NO: 8 (e.g. SEQ ID NO: 18); a second vector encoding a HIV antigenic polypeptide comprising the amino acid sequence of SEQ ID NO: 5; a third vector encoding a synthetic HIV envelope protein comprising the amino acid sequence of SEQ ID NO: 28; and a fourth vector encoding a synthetic HIV envelope protein comprising the amino acid sequence of SEQ ID NO: 29.

In some embodiments, the composition or a vaccine combination further comprises one or more isolated HIV antigenic polypeptides. Any HIV antigenic polypeptide known to those skilled in the art in view of the present disclosure can be further included in a composition or a vaccine combination of the invention, including, but not limited to an HIV envelope protein (e.g., gp160, gp140, gp120, or gp41), preferably a stabilized trimeric gp140 protein, such as a stabilized clade C or clade A gp140 protein. In a preferred embodiment, the isolated HIV antigenic polypeptide is a stabilized HIV clade C trimeric gp140 protein, such as that comprising residues 30-708 of the amino acid sequence of SEQ ID NO: 7 (residues 1-29 of SEQ ID NO: 7 are in the signal sequence). An alternative or additional HIV Env polypeptide that could be used in addition to the clade C gp140 protein or alone, is a mosaic Env trimer protein, for instance having an amino acid sequence as disclosed in amino acids 30-724 of SEQ ID NO: 36 (corresponding to SEQ ID NO: 2 of WO 2014/107744, residues 1-29 of SEQ ID NO: 36 are in the signal sequence).

According to a particular embodiment of the invention, an HIV antigenic protein can be a synthetic HIV envelope protein of the invention. Thus, a synthetic envelope protein of the invention can be used in isolated and/or purified form to induce an immune response or provide a protective immunity, etc. against HIV in a subject in need thereof. Any of the synthetic envelope proteins described herein comprising the amino acid sequence of SEQ ID NO: 8 can be used as an HIV antigenic protein in isolated and/or purified form. In a preferred embodiment, when used in isolated form as an HIV antigenic protein, the synthetic envelope protein comprises residues 30-711 of the amino acid sequence of SEQ ID NO: 18 or residues 30-686 of the amino acid sequence of SEQ ID NO: 19, and more preferably residues 30-704 of the amino acid sequence of SEQ ID NO: 18. The isolated HIV antigenic polypeptide can also comprise SEQ ID NO: 8 with the following mutations: EK479-480RRRR, I529P, A471C and T575C.

Embodiments of the invention also relate to compositions or vaccine combinations comprising an isolated synthetic HIV envelope protein comprising the amino acid sequence of SEQ ID NO: 8. Any of the synthetic HIV envelope proteins described herein can be used. In particular embodiments of the invention, the isolated synthetic HIV envelope protein comprises residues 30-704 or 30-711 of the amino acid sequence of SEQ ID NO:18, residues 30-686 of the amino acid sequence of SEQ ID NO: 19, or the amino acid sequence of SEQ ID NO: 8 with the following mutations: EK479-480RRRR, I529P, A471C and T575C. Such compositions or vaccine combinations can further comprise one or more expression vectors, e.g., adenoviral vectors such as adenovirus 26 vectors, encoding one or more additional HIV antigenic polypeptides, such as the synthetic HIV envelope proteins of the invention, or other HIV antigenic proteins such as those set forth in SEQ ID NOs: 4, 5, 7, 28 or 29, or fragments thereof.

The invention also relates to a method of producing a composition or a vaccine combination of the invention. According to embodiments of the invention, a method of producing a composition or a combination comprises combining a vector comprising nucleic acid encoding the synthetic HIV envelope protein of the invention with a carrier, and optionally one or more additional vectors encoding one or more additional HIV antigenic polypeptides and/or one or more isolated HIV antigenic polypeptides. One of ordinary skill in the art will be familiar with conventional techniques used to prepare such compositions.

Vaccine and Vaccine Combinations

According to embodiments of the invention, a composition can be a vaccine. As used herein, the term "vaccine" refers to a composition comprising an expression vector, preferably a viral vector, encoding a synthetic HIV envelope protein of the invention that can provide protective immunity or a protective immune response to a subject, or to vaccinate a subject. According to embodiments of the invention, upon administration of the composition to a subject, the expression vector expresses the encoded synthetic HIV envelope protein, and the expressed synthetic HIV envelope protein is presented to the immune system of the subject, thereby inducing the required response to produce immunity, or induce an immune response.

Thus, in another general aspect, the invention provides a vaccine for inducing an immune response against a human immunodeficiency virus (HIV) in a subject. According to embodiments of the invention, the vaccine comprises a composition comprising an immunogenically effective amount of an expression vector encoding a synthetic HIV envelope protein comprising the amino acid sequence of SEQ ID NO: 8, and preferably the amino acid sequence of SEQ ID NO: 18. Preferably, the expression vector is a viral vector, more preferably an adenovirus vector, and most preferably an adenovirus 26 vector.

According to embodiments of the invention, "inducing an immune response" when used with reference to the methods and compositions described herein encompasses providing protective immunity and/or vaccinating a subject against an infection, such as a HIV infection, for prophylactic purposes, as well as causing a desired immune response or effect in a subject in need thereof against an infection, such as a HIV infection, for therapeutic purposes. Preferably, the methods of the invention are for prophylactic purposes, such as for providing protective immunity. The immune response can be a cellular immune response and/or a humoral immune response.

As used herein, the term "protective immunity" or "protective immune response" means that the vaccinated subject is able to control an infection with the pathogenic agent against which the vaccination was done. Usually, the subject having developed a "protective immune response" develops only mild to moderate clinical symptoms or no symptoms at all. Usually, a subject having a "protective immune response" or "protective immunity" against a certain agent will not die as a result of the infection with said agent.

According to embodiments of the invention, vaccine compositions can further comprise one or more additional vectors, e.g., viral vectors, such as adenovirus vectors, preferably adenovirus 26 vectors, encoding one or more additional HIV antigenic polypeptides and/or one or more isolated HIV antigenic polypeptides. The synthetic HIV envelope protein, additional vectors and/or one or more isolated HIV antigenic polypeptides can be formulated in the same composition or one or more different compositions in the vaccine.

The invention also relates to vaccine combinations for priming and boosting an immune response to one or more HIV clades in a subject in need thereof using one or more vectors in combination with an isolated antigenic polypeptide. Thus, in another general aspect, the invention provides a vaccine combination for inducing an immune response against a HIV in a subject. According to embodiments of the invention, the vaccine combination comprises:

(i) a first composition comprising an immunogenically effective amount of an expression vector encoding a synthetic HIV envelope protein comprising the amino acid sequence of SEQ ID NO: 8 or SEQ ID NO: 8 having one or more mutations selected from the group consisting of (a) I529P, (b) K480E, and (c) a combination of EK479-480RRRR, I529P, A471C and T575C, and a carrier; and (ii) a second composition comprising an immunogenically effective amount of an isolated HIV antigenic polypeptide and a carrier, wherein one of the first and second compositions is for priming immunization and the other composition is for boosting immunization.

According to embodiments of the invention, the vaccine combination optionally further comprises an immunogenically effective amount of one or more additional expression vectors encoding one or more additional HIV antigenic polypeptides. The one or more additional expression vectors can be included in the first composition or the second composition, or the one or more additional expression vectors can be included in one or more additional compositions to be administered together with the first and/or second composition.

As used herein, the terms "co-delivery", "co-administration" or "administered together with" refers to simultaneous administration of two or more components, such as a viral expression vector and an isolated antigenic polypeptide, or multiple viral expression vectors. "Simultaneous administration" can be administration of the two or more components at least within the same day. When two components are "administered together with," they can be administered in separate compositions sequentially within a short time period, such as 24, 20, 16, 12, 8 or 4 hours, or within 1 hour or less, or they can be administered in a single composition at the same time.

In particular embodiments of a vaccine combination of the invention, the first composition comprises an adenovirus vector, preferably an adenovirus 26 vector, encoding a synthetic HIV envelope protein comprising the amino acid sequence of SEQ ID NO: 18; and the isolated HIV antigenic polypeptide comprises residues 30-708 of the amino acid sequence of SEQ ID NO: 7 or residues 30-724 of SEQ ID NO: 36. In one particular embodiment, the first composition further comprises an adenovirus vector, preferably an adenovirus 26 vector, encoding a HIV antigenic polypeptide comprising the amino acid sequence of SEQ ID NO: 5. In another particular embodiment, the first composition further comprises one or more additional adenovirus vectors, preferably adenovirus 26 vectors, encoding one or more additional HIV antigenic polypeptides comprising the amino acid sequences selected from the group consisting of SEQ ID NOs: 28 and 29.

Another general aspect of the invention relates to a kit comprising a vaccine combination according to an embodiment of the invention.

Other embodiments of the synthetic HIV envelope protein, expression vectors, additional expression vectors, HIV antigenic polypeptides encoded by the expression vectors, and isolated HIV antigenic polypeptide etc. that can be used in the vaccine combinations of the invention are discussed in detail above and in the illustrative examples below.

Method for Inducing Protective Immunity Against HIV Infection

The invention also relates to a method of inducing an immune response against one or more HIV clades in a subject in need thereof. The methods described herein include methods of priming and boosting an immune response using one or more expression vectors in combination with one or more isolated antigenic polypeptides.

In one general aspect, a method of inducing an immune response against a human immunodeficiency virus (HIV) in a subject comprises administering to the subject a composition comprising an immunogenically effective amount of an expression vector comprising a nucleic acid encoding a synthetic HIV envelope protein comprising the amino acid sequence of SEQ ID NO: 8. Any of the compositions described herein can be used in a method of inducing an immune response against HIV in a subject. Preferably, the composition comprises an adenovirus vector, preferably an adenovirus 26 vector, comprising a nucleic acid encoding a synthetic HIV envelope protein comprising the amino acid sequence of SEQ ID NO: 18. The composition can further comprise one or more additional vectors encoding one or more additional HIV antigenic polypeptides and/or one or more additional isolated HIV antigenic polypeptides.

In another general aspect, a method of inducing an immune response against a human immunodeficiency virus (HIV) in a subject comprises:
  (i) administering to the subject a first composition comprising an immunogenically effective amount of an expression vector encoding a mosaic HIV envelope protein having the amino acid sequence of SEQ ID NO: 8 or SEQ ID NO: 8 having one or more mutations selected from the group consisting of (a) 1529P, (b) K480E, and (c) a combination of EK479-480RRRR, I529P, A471C and T575C, and a carrier;
  (ii) administering to the subject a second composition comprising an immunogenically effective amount of an isolated HIV antigenic polypeptide and a carrier; and
  (iii) optionally, administering to the subject an immunogenically effective amount of one or more additional expression vectors encoding one or more additional HIV antigenic polypeptides,
wherein steps (i) and (ii) are conducted in either order, with one of the steps for priming immunization and the other step for boosting immunization. According to embodiments of the invention, the optional, effective amount of the one more additional expression vectors is administered together with the first composition or the second composition. In a preferred embodiment, the optional effective amount of the one or more additional expression vectors is administered together with the first composition.

In a particular embodiment of a method of inducing an immune response, the first composition comprises an adenovirus vector, preferably an adenovirus 26 vector, encoding a synthetic HIV envelope protein comprising the amino acid sequence of SEQ ID NO: 8 and a second adenovirus vector, preferably an adenovirus 26 vector, encoding a HIV antigenic polypeptide comprising the amino acid sequence of SEQ ID NO: 5; the second composition comprises an isolated HIV antigenic polypeptide having residues 30-708 of the amino acid sequence of SEQ ID NO:7 or residues 30-724 of SEQ ID NO: 36; and the one or more additional expression vectors are adenovirus vectors, preferably adenovirus 26 vectors, encoding one or more additional HIV antigenic polypeptides comprising the amino acid sequences selected from the group consisting of SEQ ID NOs: 28 and 29; wherein the first composition is administered to the subject, together with the one or more additional expression vectors, one or more times for priming immunization, and the second composition is administered to the subject one or more times for boosting immunization.

Administration of the immunogenic compositions comprising the expression vectors and/or antigenic polypeptides is typically intramuscular, intradermal or subcutaneous. However, other modes of administration such as intravenous, rectal, cutaneous, oral, nasal, etc can be envisaged as well. Intramuscular administration of the immunogenic compositions can be achieved by using a needle to inject a suspension of the expression vectors, e.g. adenovirus vectors, and/or antigenic polypeptides. An alternative is the use of a needleless injection device to administer the composition (using, e.g., Biojector™) or a freeze-dried powder containing the vaccine.

For intramuscular, intravenous, cutaneous or subcutaneous injection, or injection at the site of affliction, the vector will be in the form of a parenterally acceptable aqueous solution which is pyrogen-free and has suitable pH, isotonicity and stability. Likewise, the isolated antigenic polypeptide will be in the form of a parenterally acceptable solution having a suitable pH, isotonicity, and stability. Those of ordinary skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation can also be employed.

Typically, administration of the vaccine compositions according to embodiments of the invention will have a prophylactic aim to generate an immune response against an HIV antigen before infection or development of symptoms. In other embodiments, the expression vectors, e.g., adenovirus vectors, and/or HIV antigenic polypeptides can be administered for post-exposure prophylactics.

The immunogenic compositions containing the expression vectors, e.g., adenovirus vectors, and/or antigenic polypeptides are administered to a subject, giving rise to an anti-HIV immune response in the subject. An amount of a composition sufficient to induce a detectable immune response is defined to be an "immunogenically effective dose" or "immunogenically effective amount." In a typical embodiment of the invention, the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

Following production of adenovirus vectors and optional formulation of such particles into compositions, the vectors can be administered to an individual, particularly a human or other primate. Delivery to a non-human mammal need not be for a therapeutic purpose, but can be for use in an experimental context, for instance in investigation of mechanisms of immune responses to the synthetic HIV envelope protein expressed by the adenovirus vectors of the invention.

In one embodiment of the disclosed methods, one or more adenovirus vectors encoding one or more HIV antigenic polypeptides are used to prime the immune response. One or more isolated HIV antigenic polypeptides can be used together with the one or more adenovirus vectors for the priming immunization. The priming immunization may be administered only once but can optionally also be administered multiple times, for example, initial priming administration at time 0, followed by another priming administration about 4-14 weeks, e.g. 4, 5, 6, 7, 8, 9, 10, 11, 12, 13 or 14 weeks, or any time in between, after the initial priming administration. One or more isolated HIV antigenic polypeptides optionally together with one or more additional adenovirus or other vectors encoding one or more additional HIV antigenic polypeptides can be used to boost the immune response. A boosting immunization can also be administered once or multiple times, for example, first at about 18-36, e.g. 18, 19, 20, 21, 22, 23, 24, 25, 26, 27, 28, 29, 30, 31, 32, 33, 34, 35 or 36 weeks, or any time in between, after the initial priming administration, followed by another boosting administration at about 36-52, e.g. 36, 37, 38, 39, 40, 41, 42, 43, 44, 45, 46, 47, 48, 49, 50, 51, 52, 53, 54, 55, 56, 57, 58, 59 or 60 weeks, or any time in between, after the initial priming administration. The immune response induced by the immunization is monitored.

Embodiments of the disclosed methods also contemplate shorter prime-boost regimens, meaning that the final boosting immunization is administered about 22-26 weeks after the initial priming administration. The priming immunization can be administered at week 0. The boosting immunization can be administered multiple times, for example, first at about 7-9 weeks or 11-13 weeks, or at about 4, 5, 6, 7, 8, 9, 10, 11, 12, 13, or 14 weeks, or any time in between, after the initial priming administration, followed by another boosting administration at about 22-26 weeks, or at about 16, 17, 18, 19, 20, 21, 22, 23, 24, 25, 26, 27, or 28 weeks, or any time in between, after the initial priming administration. In certain embodiments, one or more isolated HIV antigenic polypeptides is administered together with the one or more adenovirus vectors for the priming and/or boosting immunization.

It is readily appreciated by those skilled in the art that the regimen for the priming and boosting administrations can be adjusted based on the measured immune responses after the administrations. For example, the boosting compositions are generally administered weeks or months after administration of the priming composition, for example, about 2-3 weeks or 4 weeks, or 8 weeks, or 16 weeks, or 20 weeks, or 24 weeks, or 28 weeks, or 30 weeks or 32 weeks or one to two years after administration of the priming composition.

According to embodiments of the invention, an adjuvant can be administered together with the isolated HIV antigenic polypeptide as part of the priming and/or boosting immunization. Any adjuvant can be used in view of the present disclosure, and in certain embodiments the adjuvant is an aluminum salt, such as AdjuPhos.

In a preferred embodiment of the invention, the adenovirus vectors used in the methods disclosed herein include a rAd26 vector. Preferably, an rAd26 vector encoding a synthetic HIV envelope protein comprising the amino acid sequence of SEQ ID NO: 18 or SEQ ID NO: 19, most preferably SEQ ID NO: 18, is used to prime the immune response, alone or in combination with one or more additional rAd26 vectors encoding one or more additional HIV antigenic polypeptides, such as mos1Env having the amino acid sequence of SEQ ID NO: 5, and an isolated HIV antigenic polypeptide, such as that comprising residues 30-708 of the amino acid sequence of SEQ ID NO: 7 or residues 30-724 of SEQ ID NO: 36, is used to boost the immune response, or vice versa.

In one exemplary embodiment, an rAd26 vector encoding a synthetic HIV envelope protein comprising the amino acid sequence of SEQ ID NO: 18 is used to prime the immune response in combination with an rAd26 vector encoding an HIV antigenic polypeptide having the amino acid sequence of SEQ ID NO: 5. One or more additional rAd26 vectors encoding one or more additional HIV antigenic polypeptides having the amino acid sequences selected from the group consisting SEQ ID NOs: 1-4, 28 and 29 can also be administered together with the other rAd26 vectors to prime the immune response. The priming administration in certain embodiments is administered twice before any boosting immunization is administered. An isolated HIV antigenic polypeptide, such as that comprising residues 30-708 of the amino acid sequence of SEQ ID NO: 7 (preferably), or that comprising residues 30-724 of the amino acid sequence of SEQ ID NO:36, or a combination of at least two of such isolated HIV antigenic polypeptides, is then administered to boost the immune response, and is preferably administered more than once. Preferably, an adjuvant is further administered with the isolated HIV antigenic polypeptide in the boosting immunization.

In a particular embodiment, an immune response is primed by administration of four HIV antigens encoded on adenoviral vectors, preferably rAd26 vectors, the four antigens that are encoded being: (i) a synthetic HIV envelope protein comprising the amino acid sequence of SEQ ID NO: 18, (ii) polypeptide having the amino acid sequence of SEQ ID NO: 5, (iii) polypeptide having the amino acid sequence of SEQ ID NO: 28, and (iv) polypeptide having the amino acid sequence of SEQ ID NO: 29. Each of these four antigens can be encoded on a separate adenoviral vector, preferably a rAd26 vector, administered at a total dose of about 1, 2, 3, 4, 5, 6, 7, 8, 9, or $10 \times 10^{10}$ viral particles (vp), e.g. about $5 \times 10^{10}$ vp (for all vectors together). The vectors may be pre-mixed, e.g. in a 1:1:1:1 ratio. The priming administration may be repeated after the initial priming administration, e.g. at 8, 9, 10, 11, 12, 13, 14, 15 or 16 weeks after the initial priming administration. In this embodiment, an immune response is boosted by administration of the same adenoviral vector vaccine used for the priming administration together with isolated HIV Env gp140 protein, e.g. clade C gp140 protein (comprising residues 30-708 of the amino acid sequence of SEQ ID NO: 7), or mosaic gp140 protein (comprising residues 30-724 of the amino acid sequence of SEQ ID NO:36), or clade C gp140 protein and mosaic gp140 protein, at a total dose of about 50-300 g protein, e.g. 50, 100, 150, 200, 250, or 300 microgram, or any amount in between, of clade C gp140 protein, or e.g. 50, 100, 150, 200, 250, or 300 microgram, or any amount in between, of mosaic gp140 protein, or e.g. 50, 100, 150, 200, 250, or 300 microgram, or any amount in between, of a combination of clade C gp140 protein and mosaic gp140 protein (e.g. in a 1:1 ratio, either mixed together or separately administered). Preferably the gp140 protein is administered together with adjuvant, e.g. aluminium phosphate. The adenovirus plus gp140 protein administration to boost the immune response may be performed at about 18, 19, 20, 21, 22, 23, 24, 25, 26, 27, 28, 29 or 30 weeks, or at any time in between, after the initial priming administration. The boost administration may be repeated, e.g. at about 42, 43, 44, 45, 46, 47, 48, 49, 50, 51, 52, 53 or 54 weeks, or any time in between, after the initial priming administration. All administrations according to this embodiment are preferably performed via the intramuscular route.

EMBODIMENTS

Embodiment 1 is a nucleic acid encoding a synthetic HIV envelope protein comprising the amino acid sequence of SEQ ID NO: 8, or SEQ ID NO: 8 having one or more mutations selected from the group consisting of (i) I529P, (ii) K480E, and (iii) a combination of EK479-480RRRR, I529P, A471C and T575C.

Embodiment 2 is a nucleic acid according to embodiment 1, wherein the synthetic HIV envelope protein further comprises a signal sequence, for instance a signal sequence comprising the amino acid sequence selected from the group consisting of SEQ ID NOs:9 to 12, preferably SEQ ID NO: 9.

Embodiment 3 is a nucleic acid according to embodiment 1 or 2, wherein the synthetic HIV envelope protein further comprises a transmembrane domain, for instance a transmembrane domain having the amino acid sequence of SEQ ID NO: 13, preferably the synthetic HIV envelope protein further comprises SEQ ID NO:37 that is fused to the C-terminus of SEQ ID NO:8 and the N-terminus of the transmembrane domain.

Embodiment 4 is a nucleic acid according to embodiment 3, wherein the synthetic HIV envelope protein further comprises a fragment of a cytoplasmic domain, preferably a fragment of a cytoplasmic domain comprising the amino acid sequence of SEQ ID NO: 14, or amino acid residues 1-4 thereof (i.e., NRVR).

Embodiment 5 is a nucleic acid of any one of the preceding embodiments 1-4, wherein the synthetic HIV envelope protein comprises the amino acid sequence of SEQ ID NO: 18.

Embodiment 6 is a nucleic acid according to embodiment 1 or 2, wherein the synthetic HIV envelope protein either (a) further comprises a trimerization domain selected from the group consisting of GCN4, fibritin (foldon domain), for instance a trimerization domain having the amino acid sequence of SEQ ID NO: 15 or SEQ ID NO:16, preferably SEQ ID NO: 15, or (b) comprises SEQ ID NO:8 with a combination of the following mutations: EK479-480RRRR, I529P, A471C and T575C.

Embodiment 7 is a nucleic acid according to embodiment 6, wherein the synthetic HIV envelope protein comprises the amino acid sequence of SEQ ID NO: 19.

Embodiment 8 is a nucleic acid according to embodiment 5, wherein the synthetic HIV envelope protein consists of the amino acid sequence of SEQ ID NO: 18.

Embodiment 9 is a nucleic acid according to embodiment 7, wherein the synthetic HIV envelope protein consists of the amino acid sequence of SEQ ID NO: 19.

Embodiment 10 is a vector comprising the nucleic acid of any one of embodiments 1-9, wherein the nucleic acid is operably linked to a promoter sequence.

Embodiment 11 is a vector according to embodiment 10 being a viral vector, preferably an adenovirus vector, and more preferably an adenovirus 26 vector.

Embodiment 12 is an isolated cell comprising the vector of embodiment 10 or embodiment 11.

Embodiment 13 is a composition comprising an immunogenically effective amount of the vector of embodiment 10 or claim 11, and a carrier.

Embodiment 14 is a vaccine combination, comprising a first composition comprising an immunogenically effective amount of an adenovirus vector, preferably an adenovirus 26 vector, encoding a synthetic HIV envelope protein having the amino acid sequence of SEQ ID NO: 18, a second composition comprising an immunogenically effective amount of a second adenovirus vector, preferably a second adenovirus 26 vector, encoding an HIV antigenic polypeptide comprising the amino acid sequence of SEQ ID NO: 5, and optionally at least one additional composition comprising an immunogenically effective amount of at least one selected from the group consisting of a vector encoding an antigenic polypeptide having the amino acid sequence selected from the group consisting of SEQ ID NOs: 1-4, 28 and 29, and an isolated HIV antigenic polypeptide having residues 30-708 of the amino acid sequence of SEQ ID NO: 7, or residues 30-724 of the amino acid sequence of SEQ ID NO: 36, wherein the first composition, second composition and additional composition are present in the same composition or in one or more different compositions.

Embodiment 15 is a method of inducing an immune response against a human immunodeficiency virus (HIV) in a subject in need thereof, the method comprising administering to the subject the composition of embodiment 13 or the vaccine combination of embodiment 14.

Embodiment 16 is a composition of embodiment 13 or a vaccine combination of embodiment 14, comprising an adenovirus vector, preferably an adenovirus 26 vector, encoding a synthetic HIV envelope protein comprising the amino acid sequence of SEQ ID NO:18, a second adenovirus vector, preferably an adenovirus 26 vector, encoding an HIV antigenic polypeptide comprising the amino acid sequence of SEQ ID NO: 5, one or more additional adenovirus vectors encoding one or more additional antigenic polypeptides comprising the amino acid sequence selected from the group consisting of SEQ ID NOs: 1-4, 28 and 29, and an isolated HIV antigenic polypeptide comprising residues 30-708 of the amino acid sequence of SEQ ID NO: 7 or residues 30-724 of SEQ ID NO: 36, for use in inducing an immune response against a human immunodeficiency virus (HIV).

Embodiment 17 is a synthetic HIV envelope protein comprising the amino acid sequence of SEQ ID NO: 8 or SEQ ID NO: 8 having one or more mutations selected from the group consisting of (i) I529P, (ii) K480E, and (iii) a combination of EK479-480RRRR, I529P, A471C and T575C.

Embodiment 18 is a synthetic HIV envelope protein of embodiment 17, comprising the amino acid sequence of SEQ ID NO: 8 with a combination of mutations EK479-480RRRR, I529P, A471C and T575C, or residues 30-704 of the amino acid sequence SEQ ID NO: 18 or residues 30-686 of SEQ ID NO: 19.

Embodiment 19 is a composition of embodiment 13, further comprising one or more additional expression vectors encoding one or more additional HIV antigenic polypeptides, and/or one or more isolated HIV antigenic polypeptides.

Embodiment 20 is a composition of embodiment 13 comprising an adenovirus vector, preferably an adenovirus 26 vector, encoding a synthetic HIV envelope protein consisting of the amino acid sequence of SEQ ID NO: 18.

Embodiment 21 is a composition according to embodiment 20 further comprising a second adenovirus vector, preferably an adenovirus 26 vector, encoding an HIV antigenic polypeptide comprising the amino acid sequence of SEQ ID NO: 5, and optionally one or more additional adenovirus vectors, preferably adenovirus 26 vectors, encoding one or more additional HIV antigenic polypeptides comprising the amino acid sequences of SEQ ID NOs: 1-4, 28 and 29.

Embodiment 22 is a method of producing an immune response against a human immunodeficiency virus (HIV) in a subject in need thereof, the method comprising administering to the subject a composition according to any one of embodiments 19, 20, or 21.

Embodiment 23 is a method of producing a composition or a vaccine combination, comprising combining the vector of embodiment 10 or embodiment 11 with a carrier, and optionally one or more additional vectors encoding one or more additional HIV antigenic polypeptides and/or one or more isolated HIV antigenic polypeptides in one or more compositions, together with a carrier.

Embodiment 24 is a vaccine combination for inducing an immune response against a human immunodeficiency virus (HIV) in a subject, comprising:
  (i) a first composition comprising an immunogenically effective amount of an expression vector encoding a synthetic HIV envelope protein comprising the amino acid sequence of SEQ ID NO: 8 or SEQ ID NO: 8 having one or more mutations selected from the group consisting of (i) I529P, (ii) K480E, and (iii) a combination of EK479-480RRRR, I529P, A471C and T575C, and a carrier; and
  (ii) a second composition comprising an immunogenically effective amount of an isolated HIV antigenic polypeptide and a carrier,
wherein one of the first and second compositions is for priming immunization and the other composition is for boosting immunization, and
wherein the vaccine combination optionally further comprises an immunogenically effective amount of one or more additional expression vectors encoding one or more additional HIV antigenic polypeptides, and the one or more additional expression vectors are included in the first or the second composition or one or more additional compositions to be used together with the first or second composition.

Embodiment 25 is a vaccine combination according to embodiment 24, wherein the first composition comprises an adenovirus vector, preferably an adenovirus 26 vector, encoding a synthetic HIV envelope protein comprising the amino acid sequence of SEQ ID NO: 18; the isolated HIV antigenic polypeptide comprises residues 30-708 of the amino acid sequence of SEQ ID NO: 7, or residues 30-724 of SEQ ID NO: 36; and the one or more additional expression vectors are adenovirus vectors, preferably adenovirus 26 vectors, encoding one or more additional HIV antigenic polypeptides comprising the amino acid sequences selected from the group consisting of SEQ ID NOs: 1-5, 28 and 29.

Embodiment 26 is a method of inducing an immune response against a human immunodeficiency virus (HIV) in a subject in need thereof, the method comprising:
  (i) administering to the subject a first composition comprising an immunogenically effective amount of an expression vector encoding a synthetic HIV envelope protein comprising the amino acid sequence of SEQ ID NO: 8 or SEQ ID NO: 8 having one or more mutations selected from the group consisting of (i) I529P, (ii) K480E, and (iii) a combination of EK479-480RRRR, I529P, A471C and T575C, and a carrier;
  (ii) administering to the subject a second composition comprising an immunogenically effective amount of an isolated HIV antigenic polypeptide and a carrier; and
  (iii) optionally, administering to the subject an immunogenically effective amount of one or more additional expression vectors encoding one or more additional HIV antigenic polypeptides,
wherein steps (i) and (ii) are conducted in either order, with one of the steps for priming immunization and the other step for boosting immunization, and preferably, the optional, effective amount of the one more additional expression vectors is administered together with the first composition.

Embodiment 27 is a method according to embodiment 26, wherein the first composition comprises an adenovirus vector, preferably an adenovirus 26 vector, encoding a synthetic HIV envelope protein having the amino acid sequence of SEQ ID NO: 18 and a second adenovirus vector, preferably an adenovirus 26 vector, encoding a HIV antigenic polypeptide comprising the amino acid sequence of SEQ ID NO: 5; the second composition comprises an isolated HIV antigenic polypeptide having residues 30-708 of the amino acid sequence of SEQ ID NO: 7, or residues 30-724 of SEQ ID NO: 36; and the optional one or more additional expression vectors are adenovirus vectors, preferably adenovirus 26 vectors, encoding one or more additional HIV antigenic polypeptides comprising the amino acid sequences selected from the group consisting of SEQ ID NOs: 28 and 29; wherein the first composition is administered to the subject, optionally together with the one or more additional expression vectors, one or more times for priming immunization, and the second composition is administered to the subject one or more times for boosting immunization.

Embodiment 28 is a synthetic HIV envelope protein consisting of the amino acid sequence of SEQ ID NO: 18 or SEQ ID NO: 19, with or without the signal sequence.

Embodiment 29 is a vaccine combination comprising one or more vectors together comprising nucleic acid sequences encoding (i) a first synthetic HIV envelope protein comprising the amino acid sequence of SEQ ID NO: 8 and (ii) a second HIV envelope protein comprising the amino acid sequence of SEQ ID NO: 5.

Embodiment 30 is a vaccine combination according to embodiment 29, wherein the first synthetic HIV envelope protein comprises the amino acid sequence of SEQ ID NO: 18.

Embodiment 31 is a vaccine combination comprising the following components:
(i) an Ad26 vector encoding a synthetic HIV envelope protein consisting of the amino acid sequence of SEQ ID NO: 18; and
(ii) an Ad26 vector encoding an HIV envelope protein consisting of the amino acid sequence of SEQ ID NO: 5.

Embodiment 32 is a vaccine combination according to embodiment 31, further comprising the following component:
(iii) an Ad26 vector encoding HIV antigens consisting of the amino acid sequence of SEQ ID NO: 28.

Embodiment 33 is a vaccine combination according to embodiment 31 or 32, further comprising the following component:
(iv) an Ad26 vector encoding HIV antigens consisting of the amino acid sequence of SEQ ID NO: 29.

Embodiment 34 is a vaccine combination according to any one of embodiments 31-33, further comprising the following component:
(v) isolated HIV antigenic polypeptide having residues 30-708 of the amino acid sequence of SEQ ID NO: 7, or residues 30-724 of the amino acid sequence of SEQ ID NO: 36, optionally further comprising an adjuvant.

Embodiment 35 is a method of inducing an immune response against a human immunodeficiency virus (HIV) in a human subject in need thereof, the method comprising:
(a) administering to the subject: (i) a rAd26 vector encoding a synthetic HIV envelope protein comprising the amino acid sequence of SEQ ID NO: 18; (ii) a rAd26 vector encoding an antigen comprising the amino acid sequence of SEQ ID NO: 5; (iii) a rAd26 vector encoding an antigen comprising the amino acid sequence of SEQ ID NO: 28; and (iv) a rAd26 vector encoding an antigen comprising the amino acid sequence of SEQ ID NO: 29; preferably wherein the rAd26 vectors are administered in a ratio of about 1:1:1:1 at a total dose of about $1\text{-}10\times10^{10}$ viral particles (vp), e.g. $5\times10^{10}$ vp;
(b) repeating step (a) at about 10-14 weeks, e.g. at 12 weeks after step (a);
(c) administering to the subject: (i) a rAd26 vector encoding a synthetic HIV envelope protein comprising the amino acid sequence of SEQ ID NO: 18; (ii) a rAd26 vector encoding an antigen comprising the amino acid sequence of SEQ ID NO: 5; (iii) a rAd26 vector encoding an antigen comprising the amino acid sequence of SEQ ID NO: 28; (iv) a rAd26 vector encoding an antigen comprising the amino acid sequence of SEQ ID NO: 29; (v) isolated HIV gp140 protein having the sequence of amino acids 30-708 of SEQ ID NO: 7; and (vi) aluminium phosphate adjuvant; preferably wherein the rAd26 vectors are administered in a ratio of about 1:1:1:1 at a total dose of about $1\text{-}10\times10^{10}$ viral particles (vp), e.g. $5\times10^{10}$ vp and wherein the isolated HIV gp140 protein is administered at a dose of about 50-300 microgram, e.g. 250 microgram; at about 20-28 weeks, e.g. at 24 weeks after step (a); and
(d) repeating step (c) at about 42-54 weeks, e.g. at 48 weeks after step (a).

Embodiment 36 is a method of inducing an immune response against a human immunodeficiency virus (HIV) in a human subject in need thereof, the method comprising:
(a) administering to the subject: (i) a rAd26 vector encoding a synthetic HIV envelope protein comprising the amino acid sequence of SEQ ID NO: 18; (ii) a rAd26 vector encoding an antigen comprising the amino acid sequence of SEQ ID NO: 5; (iii) a rAd26 vector encoding an antigen comprising the amino acid sequence of SEQ ID NO: 28; and (iv) a rAd26 vector encoding an antigen comprising the amino acid sequence of SEQ ID NO: 29; preferably wherein the rAd26 vectors are administered in a ratio of about 1:1:1:1 at a total dose of about $1\text{-}10\times10^{10}$ viral particles (vp), e.g. $5\times10^{10}$ vp;
(b) repeating step (a) at about 10-14 weeks, e.g. at 12 weeks after step (a);
(c) administering to the subject: (i) a rAd26 vector encoding a synthetic HIV envelope protein comprising the amino acid sequence of SEQ ID NO: 18; (ii) a rAd26 vector encoding an antigen comprising the amino acid sequence of SEQ ID NO: 5; (iii) a rAd26 vector encoding an antigen comprising the amino acid sequence of SEQ ID NO: 28; (iv) a rAd26 vector encoding an antigen comprising the amino acid sequence of SEQ ID NO: 29; (v) isolated HIV gp140 protein having the sequence of amino acids 30-708 of SEQ ID NO: 7; (vi) isolated HIV gp140 protein having the sequence of amino acids 30-724 of SEQ ID NO: 36; and (vii) aluminium phosphate adjuvant; preferably wherein the rAd26 vectors are administered in a ratio of about 1:1:1:1 at a total dose of about $1\text{-}10\times10^{10}$ viral particles (vp), e.g. $5\times10^{10}$ vp and wherein the isolated HIV gp140 proteins are administered in a ratio of about 1:1 at a total dose of about 50-300 microgram, e.g. 250 microgram; at about 20-28 weeks, e.g. at 24 weeks after step (a); and
(d) repeating step (c) at about 42-54 weeks, e.g. at 48 weeks after step (a).

EXAMPLES

Example 1: Design of HIV Envelope Antigen Sequences

Several HIV envelope antigen sequences were designed having sequence similarity to the mosaic HIV antigen mos2Env (SEQ ID NO: 6; previously also described in WO 2010/059732). The newly designed, membrane bound, sequences were based on (a combination of) fully natural wild-type sequences from HIV envelope proteins, or a chimera of mos2Env sequence and wild-type HIV envelope protein sequences. In addition to full length envelope protein sequences (see FIG. 1A), sequences having a C-terminal truncation of the cytoplasmic domain were also designed (see, e.g., FIG. 1C). See also e.g., Schiernle et al., PNAS 1997; Abrahamyan et al., J Virol 2005); Edwards et al., *J. Virology*, 2002, 76:2683-2691. Soluble variants were also prepared by C-terminal truncation before the transmembrane (TM) region, which was replaced by a trimerization domain, such as a GCN4 trimerization domain (see, e.g., FIG. 1B). These soluble variants were further converted into a single chain variant by mutation of the furin-cleavage site, thus inhibiting the processing of the extracellular domain of the envelope protein into gp120 and gp41 subunits.

Of the all the constructs generated and tested, constructs based on C4 had the most optimal properties, e.g., good manufacturability, folding, immunogenicity, etc. and these were selected for further studies. A soluble variant of the C4 construct having a GCN4 trimerization domain in place of the transmembrane domain (sC4, FIG. 1B), and a variant comprising a 7-amino acid fragment of the cytoplasmic domain (C4D7, FIG. 1C) were also generated and tested in further studies. The amino acid sequences of C4, sC4, and C4D7 are shown in SEQ ID NOs: 17, 19, and 18, respectively. Sequences encoding these are shown in SEQ ID NOs: 25, 27, and 26, respectively. Construct C1 has an extracellular domain sequence based on the mos2Env sequence (SEQ ID NO: 6). A soluble variant of construct C1 having a GCN4 trimerization domain in place of the transmembrane domain (sC1), and a variant comprising a 7-amino acid fragment of the cytoplasmic domain (C1D7), similar to sC4 and C4D7 as shown in FIGS. 1B and 1C, respectively, were also generated. Construct C1 and its variants were used in further studies for comparison purposes, since these are essentially based on the mos2Env sequence of the prior art. The amino acid sequences of C1, sC1 and C1D7 are shown in SEQ ID NOs: 31, 30, and 32, respectively. Nucleic acid sequences encoding these are shown in SEQ ID NOs: 34, 33, and 35, respectively. Other constructs that were tested were less optimal than the ones based on construct C4, and were not taken into further development.

Example 2: Expression and Folding of Synthetic HIV Envelope Proteins

The expression level, folding, and cell-surface expression of synthetic HIV envelope proteins were measured.

Expression Levels

HEK293F cells were transiently transfected with a plasmid encoding the soluble synthetic HIV envelope proteins sC1 and sC4 as described in Example 1. Expression levels of the soluble protein were measured in the supernatant using quantitative Western blot (QWB). The results are shown in FIG. 2. The low expression levels for sC1 (which essentially corresponds to mos2Env with an added transmembrane domain) are in line with our recent insights for mos2Env. As demonstrated by the results, the sC4 variant of the invention showed significantly higher expression levels than the sC1 variant (control).

Protein Folding

Figure 3A:
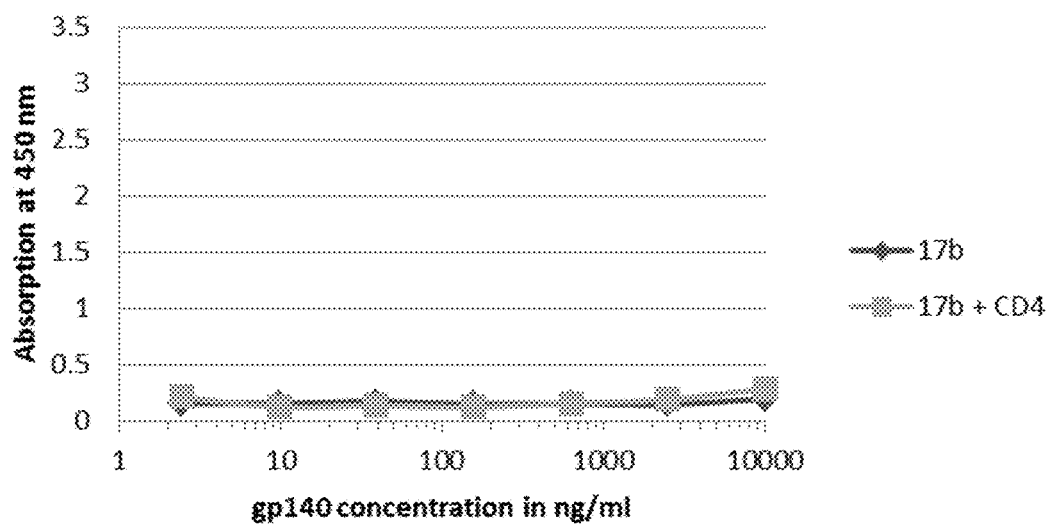
FIGS. 3A and 3B show the binding of synthetic HIV envelope proteins with monoclonal antibody 17b (mAb17b) in the presence (light gray) and absence (dark gray) of soluble CD4 as determined by ELISA assay.

Protein folding was tested by measuring the binding of soluble synthetic HIV envelope proteins to an antibody (MAb 17b) known to bind the co-receptor binding site of the HIV envelope protein, which is exposed only after binding of CD4, by enzyme-linked immunosorbent assay (ELISA). In particular, binding of purified sC4 was tested for binding to MAb 17b with prior binding of sC4 to CD4, and without prior binding of sC4 to CD4. Purified sC1 was used as a control. Binding of MAb 17b to sC4 without prior CD4 binding to the envelope protein is an indication of partially unfolded or pre-triggered envelope protein (i.e., an unstable Env that adopts the "open" conformation in the absence of CD4 binding). The results of the ELISA assay are shown in FIGS. 3A and 3B.

Figure 3B:
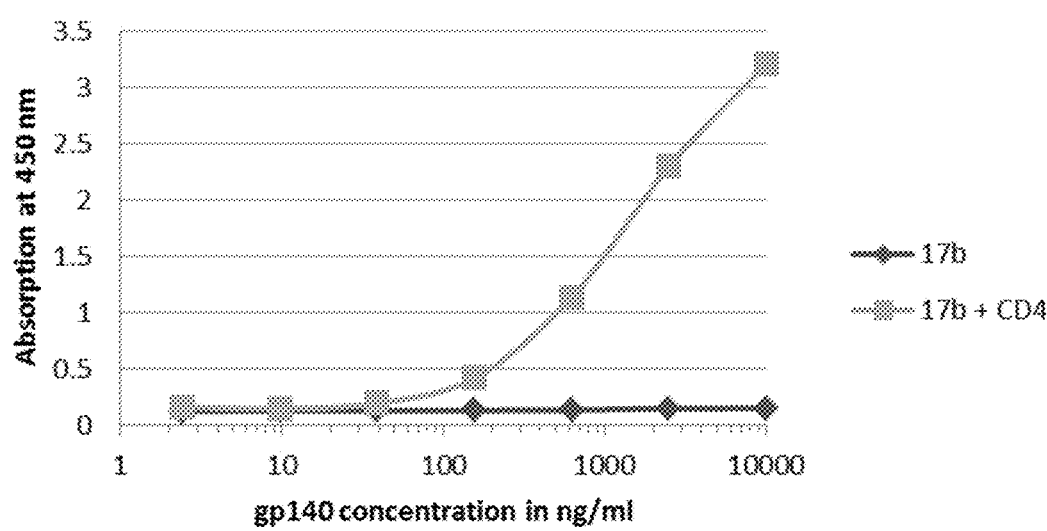

As shown in FIG. 3B, sC4 shows strong binding to MAb 17b with prior binding to CD4, but no detectable binding to MAb 17b without prior binding to CD4. In contrast, as shown in FIG. 3A, sC1 showed much lower binding to MAb 17 both with and without prior binding to CD4. The results suggest that sC4 has a correct folding pattern, with no exposure of the co-receptor binding site prior to CD4 binding.

Figure 4:
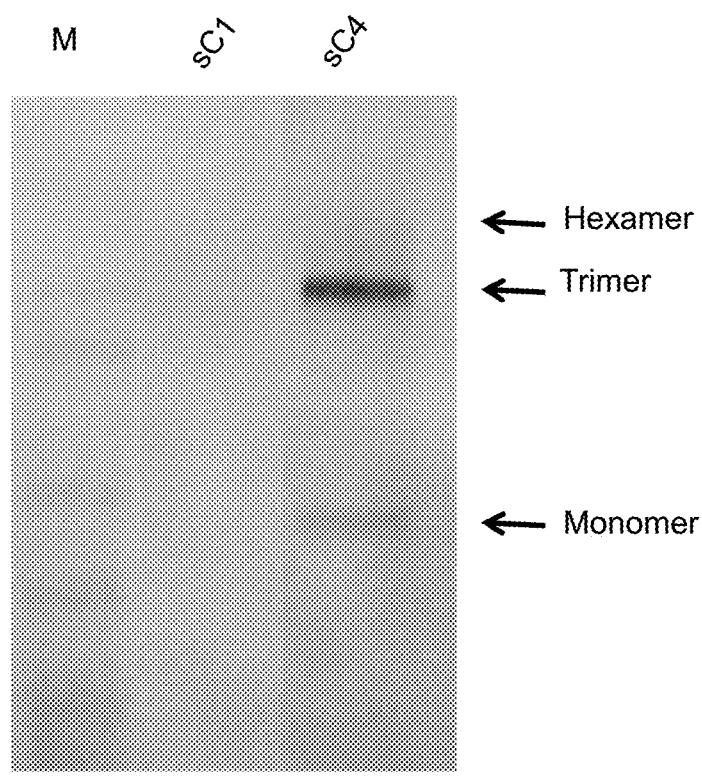
FIG. 4 is an image of a Western blot from a native polyacrylamide gel electrophoresis of the sC1 protein, and the sC4 synthetic HIV envelope protein.

Protein folding was also analyzed by native polyacrylamide gel electrophoresis (PAGE) of sC1 and sC4 to evaluate the quaternary structure of the soluble protein variants, and possible incorrect disulfide bridge formation between protomers. After electrophoresis on a native gel, protein in the gel was detected by Western blot analysis. As shown by the results in FIG. 4, the majority of sC4 is present in a trimeric state, which is the correct quaternary structure.

Taken together, the results of the protein folding experiments demonstrate that the sC4 soluble synthetic HIV envelope protein has the desired folding profile, which is improved as compared to the folding profile of the existing mos2Env antigen (represented by sC1).

Cell Surface Expression

Cell surface expression of the membrane-bound variants of HIV envelope proteins C1 (full length), C4 (full length, see FIG. 1A), C1D7, and C4D7 was also studied. HEK293T cells were transiently transfected with only eGFP-encoding plasmid (negative control, NC), or with eGFP-encoding plasmid together with an expression construct encoding an HIV envelope protein variant. Two days post-transfection, cells were subjected to fluorescence activated cell sorting (FACS)-analysis upon exposure to several poly- and monoclonal antibodies directed against gp120, and secondary antibodies, and then examined for envelope protein cell-surface expression levels. Quality of the envelope variants was assessed by determining the overall expression levels using an anti-gp120 polyclonal antibody, and by assessing relative binding of the broadly neutralizing antibodies PG9 and PG16, which are quaternary-structure dependent, and preferentially bind to correctly folded envelope trimer.

Figure 5:
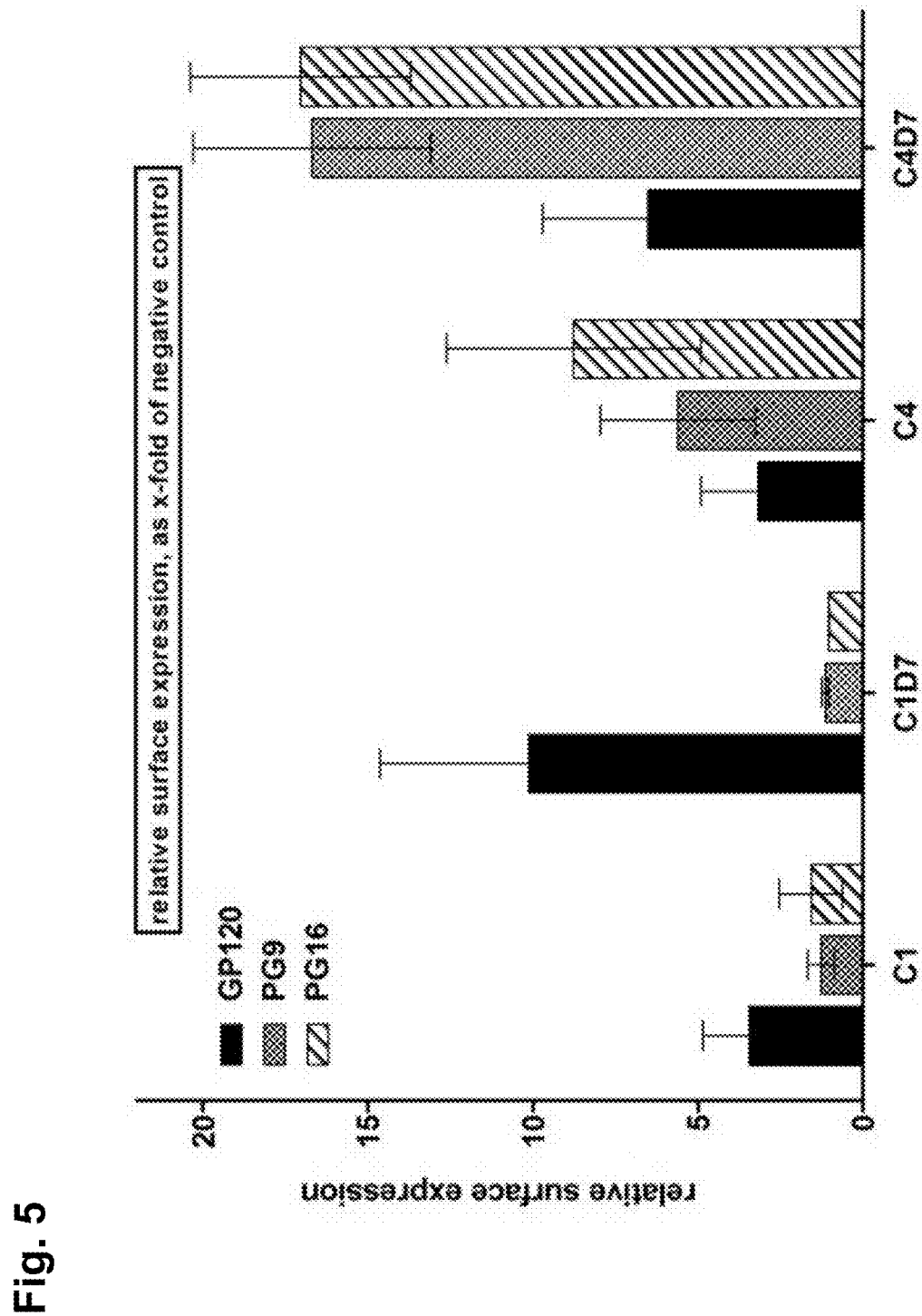
FIG. 5 shows the relative cell surface expression levels of the membrane-bound C1, C1D7, C4 and C4D7 synthetic HIV envelope proteins by FACS analysis of cells expressing these proteins using an anti-gp120 polyclonal antibody (GP120), and by binding to broadly neutralizing antibodies PG9 (PG9) and PG16 (PG16) that are quaternary-structure dependent and preferentially bind to correctly folded Env trimer.

The results of the cell surface expression experiments are shown in FIG. 5. The surface expression levels of truncated variants C1D7 and C4D7 as measured using an anti-gp120 antibody, are much higher than the surface expression levels of their full length counterparts, C1 and C4, respectively. This confirms that deletion of 144 residues from the carboxy-terminus of Env increases envelope surface expression levels. The full length C4 construct of the invention also showed improved PG9 and PG16 binding as compared to full length C1, suggesting that the C4 envelope sequence is properly folded (i.e., a trimer) on the cell surface.

The results also demonstrate that the C1D7 variant, which is essentially Mos2Env with an added transmembrane domain and 7 amino acids of the cytoplasmic domain, can be surface-expressed on HEK293T cells. This is in contrast to the soluble construct in Ad26.mos2Env, which cannot be expressed at detectable levels on the surface when transfected to A549 cells. However, relative binding to PG9 and PG16 is barely detectable above background, suggesting that the C1D7 envelope sequence is poorly folded and is probably not present as an intact trimer on the cell surface.

Overall, the C4D7 envelope variant has the most optimal antibody binding profile, with higher gp120 expression than its full-length counterpart C4, and with greater than 15-fold increased PG9 and PG16 binding compared to C1 and C1D7 (FIG. 5).

Example 3: Stability of Vectors Encoding HIV Envelope Sequences

Previous work in our laboratories (unpublished) indicated that adenovirus 26 (Ad26) vectors encoding the mos2Env antigen sequence showed had relatively high VP/IU ratios (indicating lower quality of adenovirus product batches) and moreover that such vectors displayed stability issues. Accordingly, it was important to test the stability of the synthetic HIV envelope proteins constructs of the invention in an adenovirus background.

Recombinant Ad26 (rAd26) vectors encoding HIV antigen sequences of the invention C4, C4D7, and sC4 as described above in Example 1 were generated in PER.C6 cells (referred to as "rAd26.C4", "rAd26.C4D7", and "rAd26.sC4", respectively). Vector clones (plaques) were picked and scaled-up for the generation of research batches. A maximum of 5 viral clones (plaques) were scaled-up to T25 format and serially passaged for 10 passages in T25 format (passages 1-3 being the transfection and plaque purification steps, followed by 10 passages in T25 format, resulting in a total of 13 passages). Genetic stability was assessed at viral passage number (vpn) 3, 5, 10 and 13 by an E1 transgene cassette PCR assay, followed by sequencing at vpn 13. The results are shown in FIG. 6.

Figure 6:
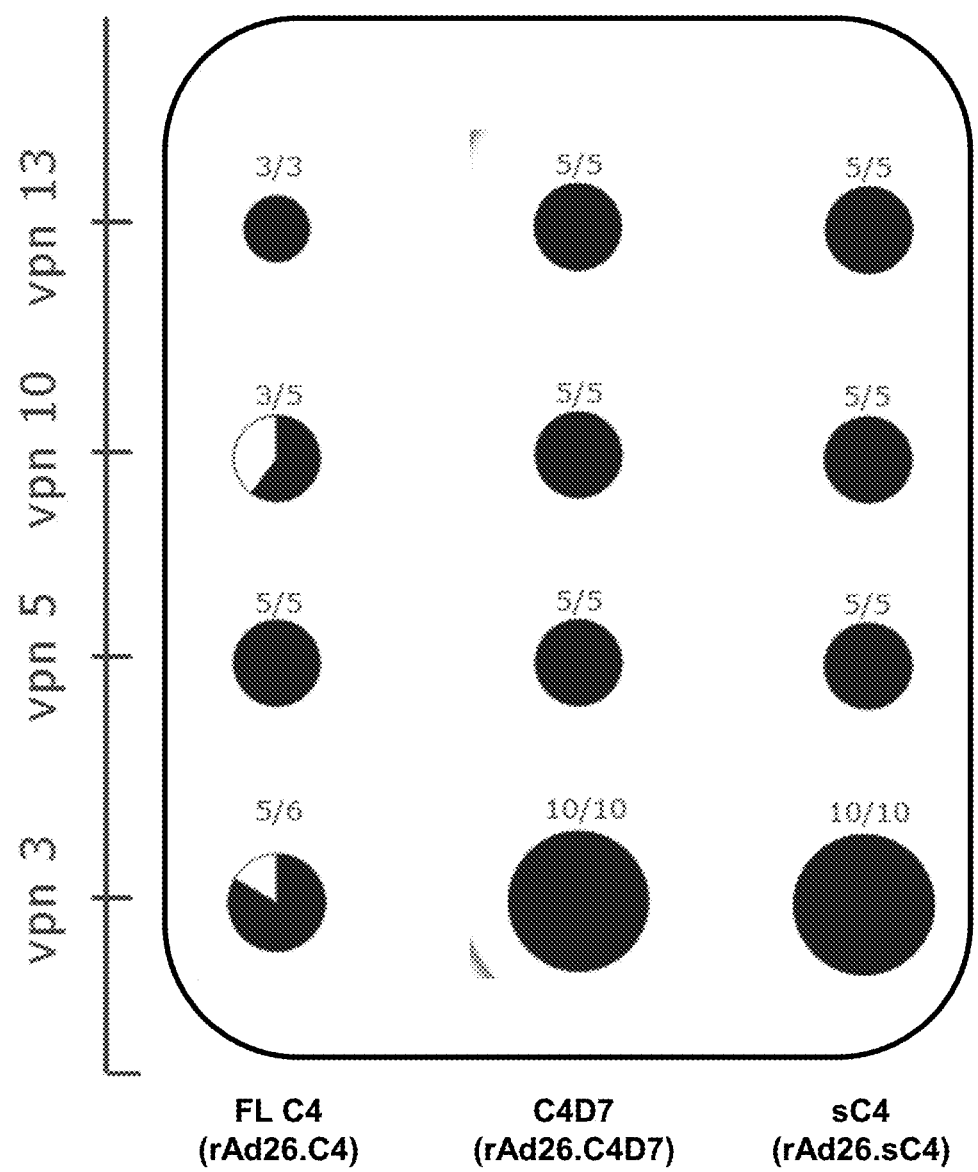
FIG. 6 is a graphical representation of the stability of adenovirus vectors containing sequences encoding synthetic HIV envelope proteins of the invention including full-length C4 (FLC4), C4D7, and sC4 after multiple viral passages; recombinant adenovirus 26 vectors were generated in PER.C6 cells; after the initial 3 passages for transfection and plaque purification, 5 plaques were selected and upscaled for 10 passages in T25 format, resulting in a total viral passage number (vpn) of 13; the stability after vpn 3, 5, 10, and 13 as determined by E1 transgene cassette polymerase chain reaction (PCR) is shown; for example, 3/5 means 3 plaques were stable out of 5 plaques tested, and 5/5 means 5 plaques were stable out of 5 plaques tested.

The rAd26 vectors encoding full length C4 (rAd26.C4) showed poor growth characteristics, as determined by no full cytopathogenic effect (CPE) in 2-3 days; genetic instability, as determined by deletions of the E1 transgene cassette region; or a combination thereof (FIG. 6). Due to the poor growth characteristics and observed genetic instability, this vector encoding full length C4 was not pursued further.

In contrast, for the rAd26 vectors encoding C4D7 (rAd26.C4D7) and sC4 (rAd26.sC4), all propagated plaques remained genetically stable during the course of the experiment (FIG. 6). Thus, the novel sC4 and C4D7 constructs outperform the original mos2Env construct with respect to stability in an adenoviral vector background. The genetic stability testing up to vpn 13 represents propagation several passages beyond that used in the industrial scale preparation of the vectors.

Example 4: Expression and In Vivo Antigenicity of HIV Envelope Sequences in Adenovirus Vectors Expression and antigenicity of rAd26.C4D7 and rAd26.sC4 were assessed separately or in combination with a recombinant Ad26 vector encoding mos1Env (SEQ ID NO: 5) (hereinafter "rAd26.mos1Env") in vector-transduced A549 cells (human cell line) in vitro (data not shown). Flow cytometry analysis demonstrated that all antigens were expressed in cell cultures transduced with either $2 \times 10^4$ viral particles (vp) of the single envelope antigens as controls, or with $1 \times 10^4$ vp of the 2 combined Env antigens by adenovirus transduction. All transductions additionally contained single doses ($1 \times 10^4$ vp) of adenovirus vectors encoding mos1GagPol ("rAd26.mos1GagPol") and mos2GagPol ("rAd26.mos2GagPol") (Barouch et al, Nat Med 2010, 16:319-323), so that the assessed vector combinations exhibited the same relative ratios of the different adenoviral vectors as intended for pre-clinical and clinical use. Preferably, the vectors encoding synthetic HIV envelope proteins of the invention are combined with vectors encoding the mos1GagPol and the mos2GagPol antigens for clinical use.

The combination of rAd26.mos1Env and rAd26.C4D7 yielded a maximal coverage of the assessed epitopes as determined by monoclonal antibody binding. Particularly, the exposure of the PG16 epitope, which was contributed by transformation with Ad26.C4D7 is promising for vaccine use since PG16 represents a broadly neutralizing monoclonal antibody recognizing the V1/V2 loop region of HIV-1 Env (Walker et al, Science. 2009). Hence, the synthetic HIV envelope protein of the invention derived from the C4 sequence increases the breadth of the immune response against the HIV envelope protein compared to the immune response generated by mos1Env only. Vaccine-induced antibody responses directed towards the envelope protein region have been shown to correlate with protection from HIV-1 infection in the RV144 study (Haynes et al, N Engl J Med. 2012), and thus the synthetic HIV envelope protein of the invention is a promising candidate to include in HIV vaccine regimens.

Example 5: Immunogenicity of Vectors Encoding Synthetic HIV Envelope Proteins

The synthetic HIV envelope protein sequences of the invention in an Ad26 vector background were tested in rabbits to determine if these constructs were an immunogenic alternative to the rAd26.mos2Env construct.

The immunogenicity of adenovirus vector encoding mos1Env (rAd26.mos1Env; SEQ ID NO: 5) was tested alone, and in combination with adenovirus vectors encoding synthetic HIV envelope proteins of the invention (rAd26.C4D7 and rAd26.sC4; comprising SEQ ID NO: 8, in particular SEQ ID NOs: 18 and 19, respectively). In all cases, adenovirus 26 vectors encoding mos1GagPol and mos2GagPol antigens (rAd26.mos1GagPol [SEQ ID NO: 28] and rAd26.mos2GagPol [SEQ ID NO: 29], respectively) were also administered. More specifically, the immunogenicity of rAd26.mos1Env alone (trivalent vaccine: rAd26.mos1GagPol, rAd26.mos2GagPol and rAd26.mos1Env) was compared to the immunogenicity of rAd26.mos1Env in combination with one of rAd26.C4D7 or rAd26.sC4 (tetravalent vaccine: administration of either rAd26.mos1GagPol, rAd26.mos2GagPol, rAd26.mos1Env and rAd26.C4D7; or administration of rAd26.mos1GagPol, rAd26.mos2GagPol, rAd26.mos1Env and rAd26.sC4). This comparison of the trivalent vaccine, which lacks any vectors encoding the synthetic HIV envelope proteins of the invention, with the tetravalent vaccine, which contains vectors encoding the synthetic HIV envelope proteins of the invention, allows for a determination of whether the HIV envelope proteins of the invention contribute to the breadth of protection.

Administration was done in vaccine regimens, wherein these Ad26 vectors were administered at weeks 0 and 6 as a double prime, and a clade C gp140 protein (a trivalent Env gp140 protein having SEQ ID NO: 7 without the signal peptide sequence of residues 1-29, see also WO 2010/042942) at weeks 12 and 18 as a double boost (see e.g. Barouch et al, 2015, Science 349: 320-324). Table 1 describes the vaccine regimens used for the current study. rAd26.Empty refers to a control vector lacking any gene encoding a sequence for an HIV antigenic protein. Each group contained six rabbits.

TABLE 1

Vaccine regimens tested in immunogenicity study in rabbits

| | | First and second Immunizations | | Third and fourth immunizations | | | |
|---|---|---|---|---|---|---|---|
| Group | adeno vectors | Dose (vp) | Total dose (vp) | protein boost | Dose (ug) | Adjuvant | N = |
| 1 | rAd26.Mos1Env | $2.5 \times 10^{10}$ | $5 \times 10^{10}$ | GP140 (clade C) | 10 | AdjuPhos 250 µg | 6 |
|   | rAd26.Mos1GagPol | $1.25 \times 10^{10}$ | | | | | |
|   | rAd26.Mos2Gagpol | $1.25 \times 10^{10}$ | | | | | |
| 2 | rAd26.Mos1Env | $1.25 \times 10^{10}$ | $5 \times 10^{10}$ | GP140 (clade C) | 10 | AdjuPhos 250 µg | 6 |
|   | rAd26.C4D7 | $1.25 \times 10^{10}$ | | | | | |
|   | rAd26.Mos1GagPol | $1.25 \times 10^{10}$ | | | | | |
|   | rAd26.Mos2Gagpol | $1.25 \times 10^{10}$ | | | | | |
| 3 | rAd26.Mos1Env | $1.25 \times 10^{10}$ | $5 \times 10^{10}$ | GP140 (clade C) | 10 | AdjuPhos 250 µg | 6 |
|   | rAd26.sC4 | $1.25 \times 10^{10}$ | | | | | |
|   | rAd26.Mos1GagPol | $1.25 \times 10^{10}$ | | | | | |
|   | rAd26.Mos2Gagpol | $1.25 \times 10^{10}$ | | | | | |
| control | rAd26.Empty | $5 \times 10^{10}$ | $5 \times 10^{10}$ | NA | 0 | AdjuPhos 250 µg | 6 |

The comparison of the trivalent Ad26 vaccine (lacking the novel Env antigens of the invention) with the tetravalent Ad26 vaccine (which comprises the novel sC4 or C4D7 Env antigens) allows for testing if the novel antigens contribute to breadth of protection. An established TZM-bl cell-based neutralization assay [Montefiori D C. *Methods Mol Biol* 2009, 485:395-405; Sarzotti-Kelsoe M et al., *J Immunol Methods* 2014, 409:131-146] was used to measure neutralizing activity of the vaccine candidates.

Figure 7A:
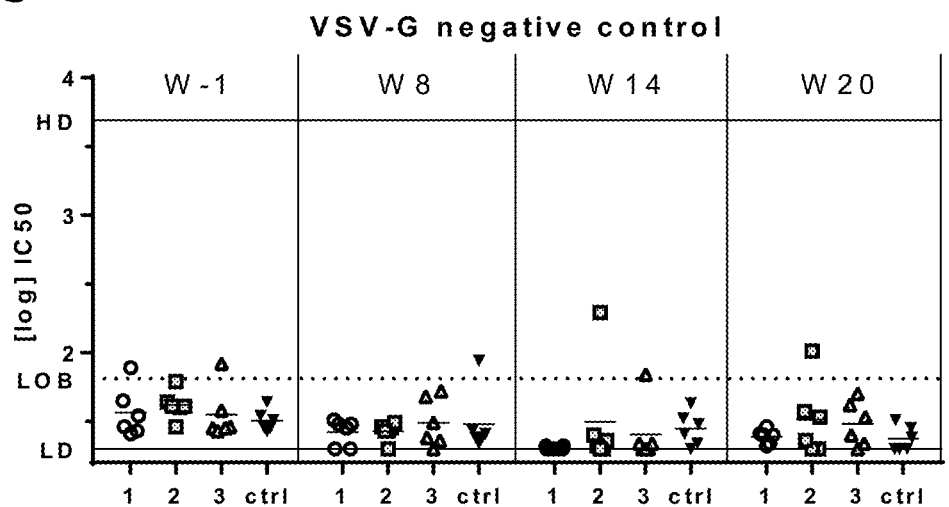
FIGS. 7A and 7B show virus neutralization titers against HIV-1 envelope pseudotyped virus particles (EVPs) in a TZM-bl cell-based neutralization assay in rabbits; log 10-transformed $IC_{50}$ values of the high-adenoviral vector dosed groups were measured against EVPs VSV-G (negative control) and MW965.26 (Tier 1A clade C) at weeks 1, 8, 14, and 20; each dot represents the log 10-transformed $IC_{50}$ value of an individual rabbit, with the group mean indicated by a horizontal line; HD: Highest Dilution tested (upper solid line); LD: Lowest Dilution tested (lower solid line); LOB: limit of background, 95 percentile value of compiled negative samples (dotted line); Log 10 $IC_{50}$ values exceeding the LD or HD threshold were set at the corresponding line; a one-way non-parametric comparison with control using the Dunn method for joint ranking was done for each time point; statistically significant differences are indicated in the graphs: *=P<0.05, =P<0.01, and *=P<0.001.
Figure 7B:
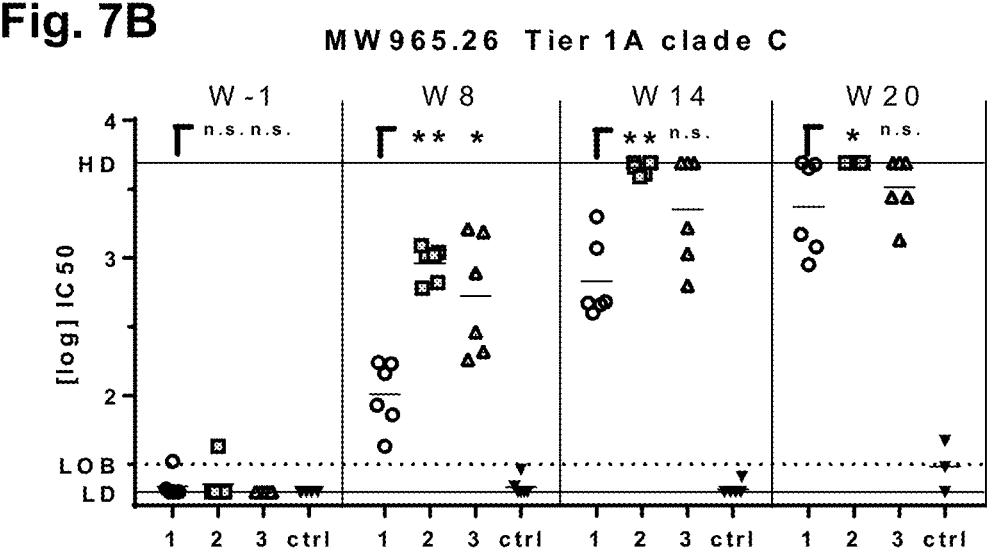

Results are shown in FIGS. 7A and 7B, and were statistically analyzed by using the trivalent vaccine (group 1 in Table 1) as control group and comparing to each of the novel quadrivalent vaccines (groups 2 and 3 in Table 1).

Overall, the novel C4-derived (i.e. encoding Env proteins comprising SEQ ID NO: 8, being an alternative for mos2Env) adeno constructs were immunogenic after two homologous intramuscular immunizations in rabbits.

Neutralization capacity of rabbit immune sera against Tier 1B pseudoviruses was absent (data not shown), which is not unexpected as it was known that such viruses are more difficult to neutralize.

Pseudovirus neutralization capacity of rabbit immune sera against a clade B Tier 1A virus was unaffected by the addition of new components (data not shown). This demonstrates that the novel antigen did not negatively interfere with immunogenicity of the existing clade B antigen present in the vaccine (although the new components were directed to clade C, such undesirable interference could not be excluded a priori before it had been tested).

Pseudovirus neutralization capacity of rabbit immune sera against a clade C Tier 1A virus was significantly enhanced in the quadrivalent novel C4D7 containing adeno (quadrivalent, group 2), compared to trivalent (having only mos1Env) immunization alone (group 1) (FIG. 7B). In addition, pseudovirus neutralization capacity of rabbit immune sera against a clade C Tier 1A virus at week 8 was significantly enhanced in the quadrivalent novel sC4 containing adeno (quadrivalent, group 3), compared to trivalent (having only mos1Env) immunization alone (group 1) (FIG. 7B).

In conclusion, the C4D7 and sC4 constructs encoded in Ad26 were immunogenic and addition thereof expanded the binding- and neutralization capacity of a vaccine that has mos1Env (mainly clade B) as sole Ad26-encoded Env component, towards clade C strains (FIG. 7B).

Example 6: Immunogenicity of Vaccine Regimens Including Vectors Encoding Synthetic HIV Envelope Proteins of the Invention One further rabbit study assessed the tetravalent vector combination Ad26.Mos4.HIV (consisting of four adenoviral vectors: Ad26.Mos1GagPol [encoding SEQ ID NO: 28], Ad26.Mos2GagPol [encoding SEQ ID NO: 29], Ad26.Mos1Env [encoding SEQ ID NO: 5] and Ad26.Mos2SEnv [the name "C4D7" as used above is also referred to as "Mos2S"; this vector encodes the novel SEQ ID NO: 18 according to the invention], in a 1:1:1:1 mixture at a total dose of $5 \times 10^9$ vp,) applied intramuscularly as double prime immunizations in weeks 0 and 6, in combination with recombinant HIV-1 Env protein boosts using Clade C gp140 [having the sequence of amino acid residues 30-708 of SEQ ID NO: 7], Mosaic gp140 [having the sequence of amino acid residues 30-724 of SEQ ID NO: 36], or a combination of Clade C gp140 and Mosaic gp140, in weeks 13 and 19. These protein boosts were applied intramuscularly at a total dose of 10 or 50 micrograms of protein combined with 250 mcg aluminum phosphate adjuvant formulated on the day of immunization.

Results indicate that all tested regimens were immunogenic in all animals, inducing high antibody titers and moderate neutralization activity against Tier 1 Env pseudotyped viruses. If Mosaic gp140 was used as vaccine antigen, either alone or in combination with Clade C gp140, Mosaic gp140-specific ELISA titers and Clade B pseudovirus recognition were significantly increased at week 15 in comparison to the reference group boosted with Clade C gp140 alone. The overall effect size of the improvement was moderate, and bigger for the group boosted with the bivalent Clade C gp140-Mosaic gp140 combination compared to Mosaic gp140 alone. At week 21 of the study, these differences were lost and immune responses measured for the cohorts receiving bivalent Clade C gp140-Mosaic gp140 boosts or monovalent Clade C gp140 boosts were statistically indistinguishable.

The bivalent protein regimen showed comparable induction of Clade C ELISA titers and pseudovirus recognition as the Clade C gp140 alone boosted regimen, indicating that the inclusion of the clade B-related immunogen Mosaic gp140 had no negative effect on clade C antigen coverage, whilst significantly enhancing clade B coverage at week 15 of the study.

The data confirm that the Ad26.Mos2SEnv vector encoding a synthetic Env antigen according to the invention can be successfully used in vaccine regimens.

REFERENCES

1. Barouch et al, *Nat Med* 2010, 16: 319-323
2. WO 2010/059732
3. Schiernle et al., *PNAS* 94: 8640-8645, 1997
4. Abrahamyan et al., *J Virol* 79: 106-115, 2005
5. US20120076812
6. Barouch et al., *Cell* 155:1-9, 2013
7. Havenga, et al., 2006, *J Gen Virol* 87: 2135-43;
8. WO 03/104467
9. WO 2004/001032
10. WO 2007/104792
11. Abbink et al., (2007) *Virol* 81(9): 4654-63
12. U.S. Pat. No. 7,270,811
13. Vogels et al., (2003) *J Virol* 77(15): 8263-71
14. WO 00/70071
15. WO2012/082918
16. Walker L M, Phogat S K, Chan-Hui P Y, Wagner D, Phung P, Goss J L, et al. Broad and potent neutralizing antibodies from an African donor reveal a new HIV-1 vaccine target. *Science* 2009, 326:285-289.
17. Haynes B F, Gilbert P B, McElrath M J, Zolla-Pazner S, Tomaras G D, Alam S M, et al. Immune-correlates analysis of an HIV-1 vaccine efficacy trial. *N Engl J Med* 2012, 366:1275-1286.
18. Barouch et al. (2015) *Science* 349: 320-324
19. Montefiori D C. Measuring HIV neutralization in a luciferase reporter gene assay. *Methods Mol Biol* 2009, 485:395-405.
20. Sarzotti-Kelsoe M, Bailer R T, Turk E, Lin C L, Bilska M, Greene K M, et al. Optimization and validation of the TZM-bl assay for standardized assessments of neutralizing antibodies against HIV-1. *J Immunol Methods* 2014, 409:131-146.
21. Edwards et al., *J. Virology*, 2002, 76:2683-2691.

The invention claimed is:

1. A composition comprising:
   (i) a first adenovirus 26 (Ad26) vector encoding a synthetic HIV envelope protein comprising the amino acid sequence of SEQ ID NO: 18;
   (ii) a second Ad26 vector encoding an HIV antigenic polypeptide comprising the amino acid sequence of SEQ ID NO: 5;
   (iii) a third Ad26 vector encoding an HIV antigenic polypeptide comprising the amino acid sequence of SEQ ID NO: 28; and
   (iv) a fourth Ad26 vector encoding an HIV antigenic polypeptide comprising the amino acid sequence of SEQ ID NO: 29.

2. The composition of claim 1, wherein the first, second, third and fourth Ad26 vectors are present in a viral particle ratio of 1:1:1:1.

3. A combination of compositions for inducing an immune response against HIV, comprising:
   (a) a first composition which is the composition of claim 1; and
   (b) a second composition comprising:
   (b, i) an isolated HIV antigenic polypeptide having residues 30-708 of the amino acid sequence of SEQ ID NO: 7, or
   (b, ii) an isolated HIV antigenic polypeptide having residues 30-724 of the amino acid sequence of SEQ ID NO: 36, or
   (b, iii) an isolated HIV antigenic polypeptide having residues 30-708 of the amino acid sequence of SEQ ID NO: 7 and an isolated HIV antigenic polypeptide having residues 30-724 of the amino acid sequence of SEQ ID NO: 36.

4. The vaccine combination of compositions of claim 3, wherein the second composition comprises an isolated HIV antigenic polypeptide having residues 30-708 of the amino acid sequence of SEQ ID NO: 7.

5. The combination of compositions of claim 3, wherein the second composition comprises an isolated HIV antigenic polypeptide having residues 30-708 of the amino acid sequence of SEQ ID NO: 7 and an isolated HIV antigenic polypeptide having residues 30-724 of the amino acid sequence of SEQ ID NO: 36.

6. A method for inducing an immune response against HIV in a subject, comprising administering to the subject the composition of claim 1.

7. The combination of compositions of claim 3, wherein the second composition further comprises an adjuvant.

8. The combination of compositions of claim 4, wherein the second composition further comprises an adjuvant.

9. The combination of compositions of claim 5, wherein the second composition further comprises an adjuvant.

10. The combination of compositions of claim 7, wherein the adjuvant is aluminum phosphate.

11. The combination of compositions of claim 8, wherein the adjuvant is aluminum phosphate.

12. The combination of compositions of claim 9, wherein the adjuvant is aluminum phosphate.

13. A method for inducing an immune response against HIV in a subject, comprising administering to the subject the composition of claim 2.

14. The method of claim 6, wherein the subject is a human subject.

15. The method of claim 13, wherein the subject is a human subject.

* * * * *